United States Patent
Liu et al.

(10) Patent No.: US 9,840,520 B2
(45) Date of Patent: Dec. 12, 2017

(54) HETEROCYCLIC HYDROXAMIC ACIDS AS PROTEIN DEACETYLASE INHIBITORS AND DUAL PROTEIN DEACETYLASE-PROTEIN KINASE INHIBITORS AND METHODS OF USE THEREOF

(71) Applicant: The Regents of the University of Colorado, A Body Corporate, Denver, CO (US)

(72) Inventors: Xuedong Liu, Niwot, CO (US); Gan Zhang, Niwot, CO (US); Daniel Chuen-Fong Chan, Denver, CO (US); Anthony D. Piscopio, Longmont, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 15/310,743

(22) PCT Filed: May 14, 2015

(86) PCT No.: PCT/US2015/030842
§ 371 (c)(1),
(2) Date: Nov. 11, 2016

(87) PCT Pub. No.: WO2015/175813
PCT Pub. Date: Nov. 19, 2015

(65) Prior Publication Data
US 2017/0081343 A1    Mar. 23, 2017

Related U.S. Application Data

(60) Provisional application No. 61/996,691, filed on May 14, 2014, provisional application No. 61/996,702, filed on May 14, 2014.

(51) Int. Cl.
*C07D 513/04* (2006.01)
*C07D 473/34* (2006.01)
(Continued)

(52) U.S. Cl.
CPC .......... *C07D 513/04* (2013.01); *C07D 473/16* (2013.01); *C07D 473/34* (2013.01); *C07D 487/04* (2013.01)

(58) Field of Classification Search
None
See application file for complete search history.

(56) References Cited

U.S. PATENT DOCUMENTS

| | | |
|---|---|---|
| 2004/0176393 A1 | 9/2004 | Newton et al. |
| 2005/0038246 A1 | 2/2005 | Arnold et al. |

FOREIGN PATENT DOCUMENTS

| | | | |
|---|---|---|---|
| WO | 2013/041407 A1 | | 3/2013 |
| WO | 2013041407 | * | 3/2013 |

OTHER PUBLICATIONS

Chueh et al., "Mechanisms of Histone Deacetylase Inhibitor-Regulated Gene Expression in Cancer Cells".Antioxidants & Redox Signaling. 23 (1): 66-84.*

(Continued)

*Primary Examiner* — Karl J Puttlitz
(74) *Attorney, Agent, or Firm* — Morgan, Lewis & Bockius LLP

(57) ABSTRACT

The present invention relates to novel hydroxamic acids which are specific histone deacetylase (HDAC) inhibitors and/or TTK/Mps1 kinase inhibitors, including pharmaceutically acceptable salts thereof, which are useful for modulating HDAC and/or TTK/Mps1 kinase activity, pharmaceutical compositions comprising these compounds, and processes for their preparation.

43 Claims, 3 Drawing Sheets

(51) Int. Cl.
*C07D 487/04* (2006.01)
*C07D 473/16* (2006.01)

(56) References Cited

OTHER PUBLICATIONS

International Search Report and Written Opinion dated Jul. 29, 2015 in corresponding PCT/US2015/030842 application.
Aldana-Masangkay et al., "The Role of HDAC6 in Cancer," Journal of Biomedicine and Biotechnology, 875824: 1-10 (2011).
Tardif et al., "Characterization of the Cellular and Antitumor Effects of MPI-0479605, a Small-Molecule Inhibitor of the Mitotic Kinase Mps1," Molecular Cancer Therapeutics, 10: 2267-2275 (2011).
Glozak et al., "Histone deacetylases and cancer," Oncogene, 26: 5420-5432 (2007).
Bradner et al., "Chemical Phylogenetics of Histone Deacetylases," Nature Chemical Biology, 6: 238-243 (2010).
Conley et al., "Targeting Epigenetic Abnormalities With Histone Deacetylase Inhibitors," Cancer, 107: 832-840 (2006).
Iwata et al., "HDAC6 and Microtubules Are Required for Autophagic Degradation of Aggregated Huntingtin," Journal of Biological Chemistry, 280: 40282-40292 (2005).
Kawaguchi et al., "The Deacetylase HDAC6 Regulates Aggresome Formation and Cell Viability in Response to Misfolded Protein Stress," Cell, 115: 727-738 (2003).
Lee et al., "HDAC6 controls autophagosome maturation essential for ubiquitin-selective quality-control autophagy," EMBO Journal, 29: 969-980 (2010).
Li et al., "Histone deacetylase 6 plays a role as a distinct regulator of diverse cellular processes," FEBS Journal, 280: 775-793 (2012).
Mak et al., "Regulation of CD133 by HDAC6 Promotes β-Catenin Signaling to Suppress Cancer Cell Differentiation," Cell Reports, 2: 951-963 (2012).
Marks et al., "Histone Deacetylases and Cancer: Causes and Therapies," Nature, 1: 194-202 (2001).
Namdar et al., "Selective inhibition of histone deacetylase 6 (HDAC6) induces DNA damage and sensitizes transformed cells to anticancer agents," PNAS, 107: 20003-20008 (2010).
Pandey et al., "HDAC6 rescues neurodegeneration and provides an essential link between autophagy and the UPS," Nature, 447: 859-863 (2007).
Liu et al., "The MPS1 Family of Protein Kinases," Annual Review of Biochemistry, 81: 561-585 (2012).
Rivieccio et al., "HDAC6 is a target for protection and regeneration following injury in the nervous system," PNAS, 106: 19599-19604 (2009).
Fisk et al., "Human Mps1 protein kinase is required for centrosome duplication and normal mitotic progression," PNAS, 100: 14875-14880 (2003).
Kilpinen et al., "Analysis of Kinase Gene Expression Patterns across 5681 Human Tissue Samples Reveals Functional Genomic Taxonomy of the Kinome," PLoS One, 5: 1-14 (2010).
Kops et al., "Lethality to human cancer cells through massive chromosome loss by inhibition of the mitotic checkpoint," PNAS, 101: 8699-8704 (2004).
Michel et al., "Complete loss of the tumor suppressor MAD2 causes premature cyclin B degradation and mitotic failure in human somatic cells," PNAS, 101: 4459-4464 (2004).
Mills et al., "Expression of TTK, a Novel Human Protein Kinase, Is Associated with Cell Proliferation," Journal of Biological Chemistry, 267: 16000-16006 (1992).
Nakagawa et al., "Generation of induced pluripotent stem cells without Myc from mouse and human fibroblasts," Nature Biotechnology, 26: 101-106 (2008).
Niittymäki et al., "High frequency of TTK mutations in microsatellite-unstable colorectal cancer and evaluation of their effect on spindle assembly checkpoint," Carcinogenesis, 32: 305-311 (2011).
Simões-Pires et al., "HDAC6 as a target for neurodegenerative diseases: what makes it different from the other HDACs?" Molecular Neurodegeneration, 8: 1-16 (2013).
Sotillo et al., "Mad2 overexpression promotes aneuploidy and tumorigenesis in mice," Cancer Cell., 11: 9-23 (2007).
Strahl et al., "The language of covalent histone modifications," Nature, 403: 41-45 (2000).
Valenzuela-Fernández et al., "HDAC6: a key regulator of cytoskeleton, cell migration and cell-cell interactions," Trends in Cell Biology, 18: 291-297 (2008).
Weaver et al., "Decoding the links between mitosis, cancer, and chemotherapy: The mitotic checkpoint, adaptation, and cell death," Cancer Cell, 8: 7-12 (2005).
Yang et al., "HATs and HDACs: from structure, function and regulation to novel strategies for therapy and prevention," Oncogene, 26: 5310-5318 (2007).
Yuan et al., "Increased Expression of Mitotic Checkpoint Genes in Breast Cancer Cells with Chromosomal Instability," Clinical Cancer Research, 12: 405-410 (2006).
Salvatore et al., "A Cell Proliferation and Chromosomal Instability Signature in Anaplastic Thyroid Carcinoma," Cancer Research, 67: 10148-10158 (2007).

* cited by examiner

HETEROCYCLIC HYDROXAMIC ACIDS AS PROTEIN DEACETYLASE INHIBITORS AND DUAL PROTEIN DEACETYLASE-PROTEIN KINASE INHIBITORS AND METHODS OF USE THEREOF

STATEMENT OF RIGHTS TO INVENTIONS MADE UNDER FEDERALLY SPONSORED RESEARCH

This invention was made with government support under R01 CA 107098 and W81XWH-10-1-0989, awarded by National Institute of Health and the Army/Medical Research Material and Command. The government has certain rights in the invention.

FIELD OF THE INVENTION

The present invention relates to novel hydroxamic acids which are specific histone deacetylase (HDAC) inhibitors and/or TTK/Mps1 kinase inhibitors, including pharmaceutically acceptable salts thereof, and which are useful for modulating HDAC and/or TTK/Mps1 kinase activity, therefore altering cellular activities such as signal transduction, cell proliferation, cell survival and cytokine secretion. More specifically, the invention relates to hydroxamate compounds which inhibit, regulate and/or modulate HDAC and or TTK/Mps1 kinase activity, such as HDAC6 and/or TTK/Mps1 kinase activity, and signal transduction pathways relating to cellular activities as mentioned above.

BACKGROUND OF THE INVENTION

Histone deacetylases (HDACs) catalyze the removal of acetyl groups from lysine residues in histone amino termini, leading to chromatin condensation and changes in gene expression. Reversible lysine acetylation is an important phenomenon for homeostatic regulation of many cellular processes. The best characterized proteins that are subjected to this mode of regulation are histones (Strahl, B. D et al., *Nature* 2000, 403, (6765), 41-5). Lysine residues in the N-terminal tail are tightly regulated by acetylation and deacetylation catalyzed by enzymes known as histone acetyltransferase (HAT) or histone deacetylase (HDAC) (Minucci, S. et al., *Nat Rev Cancer* 2006, 6, (1), 38-51; Yang, X. J. et al., *Oncogene* 2007, 26, (37), 5310-8). Acetylation of lysines in the histone H3 and histone H4 tails is strongly correlated to chromatin states that are primed for transcription, or that are part of actively transcribed genomic regions (Strahl, B. D. et al., *Nature* 2000, 403, (6765), 41-5; Minucci, S. et al., *Nat Rev Cancer* 2006, 6, (1), 38-51). Acetylation of histones has also been correlated with other important cellular functions including chromatin assembly, DNA repair, and recombination.

There are 18 HDAC enzymes in the human genome that are subdivided into four distinct classes (Lane, A. A. et al., *J Clin Oncol* 2009, 27, (32), 5459-68; Marks, P. et al., *Nat Rev Cancer* 2001, 1, (3), 194-202). Classes I, II and IV (11 enzymes) contain a zinc ($Zn^{2+}$) molecule in their active site. Class III contains seven mechanistically diverse NAD+-dependent enzymes known as sirtuins. Class II is subdivided into Class IIa (HDAC4, 5, 7 and 9) and Class IIb (HDAC6 and HDAC10).

Alterations in histone modifications have emerged as one of the key mechanisms responsible for tumor transformation (Conley, B. A. et al., *Cancer* 2006, 107, (4), 832-40; Glozak, M. A. et al., *Oncogene* 2007, 26, (37), 5420-32). Altered expression and mutations of genes that encode HDACs have been linked to tumor development since they both induce the aberrant transcription of key genes regulating important cellular functions such as cell proliferation, cell-cycle regulation and apoptosis (Lane, A. A. et al., *J Clin Oncol* 2009, 27, (32), 5459-68; Marks, P. et al., *Nat Rev Cancer* 2001, 1, (3), 194-202). Hence inhibitors of histone deacetylase enzymes (HDACi) have recently attracted substantial attention as potential anti-cancer drugs. The clinical relevance of this attention that is warranted has recently been underscored by the introduction of vorinostat (Zolinza™, Merck, also widely known SAHA=suberoylanilide hydroxamic acid), Romidepsin (Istodax) and Belinostat for the treatment of cutaneous T-cell lymphoma (Marks, P. A., et al., *Expert Opin Investig Drugs* 2010, 19, (9), 1049-66).

Class II HDAC enzymes exhibit tissue-specific expression and can shuttle between the nucleus and cytoplasm. There is a growing interest in this class of HDAC enzymes because their substrates are broader and not limited to histones. For example, Class IIb enzyme HDAC6 predominantly resides in cytoplasm and hence its substrates are nonhistone proteins including α-tubulin, cortactin, peroxiredoxins, chaperone proteins, HSP90, β-Catenin, hypoxia inducible factor-1α (HIF-1α) and other proteins (Li, Y. et al., *FEBS J* 2013, 280, (3), 775-93; Shankar, S. et al., *Adv Exp Med Biol* 2008, 615, 261-98).

HDAC6 contains two functional homologous catalytic domains and an ubiquitin-binding zinc finger domain at the C-terminal region. HDAC6 is an authentic protein lysine deacetylase and appears to be important for a myriad biological processes and aberrant regulation of HDAC6 is implicated in numerous pathological conditions from cancer to neurodegenerative diseases (Valenzuela-Fernandez, A. et al., *Trends Cell Biol* 2008, 18, (6), 291-7; Simoes-Pires, C. et al., *Mol Neurodegener* 2013, 8, (1), 7).

HDAC6 stably associates with tubulin and regulate its acetylation states. Since microtubules are at the heart of cellular self-organization, it is not surprising that the deacetylation activity of HDAC6 towards tubulin affects many cellular processes. HDAC6 is known to play important roles in cell migration and cell-cell interaction. Aberrant regulation of HDAC6 is associated with cancer development (Valenzuela-Fernandez, A. et al., *Trends Cell Biol* 2008, 18, (6), 291-7; Simoes-Pires, C. et al., *Mol Neurodegener* 2013, 8, (1), 7). For example, overexpression of HDAC6 correlates with invasive metastatic behavior of tumor cells (Aldana-Masangkay, G. I. et al., *J Biomed Biotechnol* 2011, 875824). Moreover, HDAC6 directly or indirectly regulates angiogenesis by deacetylating several key factors that control angiogenesis (Li, Y. et al., *FEBS J* 2013, 280, (3), 775-93; Aldana-Masangkay, G. I. et al., *J Biomed Biotechnol* 2011, 875824). Recent studies also suggest HDAC6 regulates acetylation of beta-catenin in CD133 signaling pathway which is known to be important for tumor stem cell maintenance (Mak, A. B. et al., *Cell Rep* 2012, 2, (4), 951-63).

HDAC6 has also been linked to cell survival pathways through several different mechanisms. HDAC6 regulates reversible acetylation of Hsp90 chaperon whose client proteins include steroid hormone receptors and a number of protein kinases critical for cell proliferation and apoptosis. Inactivation of HDAC6 perturbs the chaperon activity of Hsp90 and attenuates the activity of growth promoting client proteins (Aldana-Masangkay, G. I. et al., *J Biomed Biotechnol* 2011, 875824). Through its ubiquitin binding domain, HDAC6 can bind polyubiquitinated misfolded proteins and deliver them to the dynein motor proteins for transport into aggresomes for degradation by lysosomes (Kawaguchi, Y. et al., Cell 2003, 115, (6), 727-38). HDAC6 also plays a role in the eventual clearance of aggresomes by promoting fusion of autophagosome with lysosomes (Lee, J. Y. et al., EMBO J 2010, 29, (5), 969-80; Iwata, A. et al., J Biol Chem 2005, 280, (48), 40282-92; Pandey, U. B. et al., Nature 2007, 447, (7146), 859-63).

Selective inhibition of HDAC6 can enhance apoptotic response to DNA damaging agents such as etoposide and doxorubicin (Namdar, M. et al., Proc Natl Acad Sci USA 2010, 107, (46), 20003-8). Conversely there is also evidence supporting a role of inhibition of HDAC6 in protecting normal cells from DNA-damage induced cell death and promote neuron regeneration (Rivieccio, M. A. et al., Proc Natl Acad Sci USA 2009, 106, (46), 19599-604). Thus, inhibition of HDAC6 may dramatically improve therapeutic index of cytotoxic agents.

HDAC6 is a target for protection and regeneration following injury in the nervous system. Injury of neurons leads to an increase in HDAC6 expression and inhibition of HDAC6 can promote survival and regeneration of neurons. Importantly, selective inhibition of HDAC6 avoids cell death associated with non-selective HDAC inhibitors (pan-HDAC inhibitors). Therefore HDAC6 may be promising target for the treatment of, for example, stroke, ischemia and spinal cord injury (Rivieccio, M. A. et al., Proc Natl Acad Sci USA 2009, 106, (46), 19599-604).

It is advantageous to have a selective HDAC6 inhibitor that inhibits HDAC6 with greater potency than other HDACs with no unwanted side effects (Bradner et al., Nat. Chem. Biol., 2010, 6(3):238-243; WO-A2011/019393).

In view of the importance of inhibiting only those HDAC isoforms relevant to a disease state, minimizing acetylation of proteins not related to the disease, and reducing side effects and toxicity, new HDAC inhibitors that are selective for specific HDACs are needed.

TTK/Mps1, a dual specificity protein kinase, has emerged as a master regulator of mitosis. In agreement with its proposed function in highly proliferative cells, elevated level of TTK/Mps1 is found in a variety of human cancer cell lines and primary tumor tissues. Like many cell cycle regulators, Mps1 transcription is deregulated in a variety of human tumors. Elevated Mps1 mRNA levels are found in several human cancers, including thyroid papillary carcinoma, breast cancer, gastric cancer tissue, bronchogenic carcinoma, and lung cancers (Mills, 1992 #187; Salvatore, 2007 #209; Yuan, 2006 #216; Kilpinen, 2010 #197; Daniel, 2010 #49; Landi, 2008 #217). Furthermore, high levels of Mps1 correlate with high histological grade in breast cancers (Daniel, 2010 #49). Conversely, Mps1 mRNA is markedly reduced or absent in resting cells and in tissues with a low proliferative index (Hogg, 1994 #190). Thus, there is a correlation between elevated Mps1 levels and cell proliferation as well as tumor aggressiveness. Consistent with the notion that oncogenic signaling promotes Mps1 expression, the levels and activity of Mps1 are increased by 3 and 10 fold respectively in human melanoma cell lines containing B-Raf (V600E) mutant (Cui, 2008 #153). Inhibition of B-Raf or MEK1 reduces Mps1 expression (Borysova, 2008 #147; Cui, 2008 #153).

The observation that tumor cells frequently over express spindle checkpoint proteins is perplexing as the conventional wisdom would postulate that tumor cells would have a weakened checkpoint, contributing to chromosome mis-segregation and aneuploidy. Indeed, significant evidence from yeast to mice supports the notion that a weakened checkpoint leads to chromosome instability (Weaver, 2005 #218). However, mutations in key checkpoint proteins are rare in human tumors, and correlative evidence showing that compromised checkpoint signaling directly contributes to the development of human tumors has been elusive. MPS1 missense mutations have been found in the noncatalytic, N-terminus in bladder (Olesen, 2001 #380) and lung cancers (Nakagawa, 2008 #406), and in the kinase domain in pancreatic (Carter, 2010 #384) and lung cancers (Nakagawa, 2008 #406). Interestingly, frameshift mutations that truncate the protein arise from microsatellite instability in the hMps1 gene in gastric (Ahn, 2009 #383) and colorectal cancers (Niittymaki, 2011 #382). Thus, mutations in hMPS1 have been detected in tumor-derived cells; however, their influence on tumorigenesis is not known.

The prevalence of high levels of checkpoint protein expression, such as Mps1, in human tumors prompts an alternative hypothesis regarding the potential role of checkpoint proteins in cancer cells, i.e. overexpression of these proteins may promote either cancer initiation or survival of aneuploid cancer cells (Sotillo, 2007 #219; Daniel, 2010 #49). Accordingly, reductions in key checkpoint proteins should severely decrease human cancer cell viability. This prediction is confirmed for several checkpoint proteins, including Mps1 (Fisk, 2003 #118; Daniel, 2010 #49), BubRI (Janssen, 2009 #173) and Mad2 (Kops, 2004 #220; Michel, 2004 #221). Suppression of Mps1 expression in Hs578T breast cancer cells also reduces the tumorigenicity of these cells in xenografts. The cancer cell death is likely due to severe chromosome segregation errors when the checkpoint is disabled. Interestingly, cells that survived reduced Mps1 levels often display lower levels of aneuploidy, suggesting that lower levels of Mps1 potentially inactivating the checkpoint are incompatible with aneuploidy (Daniel, 2010 #49). This concept is in excellent agreement with the observation that reduction in checkpoint proteins makes tumor cells more sensitive than untransformed human fibroblast to low doses of spindle poisons (Janssen, 2009 #173). Differential cellular responses to checkpoint inhibition between normal and tumor cells could be key in developing potential new anticancer drugs targeting hMps1.

Since different tumors have different levels of TTK expression, cancers that are most likely benefit from anti-TTK therapy are those tumors that express very high levels of TTK/Mps1. There is a need for effective methods for identification of cancerous cells by detection of expression levels of TTK/Mps1 in tumor biopsy. Reinhard et al from Chrion Corporation filed a US Patent in 2005 (US 20050058627) claims TTK can be used a tumor diagnostic marker and as a therapeutic target for cancer therapeutics.

Several TTK/Mps1 inhibitors have been described in the literature and patents. This list includes SP600125 ($IC_{50}$=250 nM), 2-Anilinopurin-8-ONES (AZ3146, $IC_{50}$=35 nM), Mps1-IN-1 ($IC_{50}$=370 nM), reversine ($IC_{50}$=3 nM), NMS-P715 ($IC_{50}$=8 nM) and MPI-0479605 ($IC_{50}$=3.5 nM). NMS-P715 has been tested in an ovarian xenograft and reported promising efficacies. Overall the TTK/Mps1 inhibitor development is still in a very early preclinical stage. Despite of availability of different small molecule chemotypes of Mps1 inhibitors (Reviewed in Liu and Winey, Annual Review of Biochemistry 2012), a fundamental question that has been addressed is that whether Mps1 inhibitors as singular agent can be effective in cancer therapeutics. First of all the therapeutic index of Mps1 inhibitor is rather narrow which is consistent with the essential function of Mps1 in both normal and cancer cell proliferation. Consistent with this notion, animal xenograft studies clearly indicates that Mps1 inhibition exhibited significant neutropenia and animal toxicity (body weight loss and death) (Brandi Williams, Molecular Cancer Therapeutics Paper 2011, Mol Cancer Ther. 2011 December; 10(12):2267-75. doi: 10.1158/1535-7163.MCT-11-0453. Epub 2011 Oct. 6). The current studies clearly revealed that using Mps1 inhibitor as singular agent clearly has its limitation in cancer therapeutics. New concepts, methodology and target agents are sorely needed to overcome these barriers to successful cancer therapeutics.

During the inventors' investigation of Mps1 biology, they discovered that histone deacetylase inhibitors (HDACi) have unexpected regulatory effects on Mps1 function. Specifically they discovered that HDAC inhibitors increase the therapeutic index of Mps1 inhibitors and hypothesized that HDAC inhibitors prevent normal cells but not cancer cells to enter mitosis. In doing so the effects of Mps1 inhibition will only manifest in tumor cells as normal cells stall prior to entrant into mitosis in the presence of HDACi. Another mechanism is that HDAC6 inhibition perturbs the pathway that is essential for Mps1 kinase activation. It is well established that HDAC6-HSP90 signaling axis is required for maturation of active Mps1. Inhibition of HDAC6 exacerbates the effects of Mps1 inhibitor. Here we demonstrate that combination of an HDAC inhibitor with a Mps1 inhibitor results in robust tumor inhibition and minimal cytotoxicity. In addition, dual inhibitors that combine HDAC inhibitory activity with Mps1 inhibitory active is highly effective in tumor growth inhibition in vivo.

The present invention describes new selective inhibitors of HDAC6 and/or TTK/Mps1 Kinase.

SUMMARY OF THE INVENTION

The present invention provides novel hydroxamic acids, which are specific histone deacetylase (HDAC) inhibitors, including pharmaceutically acceptable salts, which are useful for modulating HDAC activity for modulating cellular activities such as signal transduction, cell proliferation, cell survival and cytokine secretion. More specifically, the invention relates to hydroxamate compounds which inhibit, regulate and/or modulate HDAC activity, in particular HDAC6 activity, and signal transduction pathways relating to cellular activities as mentioned above. The present invention also provides novel compounds which are TTK/Mps1 Kinase inhibitors, including pharmaceutically acceptable salts, which are useful for modulating TTK/Mps1 Kinase activity for modulating cellular activities such as signal transduction, cell proliferation, cell survival and cytokine secretion.

The present invention also provides compounds which are capable of inhibiting both HDAC6 activity and TTK/Mps1 Kinase activity, either simultaneously or in a mutually exclusive manner, and are useful as therapeutics.

An aspect of the invention is a compound of formula (I):

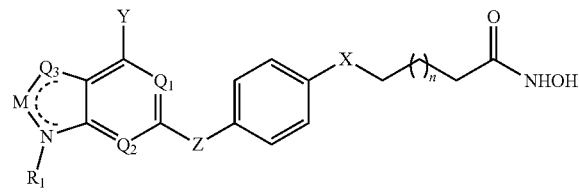

(I)

or a pharmaceutically acceptable salt thereof, wherein:
Z is NH or $CH_2$;
X is O, S, SO, $SO_2$, CO, $CR_2R_3$, $NR_4$, $SO_2NR_4$, $NR_4SO_2$, $CONR_4$, $NR_4CO$, $NR_4CO_2$, $NR_4(CO)NR_5$ or a bond;
M is $CR_6$ or N;
$Q_1$ and $Q_2$ are independently N or CH;
$Q_3$ is $CR_7$ or $Q_3$ is $NR_8$ when $R_1$ is not present;
n is 0-6;
Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_9$, $NR_{10}COR_9$, $NR_{10}CO_2R_9$, $CONR_{10}R_{11}$, $CO_2NR_{10}R_{11}$, $NR_{10}(CO)NR_{11}$, each of which may be optionally substituted and where $R_{10}$ and $R_{11}$ taken together may form a heterocyclic ring which may be optionally substituted;
$R_1$ is H, $C_1$-$C_6$ alkyl, haloalkyl, aryl, aryl-alkyl, heteroaryl, heteroaryl-alkyl, heterocyclic, carbocyclic or absent, each of which may be optionally substituted;
$R_2$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted;
$R_3$ is H, $C_1$-$C_6$ alkyl, alkoxy, aryl, $(CH_2)_n$-aryl, heteroaryl, $(CH_2)_n$-heteroaryl, cycloalkyl or heterocyclic, any of which is substituted or unsubstituted;
$R_4$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_5$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_6$ is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_9$, $NR_{10}COR_9$, $NR_{10}CO_2R_9$, $CONR_{10}R_{11}$, $CO_2NR_{10}R_{11}$ or absent, where $R_{10}$ and $R_{11}$ taken together may form a 4-7 membered ring which may be optionally substituted;
$R_7$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_8$ is H, $C_1$-$C_6$ alkyl, haloalkyl, aryl, aryl-alkyl, heteroaryl, heteroaryl-alkyl, heterocyclic, carbocyclic or absent, each of which may be optionally substituted;
$R_9$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_{10}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and
$R_{11}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted.

An exemplary embodiment of the invention is a compound of formula (I) wherein Y is $NR_{10}R_{11}$; $R_{10}$ is alkyl, aryl, heteroaryl, aryl-alkyl or heteroaryl-alkyl; and $R_{11}$ is alkyl or H, and where $R_3$ and $R_4$ taken together may form a 4-7 membered ring which is optionally substituted.

An exemplary embodiment of the invention is a compound of formula (I) wherein X is O, S, $SO_2$, $SO_2NR_4$ or $CONR_4$.

An exemplary embodiment of the invention is a compound of formula (I) wherein n is 2, 3, 4 or 5.

An exemplary embodiment of the invention is a compound of formula (I) wherein $R_1$ is H or $C_1$-$C_6$ alkyl; $Q_3$ is $NR_8$ where $R_8$ is absent; and M is $CR_6$ where $R_6$ is H.

An exemplary embodiment of the invention is a compound of formula (I) wherein $R_1$ is H or $C_1$-$C_6$ alkyl; $Q_3$ is $CR_7$ where $R_7$ is H; and M is N.

An exemplary embodiment of the invention is a compound of formula (I) wherein Y is aryl, heteroaryl or $NR_{10}R_{11}$.

Another aspect of the invention is a compound of formula (II):

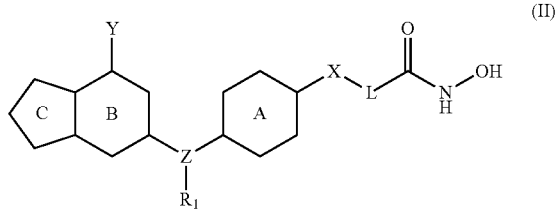

or a pharmaceutically acceptable salt, ester or prodrug thereof, wherein:

Ring A is an optionally substituted aryl or optionally substituted heteroaryl;

Ring B is an optionally substituted aryl or optionally substituted heteroaryl;

Ring C is an optionally substituted heteroaryl, optionally substituted cycloalkyl or optionally substituted heterocycloalkyl;

Z is N, $CR_2$, O, S, C=O, SO or $SO_2$;

$R_1$ is H, absent, $C_1$-$C_6$ alkyl, haloalkyl, hydroxyalkyl, carboxyalkyl, aryl, aryl-alkyl, heteroaryl, heterocyclic or carbocyclic, each of which may be optionally substituted, and wherein when Z is $CR_2$, $R_1$ and $R_2$ taken together may form a 3-7 membered ring which may be optionally substituted;

X is O, S, SO, $SO_2$, CO, $CR_2R_3$, $NR_4$, $SO_2NR_4$, $NR_4SO_2$, $CONR_4$, $NR_4CO$, $NR_4CO_2$, $NR_4(CO)NR_5$ or a bond;

Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_3$, $SR_3$, $COR_3$, $COOR_3$, $SOR_3$, $SO_2R_3$, $SO_2NR_4R_5$, $NR_4R_5$, $NR_4SO_2R_3$, $NR_4COR_3$, $NR_4CO_2R_3$, $CONR_4R_5$, $CO_2NR_4R_5$, $NR_4(CO)NR_5$ or absent, each of which may be optionally substituted and where $R_4$ and $R_5$ taken together may form a 4-7 membered ring which may be optionally substituted;

L is $C_1$-$C_9$ alkylene, $C_2$-$C_9$ alkenylene or $C_2$-$C_9$ alkynylene, any of which is substituted or unsubstituted, wherein one or more of the carbon atoms of the alkylene, alkenylene or alkynylene is optionally replaced with O, S, SO, $SO_2$, $SO_2NR_4$, $NR_4SO_2$, $NR_4$, CO, $CONR_4$, $NR_4CO$, $CO_2NR_4$, $NR_4CO_2$, $NR_4(CO)NR_5$, a cycloalkyl or a heterocycle, with the proviso that heteroatoms are not bonded directly to alkenyl or alkynyl carbons, and that the carbon atom adjacent to X shall not be optionally replaced such that a heteroatom-heteroatom bond results;

$R_2$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted;

$R_3$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_4$ is H, $C_1$-$C_6$ alkyl, aryl, $(CH_2)_n$-aryl, heteroaryl, $(CH_2)_n$-heteroaryl, cycloalkyl or heterocycle, any of which is substituted or unsubstituted;

$R_5$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and n is 1-4.

An exemplary embodiment of the invention is a compound of formula (II) or a pharmaceutically acceptable salt thereof, wherein ring A is phenyl, pyridinyl, pyrimidinyl or pyrazinyl.

An exemplary embodiment of the invention is compound of formula (II) or a pharmaceutically acceptable salt thereof, wherein ring B is phenyl, pyridinyl, pyrimidinyl or pyrazinyl.

An exemplary embodiment of the invention is compound of formula (II) or a pharmaceutically acceptable salt thereof, wherein ring C is independently selected from a 5-membered heteroaryl or a 5-membered heterocycloalkyl.

An exemplary embodiment of the invention is compound according to formula (II) or a pharmaceutically acceptable salt thereof, wherein Y is aryl, heteroaryl, $(CH_2)_n$-aryl, $(CH_2)_n$-heteroaryl, $NH_2$, NH(alkyl), N(alkyl)(alkyl), N(aryl)(alkyl), NH(cycloalkyl), N(alkyl)(cycloalkyl), NH(heteroaryl), NH(heterocycle), N(alkyl)(heteroaryl), N(alkyl)(heterocycle), NH(alkylheteroaryl), NH(alkylheterocycle), N(alkyl)(alkyl heteroaryl) or N(alkyl)(alkylheterocycle).

Another aspect of the invention is a compound of formula (III):

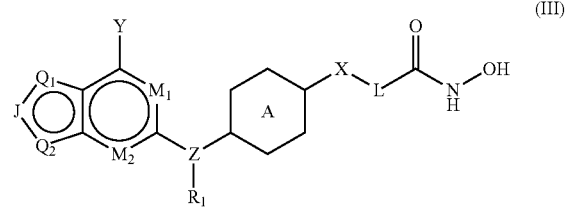

or a pharmaceutically acceptable salt thereof, wherein:

$Z_1$ is N or $CR_2$;

$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted, wherein, when Z is $CR_2$, $R_1$ and $R_2$ taken together may form a 3-7 membered ring which may be optionally substituted;

Ring A is an optionally substituted phenyl, pyridinyl, pyrimidinyl, or pyrazinyl;

$M_1$ and $M_2$ are independently N or $CR_3$;

$Q_1$ is $CR_4$, $NR_5$, O or S;

$Q_2$ is $CR_4$, $NR_5$, O or S;

J is N or $CR_6$;

X is O, S, SO, $SO_2$, CO, $CR_7R_8$, $NR_9$, $SO_2NR_9$, $NR_9SO_2$, $CONR_9$, $NR_9CO$, $NR_9CO_2$, $NR_9(CO)NR_{10}$ or a bond;

Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_8$, $SR_8$, $COR_8$, $COOR_8$, $SOR_8$, $SO_2R_8$, $SO_2NR_9R_{10}$, $NR_9R_{10}$, $NR_9SO_2R_8$, $NR_9COR_8$, $NR_9CO_2R_8$, $CONR_9R_{10}$, $CO_2NR_9R_{10}$, or $NR_9(CO)NR_{10}$, each of which may be optionally substituted and where $R_9$ and $R_{10}$ taken together may form a heterocyclic ring which may be optionally substituted;

L is $C_1$-$C_9$ alkylene, $C_2$-$C_9$ alkenylene or $C_2$-$C_9$ alkynylene, any of which is substituted or unsubstituted, wherein one or more of the carbon atoms of the alkylene, alkenylene or alkynylene is optionally replaced with O, S, SO, $SO_2$, $SR_8$, $SO_2NR_9$, $NR_9SO_2$, $NR_9$, CO, $CONR_9$, $NR_9CO$, $CO_2NR_9$, $NR_9CO_2$, a cycloalkyl or a heterocycle, with the proviso that heteroatoms are not bonded directly to alkenyl or alkynyl carbons, and that the carbon adjacent to X shall not be optionally replaced such that a heteroatom-heteroatom bond results;

$R_2$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted;

$R_3$ is H, CN, Cl, Br, I, F, $C_1$-$C_6$ alkyl, haloalkyl, cycloalkyl, heterocycloalkyl, aryl, heteroaryl, $OR_8$, $SR_8$, $COR_8$, $COOR_8$, $SOR_8$, $SO_2R_8$, $SO_2NR_9R_{10}$, $NR_9R_{10}$, $NR_9SO_2R_8$, $NR_9COR_8$, $NR_9CO_2R_8$, $CONR_9R_{10}$, $CO_2NR_9R_{10}$ or $NR_9(CO)NR_{10}$, each of which may be optionally substituted and where $R_9$ and $R_{10}$ taken together may form a heterocyclic ring which may be optionally substituted;

$R_4$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted;

$R_5$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted;

$R_6$ is H, CN, Cl, Br, I, F, $C_1$-$C_6$ alkyl, haloalkyl, cycloalkyl, heterocycloalkyl, aryl, heteroaryl, $OR_8$, $SR_8$, $COR_8$, $COOR_8$, $SOR_8$, $SO_2R_8$, $SO_2NR_9R_{10}$, $NR_9R_{10}$, $NR_9SO_2R_8$, $NR_9COR_8$, $NR_9CO_2R_8$, $CONR_9R_{10}$, $CO_2NR_9R_{10}$ or $NR_9(CO)NR_{10}$, each of which may be optionally substituted and where $R_9$ and $R_{10}$ taken together may form a heterocyclic ring which may be optionally substituted;

$R_7$ is H, $C_1$-$C_6$ alkyl, alkoxy, aryl, $(CH_2)_n$-aryl, heteroaryl, $(CH_2)_n$-heteroaryl, cycloalkyl or heterocyclic, any of which is substituted or unsubstituted;

$R_8$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_9$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_{10}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and n is 1-4.

An exemplary embodiment of the invention is a compound according to formula (III), wherein Z is nitrogen and $R_1$ is H.

An exemplary embodiment of the invention is a compound according to formula (III), wherein X and Z are oriented para to each other.

An exemplary embodiment of the invention is a compound according to formula (III) or a pharmaceutically acceptable salt thereof, wherein Y is aryl, heteroaryl, alkylaryl, alkyl-heteroaryl, $NH_2$, NH(alkyl), N(alkyl)(alkyl), N(aryl)(alkyl), NH(cycloalkyl), N(alkyl)(cycloalkyl), NH(heteroaryl), NH(heterocycle), N(alkyl)(heteroaryl), N(alkyl)(heterocycle), NH(alkylheteroaryl), NH(alkylheterocycle), N(alkyl)(alkylheteroaryl) or N(alkyl)(alkylheterocycle).

An exemplary embodiment of the invention is a compound according to formula (III), wherein $M_1$ and $M_2$ are independently N or $CR_3$, where $R_3$ is H.

An exemplary embodiment of the invention is a compound according to formula (III), wherein $Q_1$ is $NR_5$; $Q_2$ is $NR_7$; and J is $CR_6$, where $R_5$ is absent and $R_7$ is H or alkyl.

An exemplary embodiment of the invention is a compound according to formula (III), wherein $Q_1$ is $NR_5$; $Q_2$ is $NR_7$; and J is $CR_6$, where $R_5$ is alkyl and $R_7$ is absent.

Another aspect of the invention is a compound of formula (IV):

(IV)

or a pharmaceutically acceptable salt thereof, wherein:

Z is N or $CR_3$;

$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted, wherein, when Z is $CR_3$, $R_1$ and $R_3$ taken together may form a 3-7 membered ring which may be optionally substituted;

$R_2$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted;

$R_3$ is H, $C_1$-$C_6$ alkyl, hydroxy, alkoxy, aryl, $(CH_2)_q$-aryl, heteroaryl, $(CH_2)_q$-heteroaryl, cycloalkyl or heterocyclic, any of which is substituted or unsubstituted, where $R_1$ and $R_3$ taken together may form a 3-7 membered ring which may be optionally substituted;

each of $Q_1$, $Q_2$, $Q_3$ and $Q_4$ is independently N or $CR_4$;

Ring B is an optionally substituted phenyl, pyridinyl, pyrimidinyl or pyrazinyl;

Ring C is an optionally substituted heteroaryl, optionally substituted cycloalkyl or optionally substituted heterocycloalkyl;

X is O, S, SO, $SO_2$, CO, $CR_5R_6$, $NR_7$, $SO_2NR_7$, $NR_7SO_2$, $CONR_7$, $NR_7CO$, $NR_7CO_2$, $NR_7(CO)NR_8$ or a bond, wherein, $R_5$ and $R_6$ taken together may form a 3-7 membered ring which may be optionally substituted;

Y is H, CN, Cl, Br, I, F, $C_1$-$C_6$ alkyl, haloalkyl, cycloalkyl, heterocycloalkyl, aryl, heteroaryl, $(CH_2)_q$-aryl, $(CH_2)_q$-heteroaryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_7$, $CONR_7R_8$, $CO_2NR_7R_8$, $NR_7(CO)NR_8$, or absent, each of which may be optionally substituted and where $R_7$ and $R_8$ taken together may form a heterocyclic ring which may be optionally substituted;

n is 1-5 and m is 1-5 when X is $CR_5R_6$;

n is 2-4 and m is 1-4 when X is other than $CR_5R_6$;

q is 2-4;

$R_4$ is H, CN, Cl, Br, I, F, alkyl, haloalkyl, cycloalkyl, heterocycloalkyl, aryl, heteroaryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_6$, $CONR_7R_8$, $CO_2NR_7R_8$ or $NR_7(CO)NR_8$, each of which may be optionally substituted and where $R_7$ and $R_8$ taken together may form a heterocyclic ring which may be optionally substituted;

$R_5$ is H, $C_1$-$C_6$ alkyl, alkoxy, aryl, $(CH_2)_q$-aryl, heteroaryl, $(CH_2)_q$-heteroaryl, cycloalkyl or heterocyclic, any of which is substituted or unsubstituted;

$R_6$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted;

$R_7$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted;

$R_8$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted.

An exemplary embodiment of the invention is a compound of formula (IV), wherein rings B and C taken together form a purine, pyrazolopyrimidine, pyrazolopyridine, pyrrolopyrimidine, thiazolopyrimidine, purinone, indole, pyrrolopyrimidinone or dihydropyrrolopyrimidine.

An exemplary embodiment of the invention is a compound of formula (IV), wherein $Q_1$ and $Q_3$ are N; and $Q_2$ and $Q_4$ are $CR_4$ where $R_4$ is H.

An exemplary embodiment of the invention is a compound of formula (IV), wherein $Q_1$ and $Q_3$ are $CR_4$ where $R_4$ is H; and $Q_2$ and $Q_4$ are N.

An exemplary embodiment of the invention is a compound of formula (IV), wherein $Q_1$, $Q_2$, $Q_3$ and $Q_4$ are $CR_4$ where $R_4$ is H.

An exemplary embodiment of the invention is a compound of formula (IV), wherein Z is N; and $R_1$ is H.

An exemplary embodiment of the invention is a compound of formula (IV), wherein X is O, $(CO)NR_8$ or $S(O)_2NR_8$; and $R_8$ is H, alkyl, aryl, heteroaryl, cycloalkyl or heterocyclic, any of which is substituted or unsubstituted.

An exemplary embodiment of the invention is a compound of formula (IV), wherein n is 3; m is 1; and $R_2$ is H or alkyl.

Another aspect of the invention is a compound of formula (V):

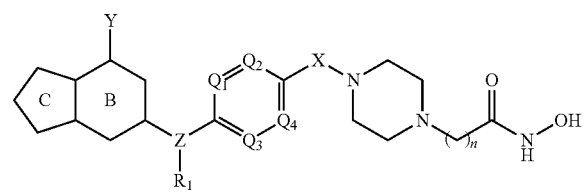

(V)

or a pharmaceutically acceptable salt thereof, wherein:
Z is N or $CR_2$;
$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted;
each of $Q_1$, $Q_2$, $Q_3$, and $Q_4$ is independently N or $CR_3$;
Ring B is an optionally substituted phenyl, pyridinyl, pyrimidinyl or pyrazinyl;
Ring C is an optionally substituted heteroaryl, optionally substituted cycloalkyl or optionally substituted heterocycloalkyl;
$R_2$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted, where $R_1$ and $R_3$ taken together may form a 3-7 membered ring which may be optionally substituted;
X is $(CR_4R_5)_n$, $SO_2$, CO, $NR_6CO$ or absent;
Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, aryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_6$, $CONR_7R_8$, $CO_2NR_7R_8$ or absent, and where $R_7$ and $R_8$ taken together may form a 4-7 membered ring which may be optionally substituted;
n=1-4;
$R_3$ is H, CN, Cl, Br, I, F, $C_1$-$C_6$ alkyl, haloalkyl, cycloalkyl, heterocycloalkyl, aryl, heteroaryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_6$, $CONR_7R_8$, $CO_2NR_7R_8$ or $NR_7(CO)NR_8$, each of which may be optionally substituted and where $R_7$ and $R_8$ taken together may form a heterocyclic ring which may be optionally substituted;
$R_4$ is H, $C_1$-$C_6$ alkyl, aryl, heteroaryl, cycloalkyl or heterocyclic, any of which is substituted or unsubstituted;
$R_5$ is H, $C_1$-$C_6$ alkyl, aryl, heteroaryl, cycloalkyl or heterocyclic, any of which is substituted or unsubstituted;
$R_6$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_7$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and
$R_8$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted.

An exemplary embodiment of the invention is a compound of formula (V), wherein rings B and C taken together form a purine, pyrazolopyrimidine, pyrazolopyridine, pyrrolopyrimidine, thiazolopyrimidine, purinone, indole, pyrrolopyrimidinone or dihydropyrrolopyrimidine.

An exemplary embodiment of the invention is a compound of formula (V), wherein Z is N, and $R_1$ is H.

An exemplary embodiment of the invention is a compound of formula (V), wherein $Q_1$, $Q_2$, $Q_3$ and $Q_4$ are $CR_3$ where $R_3$ is H.

An exemplary embodiment of the invention is a compound of formula (V), wherein X is $CR_4R_5$, $SO_2$, CO, $NR_4CO$ or absent.

An exemplary embodiment of the invention is a compound of formula (V), wherein Y is aryl, heteroaryl, $(CH_2)_n$-aryl, $(CH_2)_n$-heteroaryl or $NR_7R_8$.

Another aspect of the invention is a compound of formula (VI):

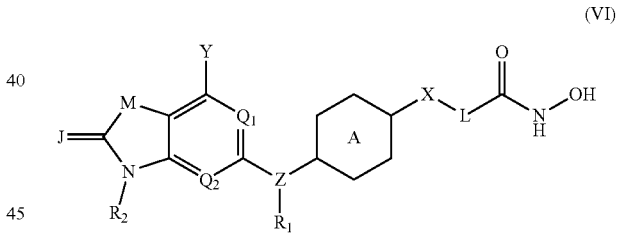

(VI)

or a pharmaceutically acceptable salt, ester or prodrug thereof, wherein:
Ring A is an optionally substituted aryl or optionally substituted heteroaryl;
Z is N or $CR_3$;
$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted;
$R_2$ is an optionally substituted $C_1$-$C_6$ alkyl, acyl, aryl or heteroaryl;
$Q_1$ and $Q_2$ are independently N or $CR_4$;
M is $NR_5$, $CR_6R_7$, O or S;
J is O, S or absent;
X is O, S, SO, $SO_2$, CO, $CR_8R_9$, $NR_{10}$, $SO_2NR_{10}$, $NR_{10}SO_2$, $CONR_{10}$, $NR_9CO$, $NR_{10}CO_2$, $NR_{10}(CO)NR_{11}$ or absent;
Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_9$, $NR_{10}COR_9$, $NR_{10}CO_2R_9$, $CONR_{10}R_{11}$, $CO_2NR_{10}R_{11}$ or absent, where $R_{10}$ and $R_{11}$ taken together may form a 4-7 membered ring which may be optionally substituted;

L is $C_1$-$C_9$ alkylene, $C_2$-$C_9$ alkenylene or $C_2$-$C_9$ alkynylene, any of which is substituted or unsubstituted, wherein one or more of the carbon atoms of the alkylene, alkenylene or alkynylene is optionally replaced with O, S, SO, $SO_2$, $SO_2NR_{10}$, $NR_{10}SO_2$, $NR_{10}$, CO, $CONR_{10}$, $NR_{10}CO$, $CO_2NR_{10}$, $NR_{10}CO_2$, cycloalkyl or heterocyclic, with the proviso that heteroatoms are not bonded directly to alkenyl or alkynyl carbons, and that the carbon adjacent to X shall not be optionally replaced such that a heteroatom-heteroatom bond results;

$R_3$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted, where $R_1$ and $R_3$ taken together may form a 3-7 membered ring which may be optionally substituted;

$R_4$ is H, CN, Cl, Br, I, F, $C_1$-$C_6$ alkyl, haloalkyl, cycloalkyl, heterocycloalkyl, aryl, heteroaryl $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_{11}$, $NR_{10}COR_9$, $NR_{10}CO_2R_9$, $CONR_{10}R_{11}$ or $CO_2NR_{10}R_{11}$, where $R_{10}$ and $R_{11}$ taken together may form a 4-7 membered ring which may be optionally substituted;

$R_5$ is an optionally substituted $C_1$-$C_6$ alkyl, acyl, aryl or heteroaryl;

$R_6$ is H, $C_1$-$C_6$ alkyl, hydroxy, alkoxy, aryl, $(CH_2)_n$-aryl, heteroaryl, $(CH_2)_n$-heteroaryl, cycloalkyl or heterocycle;

$R_7$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted, where $R_6$ and $R_7$ taken together may form a 3-7 membered ring which may be optionally substituted;

$R_8$ is H, $C_1$-$C_6$ alkyl, alkoxy, aryl, $(CH_2)_n$-aryl, heteroaryl, $(CH_2)_n$-heteroaryl, cycloalkyl or heterocycle, any of which is substituted or unsubstituted;

$R_9$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_{10}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_{11}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and n is 1-4.

An exemplary embodiment of the invention is a compound of formula (VI), wherein Z is N; and $R_1$ is H.

An exemplary embodiment of the invention is a compound of formula (VI), wherein $Q_1$ and $Q_2$ are independently N or $CR_4$ where $R_4$ is H.

An exemplary embodiment of the invention is a compound of formula (VI), wherein M is $CR_6R_7$ where $R_6$ and $R_7$ are alkyl, or taken together form a 3, 4, or 5 membered ring.

An exemplary embodiment of the invention is a compound of formula (VI), wherein Ring A is phenyl.

An exemplary embodiment of the invention is a compound of formula (VI), wherein X and Z are oriented para to each other.

An exemplary embodiment of the invention is a compound of formula (VI), wherein X is O, $CR_8R_9$ or $CONR_{10}$.

An exemplary embodiment of the invention is a compound of formula (VI), wherein J is O or absent.

An exemplary embodiment of the invention is a compound of formula (VI), wherein Y is aryl, heteroaryl, $(CH_2)_n$-aryl, $(CH_2)_n$-heteroaryl or $NR_7R_8$.

An exemplary embodiment of the invention is a compound of formula (VI), wherein L is $C_3$-$C_8$ alkylene.

In an exemplary embodiment, the invention provides compounds, such as those selected from formulae (I) through (VI), that are HDAC inhibitors which inhibit at least one HDAC isoform selected from the group consisting of HDAC1, HDAC2, HDAC3, HDAC4, HDAC5, HDAC6, HDAC7, HDAC8, HDAC9 and a combination thereof.

In another exemplary embodiment, the invention provides HDAC inhibitors, such as those selected from formulae (I) through (VI), that are selective to the HDAC6 isoform.

In another exemplary embodiment, the invention provides TTK/Mps1 kinase inhibitors, such as those selected from formulae (I) through (VI).

In another exemplary embodiment, the invention provides compounds, such as those selected from formulae (I) through (VI), that are inhibitors of both HDAC6 and TTK/Mps1 kinase.

In another exemplary embodiment, the invention provides the use of HDAC6 inhibitors and/or TTK/Mps1 kinase inhibitors, such as those selected from formulae (I) through (VI) in a method for treating or preventing an immunological, proliferative, inflammatory, autoimmune or allergic disorder or disease, or a transplant rejection, or a graft-versus host disease, or a neurodegenerative disease or neuron injury in a mammal, such as a human, by administering a therapeutically effective amount of the compound, either alone or co-administered with a known therapeutic agent.

In another exemplary embodiment, the invention provides pharmaceutical compositions of a compound such as those selected from formulae (I) through (VI), and/or the pharmaceutically acceptable salts of such compounds as described herein and including a pharmaceutically acceptable carrier or excipient.

In another exemplary embodiment, the invention provides pharmaceutical compositions of one or more compounds or pharmaceutically acceptable salts of one or more compounds described herein for use in a therapy to treat or prevent a disorder or disease such as the particular ones described herein.

In another exemplary embodiment, the invention provides pharmaceutical compositions of one or more compounds or pharmaceutically acceptable salts of one or more compounds described herein for use in treatment, prevention, or delay of cancer progression.

In another exemplary embodiment, the invention provides pharmaceutical compositions of compounds or pharmaceutically acceptable salts of one or more compounds described herein for use in the treatment, prevention, or delay of progression of a neurodegenerative disorder.

In another exemplary embodiment, the invention provides pharmaceutical compositions of compounds or pharmaceutically acceptable salts of one or more compounds described herein for use in the treatment, prevention, or delay of the progression of inflammation.

In another exemplary embodiment, the invention provides methods of treating diseases mediated by HDAC enzymes, comprising administering to a subject in need thereof a therapeutically effective amount of one or more of the compounds described herein, such as the compounds of formulae (I) through (VI). Other methods involve co-therapies by administering one or more compounds of the invention with other agents known to treat or prevent cancers, neurodegenerative disorders and inflammation.

In another exemplary embodiment, the invention provides methods for the treatment, prevention or delay of the progression of cancer, neurodegenerative disorder or inflammation in a subject, which comprise administering a therapeutically effective amount of a compound of the invention such as the compounds of formulae (I) through (VI) or a pharmaceutically acceptable salt thereof, or pharmaceutical compositions, further comprising combination therapies with other agents known to treat or prevent cancers, neurodegenerative disorders and inflammation.

DETAILED DESCRIPTION

Figure 1:
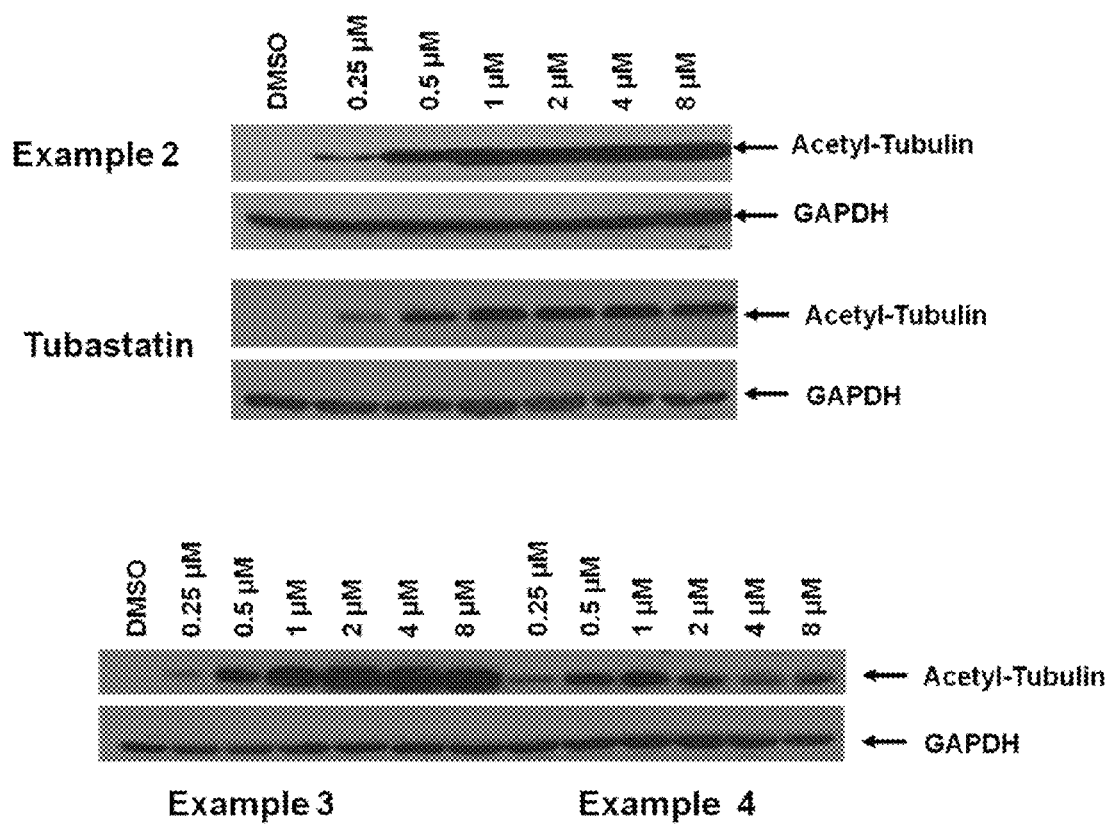
FIG. 1 illustrates the results of Tubulin acylation when treated with the compounds of Examples 2-4.

The following description is merely exemplary in nature and is not intended to limit the present disclosure, application, or uses of the compounds described herein.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

Definitions

As used herein, the singular forms "a", "an", and "the" include plural references, unless the content clearly dictates otherwise, and may be used interchangeably with "at least one" and "one or more."

Unless otherwise indicated, all numbers expressing quantities of ingredients, dimensions reaction conditions and so forth used in the specification and claims are to be understood as being modified in all instances by the term "about".

As used herein, the term "activity" refers to the activation, production, expression, synthesis, intercellular effect, and/or pathological or aberrant effect of the referenced molecule, either inside and/or outside of a cell.

As used herein, the terms "comprises", "comprising", "includes", "including", "contains", "containing" and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "histone deacetylase" or "HDAC" refers to any member of the classes of enzymes capable of cleaving an acetyl group (—C(═O)CH$_3$) from proteins, which includes, but are not limited to, histones and microtubules. A histone deacetylase may be zinc-dependent. Examples of HDACs include, but are not limited to, HDAC1, HDAC2, HDAC3, HDAC4, HDAC5, HDAC6, HDAC7, HDAC8, HDAC9, HDAC10 and HDAC11.

As used herein, use of "or" means "and/or" unless stated otherwise. Also, terms such as "element" or "component" encompass both elements and components comprising one unit and elements and components that comprise more than one unit unless specifically stated otherwise.

The term "pharmaceutically acceptable" or "pharmacologically acceptable" as used herein, refer to molecular entities and compositions that do not produce adverse, allergic, or other untoward reactions when administered to an animal or a human.

The term, "pharmaceutically acceptable carrier" as used herein, includes any and all solvents, or a dispersion medium including, but not limited to, water, ethanol, a polyol (for example, glycerol, propylene glycol, and liquid polyethylene glycol, and the like), suitable mixtures thereof, and vegetable oils, coatings, isotonic and absorption delaying agents, liposomes, commercially available cleansers, and the like. Supplementary bioactive ingredients also can be incorporated into such carriers.

The term "substituted" as used herein, means that at least one hydrogen atom of a molecular arrangement is replaced with a non-hydrogen substituent. For example, in the case of an oxo substituent ("═O"), two hydrogen atoms are replaced. When substituted, the replacing group is referred to as a "substituent." Substituents may include, but are not limited to, halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle, and heterocyclealkyl, as well as —NRaRb, —NRaC(═O)Rb, —NRaC(═O)NRaNRb, —NRaC(═O)ORb, —NRaSO$_2$Rb, —C(═O)Ra, —C(═O)ORa, —C(═O)NRaRb, —OC(═O)NRaRb, —OR, —SR, —SORa, —S(═O)aR, —OS(═O)$_2$Ra and —S(═O)ORa. In addition, the above substituents may be further substituted with one or more of the above substituents, such that the substituent comprises a substituted alkyl, substituted aryl, substituted arylalkyl, substituted heterocyclyl or substituted heterocycloalkyl. Ra and Rb in this context may be the same or different and typically include, but are not limited to, hydrogen, alkyl, haloalkyl, substituted alkyl, aryl, substituted aryl, arylalkyl, substituted arylalkyl, heterocyclyl, substituted heterocyclyl, heterocycloalkyl or substituted heterocycloalkyl.

The term "unsubstituted" as used herein, refers to any compound that does not contain extra substituents attached to the compound. An unsubstituted compound refers to the chemical makeup of the compound without extra substituents, e.g., the compound does not contain protecting group(s).

The term "alkyl", as used herein, means any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms, such as 6-10 carbon atoms. Representative saturated straight chain alkyls include, but are not limited to, methyl, ethyl, n-propyl, n-butyl, n-pentyl, n-hexyl, n-heptyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as "cycloalkyls", "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, refers to any aromatic carbocyclic moiety such as, but not limited to, phenyl or naphthyl.

The term "arylalkyl", or "aralkyl" as used herein, refers to any alkyl having at least one alkyl hydrogen atom replaced with an aryl moiety, such as benzyl, but not limited to, —(CH$_2$)$_2$phenyl, —(CH$_2$)$_3$phenyl, —CH(phenyl)$_2$, and the like.

The term "halogen" as used herein, refers to any fluoro, chloro, bromo, or iodo moiety.

The term "haloalkyl" as used herein, refers to any alkyl having at least one hydrogen atom replaced with halogen, such as trifluoromethyl, and the like.

The term "heteroaryl" as used herein, refers to any aromatic heterocycle ring of 5 to 10 members and having at least one heteroatom selected from nitrogen, oxygen and sulfur, and containing at least one carbon atom, including, but not limited to, both mono- and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl" as used herein, refers to any alkyl having at least one alkyl hydrogen atom replaced with a heteroaryl moiety, such as —CHpyridinyl, —CH$_2$pyrimidinyl, and the like.

The term "heterocycle" or "heterocyclic" or "heterocyclic ring", as used herein, refers to any 4- to 7-membered monocyclic or any 7- to 10-membered bicyclic heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include heteroaryls exemplified by those defined above. Thus, in addition to the heteroaryls listed above, heterocycles may also include, but are not limited to, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like.

The term "heterocycloalkyl", as used herein, refers to any alkyl having at least one alkyl hydrogen atom replaced with a heterocycle, such as —CH$_2$morpholinyl, and the like.

The term "homocycle" or "cycloalkyl", as used herein, refers to any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, refers to at least one alkyl moiety attached through a nitrogen bridge (i.e., —N-(alkyl)N, such as a dialkylamino) including, but not limited to, methylamino, ethylamino, dimethylamino, diethylamino, and the like.

The term "alkyloxy" or "alkoxy", as used herein, refers to any alkyl moiety attached through an oxygen bridge (i.e., —O-alkyl) such as, but not limited to, methoxy, ethoxy, and the like.

The term "alkylthio", as used herein, refers to any alkyl moiety attached through a sulfur bridge (i.e., —S— alkyl) such as, but not limited to, methylthio, ethylthio, and the like.

The term "alkenyl" refers to an unbranched or branched hydrocarbon chain having one or more double bonds therein. The double bond of an alkenyl group can be unconjugated or conjugated to another unsaturated group. Suitable alkenyl groups include, but are not limited to vinyl, allyl, butenyl, pentenyl, hexenyl, butadienyl, pentadienyl, hexadienyl, 2-ethylhexenyl, 2-propyl-2-butenyl,4-(2-methyl-3-butene)-pentenyl. An alkenyl group can be unsubstituted or substituted with one or two suitable substituents.

The term "alkynyl" refers to an unbranched or branched hydrocarbon chain having one or more triple bonds therein. The triple bond of an alkynyl group can be unconjugated or conjugated to another unsaturated group. Suitable alkynyl groups include, but are not limited to ethynyl, propynyl, butynyl, pentynyl, hexynyl, methylpropynyl, 4-methyl-1-butynyl, 4-propyl-2-pentynyl- and 4-butyl-2-hexynyl. An alkynyl group can be unsubstituted or substituted with one or two suitable substituents.

The terms "alkylene", "alkenylene" and "alkynylene" as used herein refer to a divalent alkane, alkene and alkyne radical, respectively. It is understood that the alkylene, alkenylene and alkynylene may be straight or branched. An alkylene, alkenylene and alkynylene may also be substituted and unsubstituted.

The term "salts" as used herein, refers to any salt that complexes with identified compounds described herein. Examples of such salts include, but are not limited to, acid addition salts formed with inorganic acids (e.g., hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known to a person skilled in the art, which specifically includes the quaternary ammonium salts of the formula —NRR'R"+Z—, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention, and/or their salts when salt formation is possible, but in particular, derivatives of zinc binding thiol moiety. Examples of prodrug moieties include substituted and unsubstituted, branched or unbranched lower alkyl ester moieties, (e.g., a propionic acid ester), lower alkenyl esters, di-lower alkyl-amino lower-alkyl esters (e.g., a dimethylaminoethyl ester), acylamino lower alkyl esters (e.g., an acetyloxymethyl ester), acyloxy lower alkyl esters (e.g., a pivaloyloxymethyl ester), aryl esters (e.g., a phenyl ester), aryl-lower alkyl esters (e.g., a benzyl ester), heteroaryl esters (e.g., a nicotinate ester), substituted (e.g., with methyl, halo, or methoxy substituents) aryl and aryl-lower alkyl esters, amides, lower-alkyl amides, di-lower alkyl amides, and hydroxy amides. Naturally occurring amino acid esters or their enantiomers, dipeptide esters, phosphate esters, methoxyphosphate esters, disulfides and disulfide dimers may also qualify as prodrugs. Prodrugs and their uses are well known in the art (see, e.g., Berge et al. 1977). Prodrugs can typically be prepared using well-known methods, such as those described in Burger's Medicinal Chemistry and Drug Discovery (Manfred E. Wolff ed. 1995) and (Rautio, 2008).

"Cancer" is a term used for diseases in which abnormal cells divide without control and are able to invade other tissues. There are more than 100 different types of cancer. Most cancers are named for the organ or type of cell in which they start—for example, cancer that begins in the colon is called colon cancer; cancer that begins in basal cells of the skin is called basal cell carcinoma. The main categories of cancer include carcinomas, sarcomas, leukemias, lymphomas and myelomas, and central nervous system cancers. Some common cancer types include, but are not limited to, bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer. In one embodiment, the cancers contemplated for treatment herein include colon and breast cancers.

"Neurodegenerative" disease or condition is a term used for a range of conditions which primarily affect the neurons in the human brain. Some common neurodegenerative diseases are Parkinson's disease, Alzheimer's disease and other dementias, motor neuron diseases, prion disease, Huntington's disease, Spinocerebellar ataxia and spinal muscular atrophy.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In various exemplary embodiments, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository, etc.

The term "patient", as used herein, is an animal, such as, for example, a mammal, such as, for example, a human that need not be hospitalized. For example, out-patients and persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "subject" as used herein refers to a vertebrate, preferably a mammal, more preferably a primate, still more preferably a human. Mammals include, without limitation, humans, primates, wild animals, feral animals, farm animals, sports animals and pets.

Exemplary Embodiments of the Invention

The present invention provides novel hydroxamic acids, which are specific histone deacetylase (HDAC) and/or TTK/Mps1 kinase inhibitors, including pharmaceutically acceptable salts, which are useful for modulating HDAC activity and/or TTK/Mps1 kinase activity, and therefore altering cellular activities such as signal transduction, cell proliferation, cell survival and cytokine secretion.

In an exemplary embodiment, the invention provides compounds selective to HDAC6 inhibition for the treatment and/or prevention of diseases such as immunological, inflammatory, autoimmune, allergic disorders, proliferative diseases such as cancer, neurodegenerative disorders or neurological diseases.

In an exemplary embodiment, the invention provides compounds selective to TTK/Mps1 kinase inhibition for the treatment and/or prevention of diseases such as immunological, inflammatory, autoimmune, allergic disorders, proliferative diseases such as cancer, neurodegenerative disorders or neurological diseases.

In an exemplary embodiment, the invention provides compounds capable of inhibiting both HDAC6 and TTK/Mps1 kinase either simultaneously or in a mutually exclusive manner for the treatment and/or prevention of diseases such as immunological, inflammatory, autoimmune, allergic disorders, proliferative diseases such as cancer, neurodegenerative disorders or neurological diseases.

In an exemplary embodiment, the invention provides a pharmaceutical composition comprising at least one pharmaceutically-acceptable carrier, in addition to one or more compounds described herein. The composition can be present in any suitable form for the desired route of administration. Where the composition is to be administered orally, any suitable orally deliverable dosage form can be used, including, without limitation, tablets, capsules (solid or liquid filled), powders, granules, syrups and other liquids, elixirs, inhalants, troches, lozenges and solutions. Injectable compositions or i.v. infusions are also provided in the form of solutions, suspensions, and emulsions.

In yet another exemplary embodiment, a pharmaceutical composition according to the invention may contain one or more additional therapeutic agents, for example, to increase the efficacy or decrease side effects. In some embodiments, a pharmaceutical composition further contains one or more additional therapeutic agents selected from active ingredients useful to treat or inhibit disease mediated directly or indirectly by HDAC6 and/or TTK/Mps1 kinase. Examples of such active ingredients are, without limitation, agents to treat or inhibit diseases such as immunological, inflammatory, autoimmune, allergic disorders, proliferative diseases such as cancer, neurodegenerative disorders or neurological diseases.

In another exemplary embodiment, an additional therapeutic agent is included with the treatment, such as an anti-cancer agent. Examples of an anti-cancer agent include, but are not limited to, alkylating agents such as cyclophosphamide, dacarbazine, and cisplatin; anti-metabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anti-cancer agents such as asparaginase, rituximab, trastuzumab, imatinib, retinoic acid and derivatives, colony stimulating factors, amifostine, camptothecin, topotecan, thalidomide analogs such as lenalidomide, CDK inhibitors, proteasome inhibitors such as Velcade and other HDAC inhibitors.

In particular exemplary embodiments, the target disease is rheumatoid arthritis, osteoarthritis; rheumatoid spondylitis; psoriasis; post ischemic perfusion injury; inflammatory bowel disease; chronic inflammatory pulmonary disease, eczema, asthma, psoriasis, ischemia/reperfusion injury, ulcerative colitis, acute respiratory distress syndrome, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis, glomerulonephritis, hemolytic anemia, aplastic anemia, idiopathic thrombocytopenia, neutropenia, ulcerative colitis, Crohn's disease, host versus graft disease, allograft rejection, chronic thyroiditis, Graves' disease, scleroderma, diabetes, active hepatitis, primary biliary cirrhosis, myasthenia gravis, multiple sclerosis, systemic lupus erythematosus, atopic dermatitis, contact dermatitis, chronic renal insufficiency, idiopathic sprue, sarcoidosis, Guillain-Barre syndrome, uveitis, conjunctivitis, keratoconjunctivitis, otitis media, periodontal disease, pulmonary interstitial fibrosis, asthma, bronchitis, rhinitis, sinusitis, pneumoconiosis, pulmonary insufficiency syndrome, pulmonary emphysema, pulmonary fibrosis, silicosis, or chronic inflammatory pulmonary disease.

In particular exemplary embodiments, the target disease is protein deposition disorders, Wilson's disease, spinocerebellar ataxia, prion disease, Parkinson's disease, Huntington's disease, amyotrophic lateral sclerosis, spinal muscular atrophy, spinal and bulbar muscular atrophy, amyloidosis, Alzheimer's disease, Alexander's disease, alcoholic liver disease, cystic fibrosis, Pick's disease, and Lewy body dementia. In particular embodiments, the compounds of the invention are useful for disorders associated with tubulin deacetylation activity.

In another exemplary embodiment, the invention provides a method of inhibiting or treating diseases arising from abnormal cell proliferation and/or differentiation in a subject in need thereof, comprising administering to the subject a therapeutically effective amount of one or more compounds according to the present invention. In one embodiment, the method of inhibiting or treating disease comprises administering to a subject in need thereof, a composition comprising an effective amount of one or more compounds of the invention and a pharmaceutically acceptable carrier. The composition to be administered may further contain a therapeutic agent such as anti-cancer agent or an agent to treat neurodegenerative diseases.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Exemplary Compounds of the Invention

The compounds of the invention are defined herein by their chemical structures and/or chemical names. The compounds of the invention are generally named according to the IUPAC or CAS nomenclature system. Abbreviations that are well known to one of ordinary skill in the art may be used. When a compound is referred to by both a chemical structure and a chemical name, and the chemical structure and chemical name conflict, the chemical structure is determinative of the compound's identity.

The compounds of Formulae (I) through (VI) of the invention are generally synthesized according the following generic Schemes 1-11 below.

As described in Scheme 1, dihalogenated, bicyclic compounds, as depicted by structure 1, are subjected to standard nucleophilic aromatic substitution conditions in cases where a carbon-heteroatom bond formation is desired, or to palladium catalyzed cross-coupling conditions when carbon-carbon bond formation is desired. Depending on the configuration of 1 with respect to the heterocyclic class and substitution pattern, the initial coupling reaction, where a halogen group is replaced by Y (intermediate 2), is often a selective process. In cases where the substitution reaction is non-selective, the resulting regioisomers are separated chromatographically and the desired isomer is taken forward.

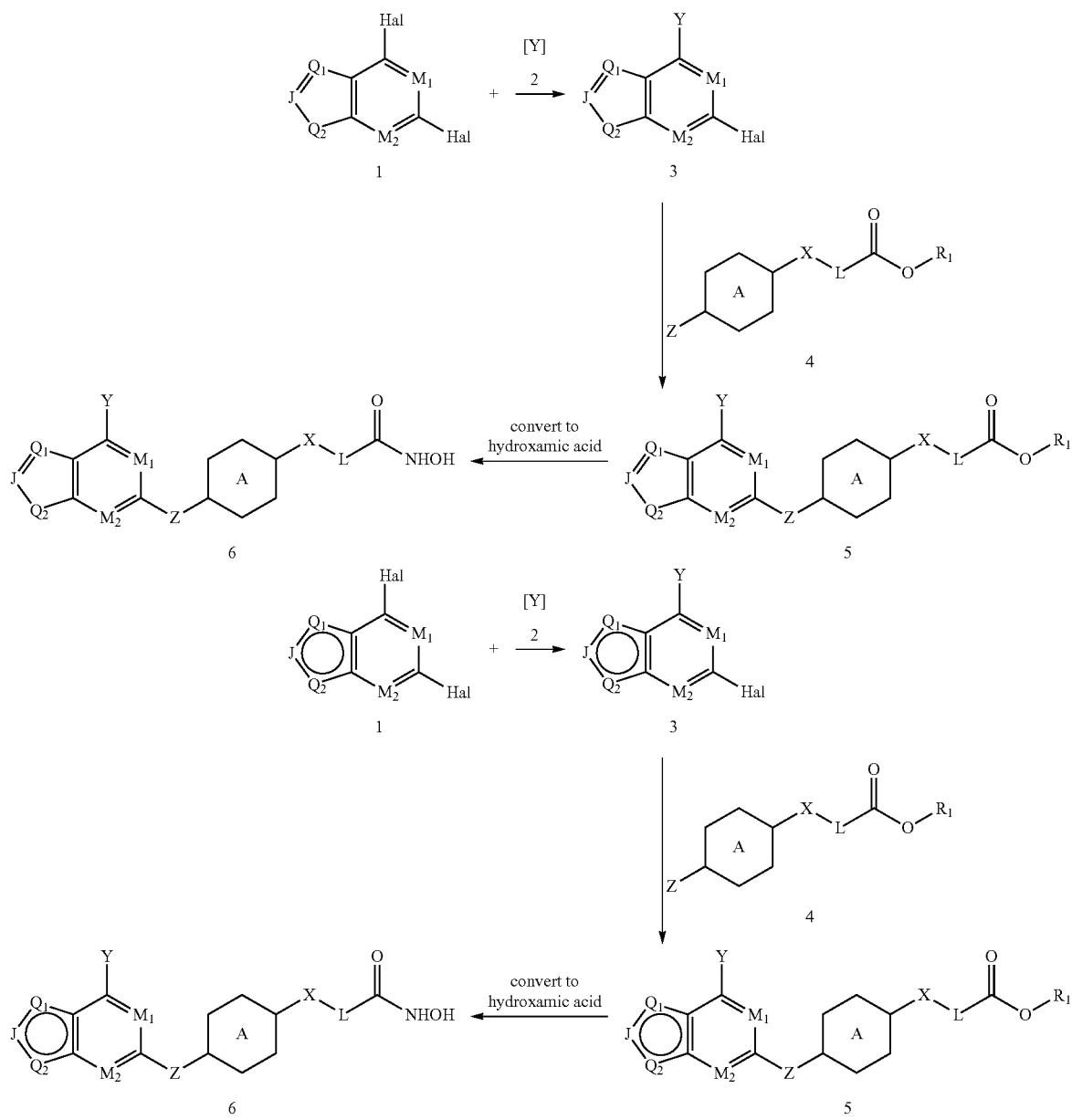

Scheme 1

The resulting monosubstituted product 3 is then subjected to a second coupling reaction with intermediate 4 to give intermediate 5. Intermediate 5 is then converted to the desired hydroxamic acid via ester hydrolysis, amide formation with an O-protected hydroxylamine derivative, such as O-tetrahydropyranyl hydroxylamine in the presence of a suitable coupling reagent, typically a carbodiimide, followed by deprotection, such as acid promoted hydrolysis of the tetrahydropyranyl group. In cases where a protecting group is required elsewhere in the molecule, it is convenient to use an acid labile group such that both protecting groups are removed concomitantly to give the final products, typically as the corresponding hydrochloride salts.

An alternative synthesis for the preparation of intermediate 5 is shown in Scheme 2. In this example, a more linear approach is used to construct the appendage containing Ring A, which is particularly useful when X is a heteroatom.

Thus, intermediate 3 is coupled with intermediate 7 under basic conditions and if necessary in the presence of a palladium catalyst to give intermediate 8. Removal of the protecting group then unmasks X which is coupled with the electrophilic component 9 under basic conditions to give 5.

Scheme 2

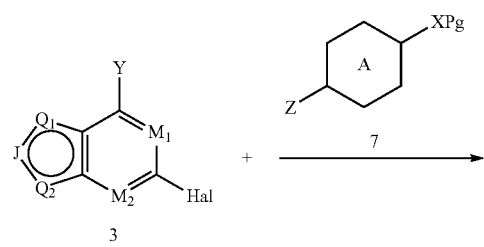

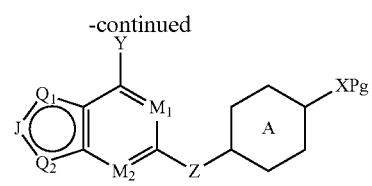

8

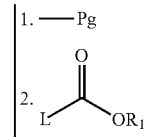

9

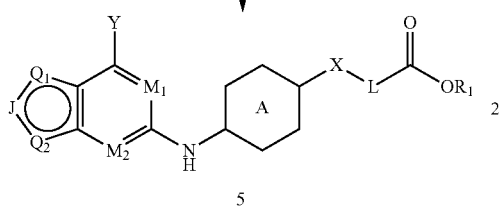

5

Another alternative synthesis for the preparation of compound 5 is shown in Scheme 3. In this case, an iodo group is used in place of the standard chloro group which facilitates palladium catalyzed cross coupling to form either a carbon-hetero atom or a carbon-carbon bond, particularly in cases where selectivity is desired such as when both $M_1$ and $M_2$ are carbon. Subsequent coupling with intermediate 7, again via palladium catalysis delivers the intermediate 8.

Scheme 3

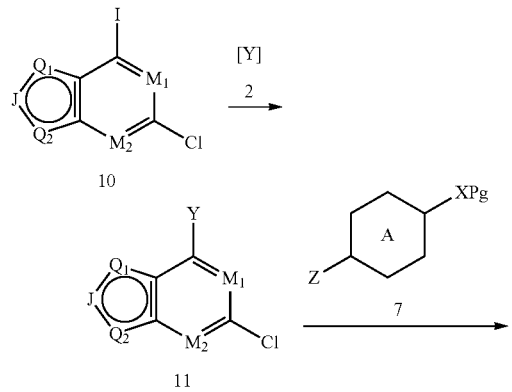

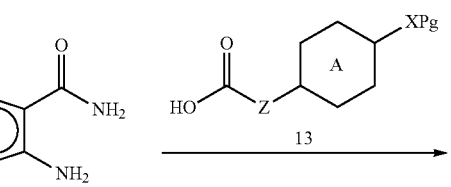

8

Another alternative synthesis for the preparation of intermediate 5 is shown in Scheme 4. This general approach is particularly useful for constructing compounds where Z is carbon. Thus, Intermediate 12 is condensed with carboxylic acid 13 to give pyrimidinone 14 which is converted to the corresponding chloride 15 upon treatment with $POCl_3$.

Scheme 4

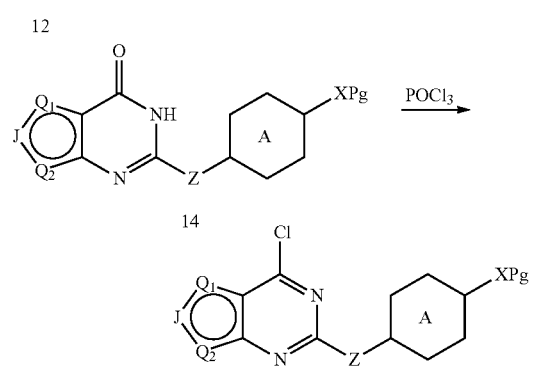

With regard to the synthesis of compounds containing an imidazo moiety, it may be necessary to protect the N1 nitrogen since the N—H group is often incompatible with the subsequent chemistry. Starting materials of the general structure 18 in Scheme 5 are typically protected either prior to, or after the first coupling reaction. A typical protecting group for substrates of this type is teraydropyranyl or paramethoxybenzyl, both of which can be removed under acidic conditions.

Scheme 5

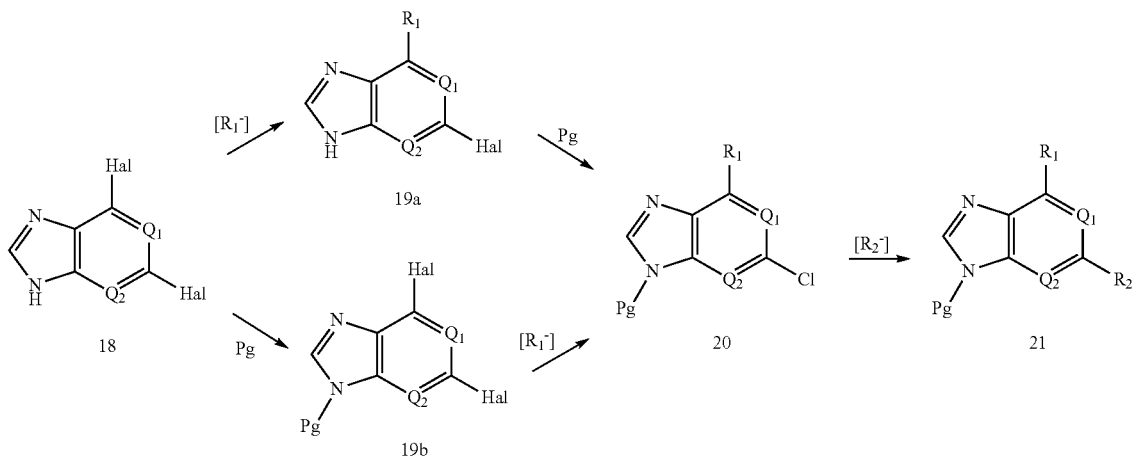

For the synthesis of N-substituted imidazo derivatives, it is convenient to directly alkylate intermediates of the general structure 12 of Scheme 6 under basic conditions, or perform an N-arylation using, for example, an aryl boronic acid in the presence of a transition metal catalyst followed by chromatographic separation of regioisomers if necessary.

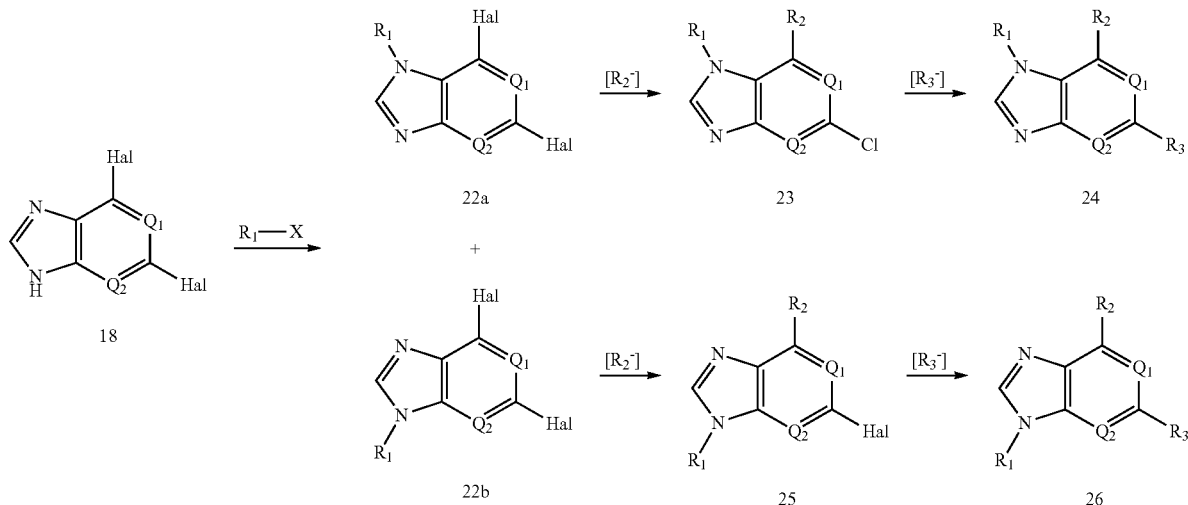

Scheme 6

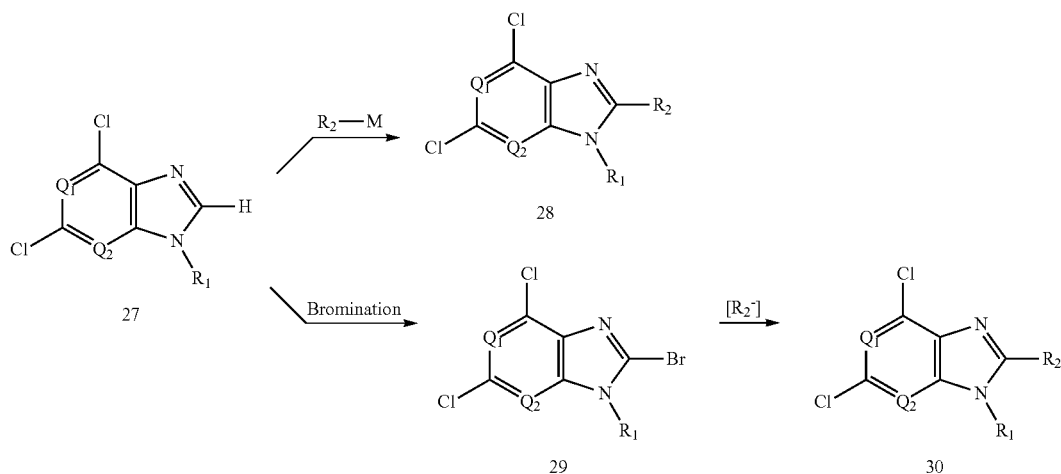

Scheme 7

As shown in Scheme 7, a convenient method for the direct introduction of alkyl or aryl groups onto the imidazo carbon of the general structure depicted by intermediate 27, which requires no prior activation of the imidazo C—H, entails treatment with an organometallic reagent with or without transition metal catalysis depending on the choice of metal to give 28. Alternatively, that position can be halogenated to give intermediate 29 and subsequently reacted with a variety of nucleophiles, including both heteroatom and carbon nucleophiles to give 30.

Scheme 8

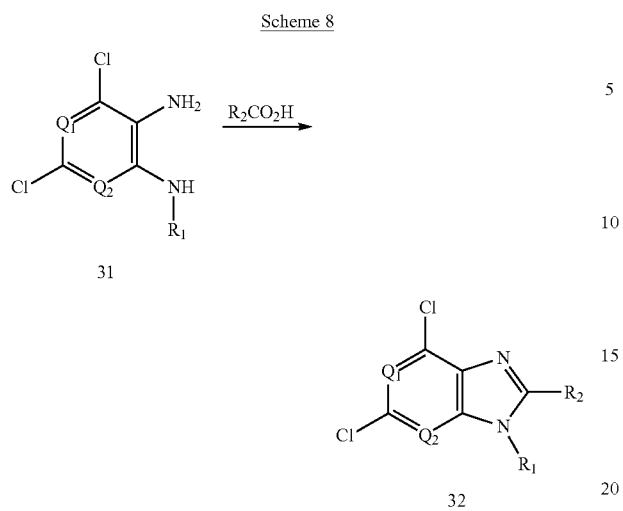

Alternatively, intermediate 32 can be can be prepared through the condensation of the 1,2-diamino derivative 31 with a carboxylic acid.

Scheme 9

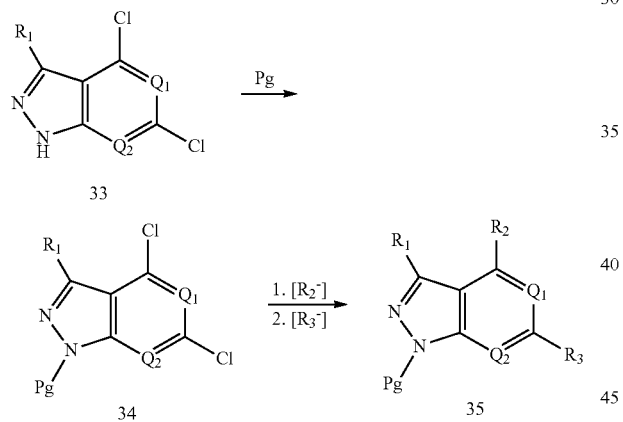

As shown in Scheme 9, the chemistry used for the preparation of the pyrrazolo intermediate 35 is analogous to that described in Scheme 4 for the preparation of the corresponding imidazo derivatives. As in Scheme 4, either a teraydropyranyl or paramethoxybenzyl protecting group can be utilized and is preferred.

Scheme 10

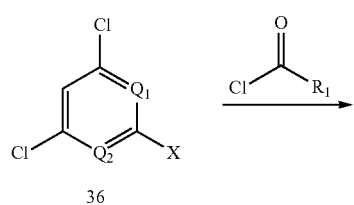

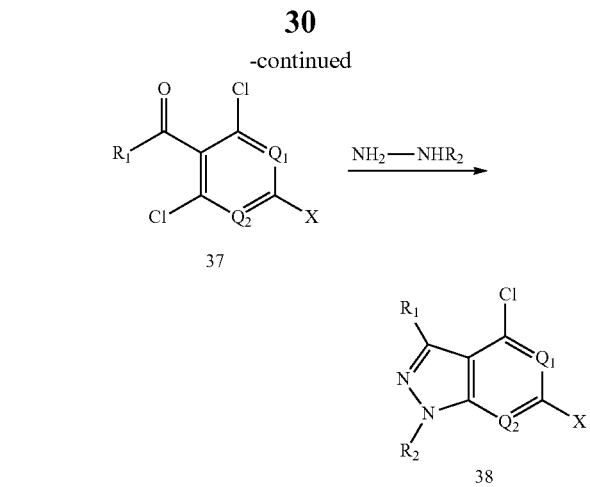

X = Cl, SMe

As shown in Scheme 10, the corresponding pyrrazolo derivatives 38 can be synthesized via acylation of 36 to give 37 followed by condensation with a hydrazine derivative to give the desired products.

Scheme 11

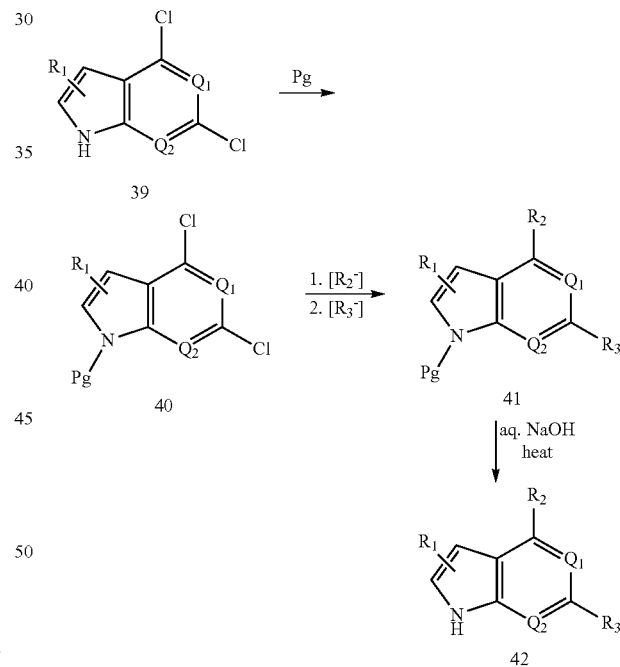

As shown in Scheme 11, intermediates such as 39 that contain one nitrogen atom in the 5-membered, heterocyclic ring, are conveniently protected using a tosylate group. After conversion of tosylate 40 to intermediate 41 via sequential cross coupling reactions, the tosylate group is removed by treatment with aqueous sodium hydroxide and heating. In a typical scenario, tosylate hydrolysis proceeds with concomitant hydrolysis of an ester group contained in $R_3$ which serves as the precursor for the desired hydroxamic acid.

EXAMPLES

The following examples are provided for illustrative purposes only and are not intended to limit the scope of the invention. Those having ordinary skill in the art of organic synthesis will appreciate that modifications to general procedures and synthetic routes contained in this application can be used to yield additional derivatives and structurally diverse compounds. Suitable organic transformations are described in March's Advanced Organic Chemistry: Reactions, Mechanisms, and Structure (Wiley-Interscience; 6$^{th}$ edition, 2007), the content of which is hereby incorporated by reference.

Example 1: Preparation of 4-(6-(cyclohexylamino)-9-(tetrahydro-2H-pyran-2-yl)-9H-purin-2-ylamino)phenol

Step 1: Preparation of 2-chloro-N-cyclohexyl-9H-purin-6-amine

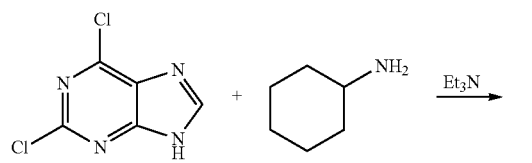

Dichloropurine (5.0 g, 26.5 mmole) was dissolved in 4 ml n-butanol. Cyclohexylamine (4.20 g, 42.3 mmole) and triethylamine (2.94 g, 29.1 mmole) were added. The mixture was stirred at 110° C. overnight. The next day, white solid formed. Ether was added and the solid was filtered, and washed with ether to get a white powder. The white powder was a mixture 2-chloro-N-cyclohexyl-9H-purin-6-amine and triethylamine hydrochloride salt, which was used directly without any further purification.

Step 2: Preparation of 2-chloro-N-cyclohexyl-9-(tetrahydro-2H-pyran-2-yl)-9H-purin-6-amine

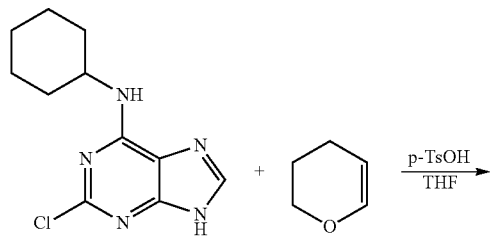

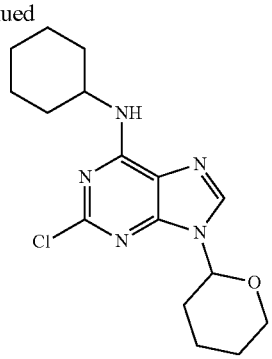

2-Chloro-N-cyclohexyl-9H-purin-6-amine (7.5 g, 29.8 mmole) was dissolved in 90 ml tetrahydrofuran. 3,4-dihydro-2H-pyran (3.8 g, 44.9 mmole) and p-toluenesulfonic acid monohydrate (0.57 g, 3.0 mmole) were added and the mixture was stirred at 70° C. overnight. The mixture was filtered and the solution was concentrated. The residue was purified by flash chromatography, gradient elution with 20~70% EtOAc/hex to get 2-chloro-N-cyclohexyl-9-(tetrahydro-2H-pyran-2-yl)-9H-purin-6-amine (7.5 g, 75% yield).

Step 3: Preparation of N6-cyclohexyl-9-(tetrahydro-2H-pyran-2-yl)-N2-(4-(triisopropylsilyloxy)phenyl)-9H-purine-2,6-diamine

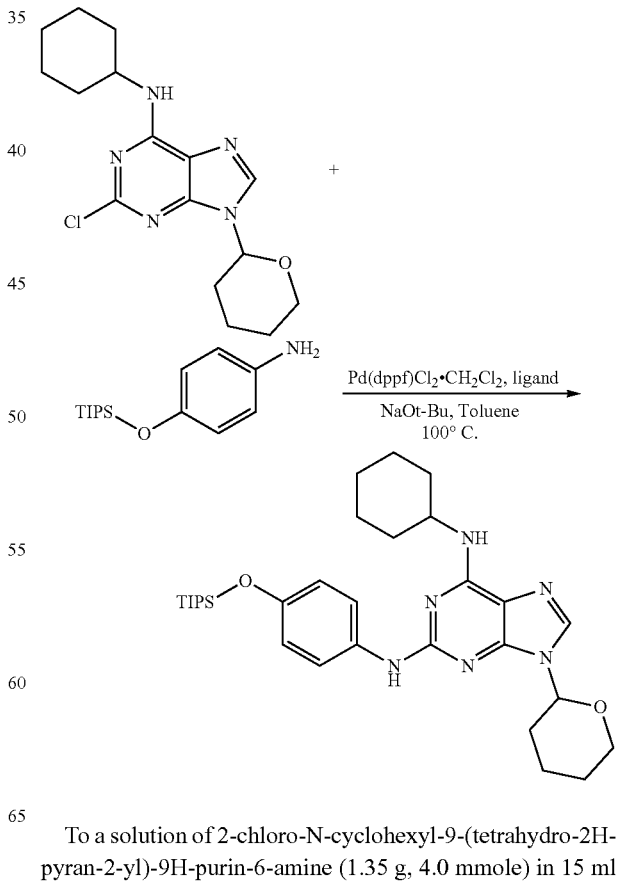

To a solution of 2-chloro-N-cyclohexyl-9-(tetrahydro-2H-pyran-2-yl)-9H-purin-6-amine (1.35 g, 4.0 mmole) in 15 ml toluene was added 4-(triisopropylsilyloxy) aniline (1.28 g, 4.8 mmole) and 2-di-tert-butylphosphino-2',4',6'-triisopropylbiphenyl (0.17 g, 0.40 mmole). The reaction mixture was degassed using Argon for 10 min after which Pd(dppf)Cl$_2$ complex with CH$_2$Cl$_2$ (0.16 g, 0.20 mmole) was added, followed by sodium t-butoxide (0.77 g, 8.0 mmole). The reaction flask was put into a preheated oil-bath at 100° C. and stirred overnight. The mixture was cooled to room temperature. To the mixture, water and EtOAc were added. The layers were separated and the aqueous layer was extracted with EtOAc. The combined organic layer was dried over Na$_2$SO$_4$ and concentrated. The crude product was purified on a silica gel column, eluted with 20% to 100% EtOAc/Hexane to get 1.7 g (75% yield) of N6-cyclohexyl-9-(tetrahydro-2H-pyran-2-yl)-N2-(4-(triisopropylsilyloxy)phenyl)-9H-purine-2,6-diamine.

Step 4: Preparation of 4-(6-(cyclohexylamino)-9-(tetrahydro-2H-pyran-2-yl)-9H-purin-2-ylamino)phenol

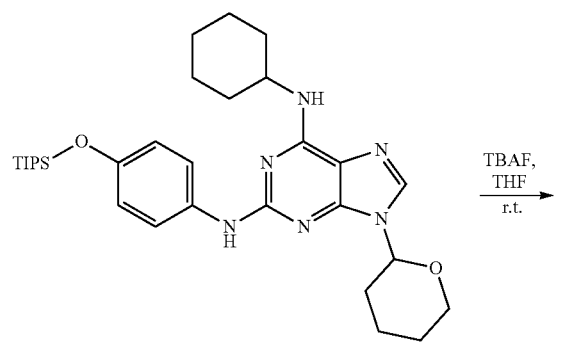

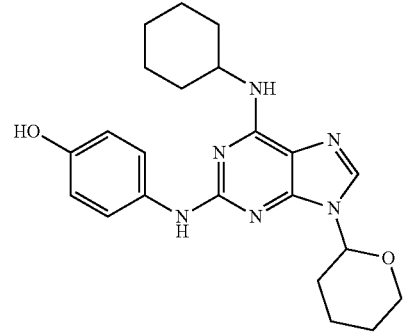

N6-Cyclohexyl-9-(tetrahydro-2H-pyran-2-yl)-N2-(4-(triisopropylsilyloxy)phenyl)-9H-purine-2,6-diamine (1.7 g, 3.0 mmole) was dissolved in 40 ml tetrahydropyran and 3.0 ml tetrabutylammonium fluoride (1.0M in THF, 3.0 mmole) was added. The mixture was stirred for 45 min. The solvent was evaporated and the mixture was purified on a silica gel column, eluted with 20% to 100% EtOAc/hexane to get 1.05 g (85% yield) of 4-(6-(cyclohexylamino)-9-(tetrahydro-2H-pyran-2-yl)-9H-purin-2-ylamino)phenol.

Example 2: Preparation of 7-(4-(6-(cyclohexylamino)-9H-purin-2-ylamino)phenoxy)-N-hydroxyheptanamide hydrochloride salt Step 1: Preparation of ethyl 7-(4-(6-(cyclohexylamino)-9-(tetrahydro-2H-pyran-2-yl)-9H-purin-2-ylamino)phenoxy)heptanoate

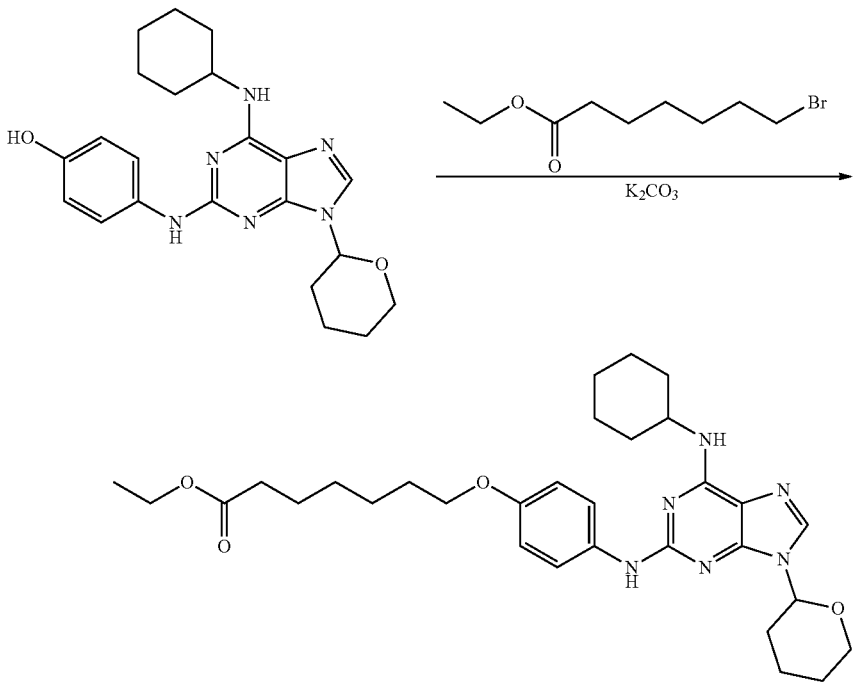

4-(6-(Cyclohexylamino)-9-(tetrahydro-2H-pyran-2-yl)-9H-purin-2-ylamino)phenol (760 mg, 1.86 mmole) was dissolved in 5 ml dimethylformamide. Ethyl 7-bromoheptanoate (882 mg, 3.72 mmole) and potassium carbonate (771 mg, 5.58 mmole) were added. The mixture was heated at 75° C. overnight. Additional ethyl 7-bromoheptanoate (380 mg, 1.86 mmole) and potassium carbonate (257 mg, 1.86 mmole) were added and heated for one more day. Additional ethyl 7-bromoheptanoate (190 mg, 0.93 mmole) and potassium carbonate (257 mg, 1.86 mmole) were added and heated for two more days. The mixture was cooled to room temperature. To the mixture, water and ethyl acetate were added. The layers were separated and the aqueous layer was extracted with ethyl acetate. The combined organic layer was dried with $Na_2SO_4$ and concentrated. The residue was placed under a stream of air to blow off dimethyl formamide. It was then purified on a silica gel column, gradient elution with 20%/80% EtOAc/Hexane to 100% EtOAc to give ethyl 7-(4-(6-(cyclohexylamino)-9-(tetrahydro-2H-pyran-2-yl)-9H-purin-2-ylamino)phenoxy)heptanoate (946 mg, 90% yield).

Alternative Preparation of ethyl 7-(4-(6-(cyclohexylamino)-9-(tetrahydro-2H-pyran-2-yl)-9H-purin-2-ylamino)phenoxy)heptanoate

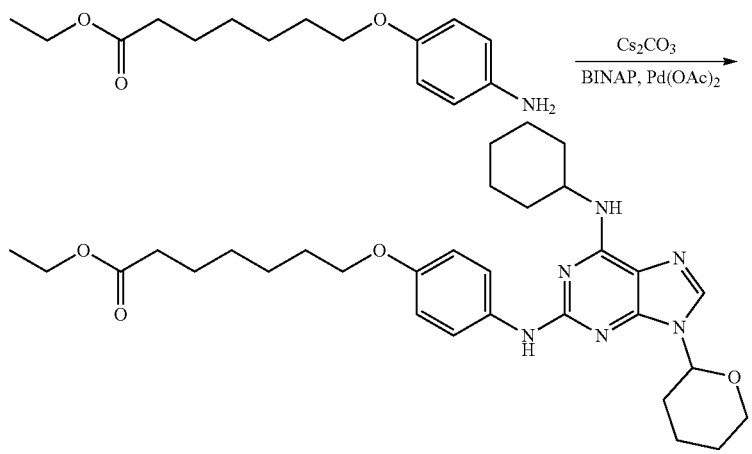

To a solution of 2-chloro-N-cyclohexyl-9-(tetrahydro-2H-pyran-2-yl)-9H-purin-6-amine (150 mg, 0.49 mmole) in 2 ml toluene was added ethyl 7-(4-aminophenoxy) heptanoate (142 mg, 0.54 mmole) and BINAP ligand (84 mg, 0.13 mmole). The reaction mixture was degassed using Argon for 10 min after which palladium acetate (15 mg, 0.067 mmole) was added, followed by cesium carbonate (437 mg, 1.3 mmole). The reaction flask was put into a preheated oil-bath at 100° C. and stirred for 2 hours. The mixture was cooled to room temperature. To the mixture, water and EtOAc were added. The layers were separated and the aqueous layer was extracted with EtOAc. The combined organic layer was dried over $Na_2SO_4$ and concentrated. The crude product was purified on a silica gel column, gradient elution with 20%/80% EtOAc/hexane to 80%/20% EtOAc/Hexane to get 190 mg (75% yield) of ethyl 7-(4-(6-(cyclohexylamino)-9-(tetrahydro-2H-pyran-2-yl)-9H-purin-2-ylamino)phenoxy)heptanoate.

Step 2: Preparation of 7-(4-(6-(cyclohexylamino)-9-(tetrahydro-2H-pyran-2-yl)-9H-purin-2-ylamino)phenoxy)heptanoic acid

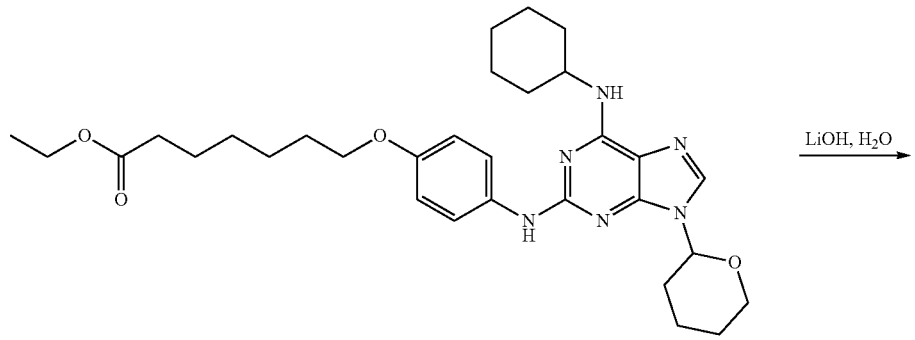

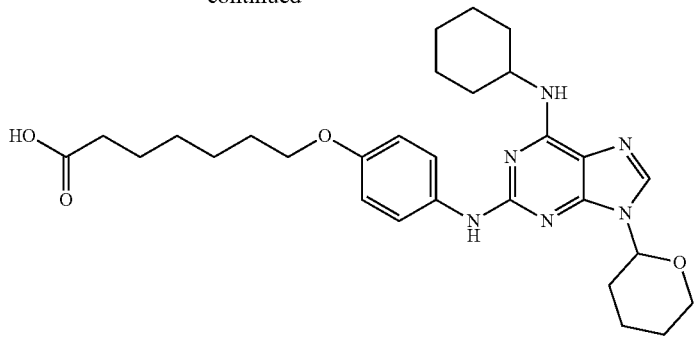

To ethyl 7-(4-(6-(cyclohexylamino)-9-(tetrahydro-2H-pyran-2-yl)-9H-purin-2-ylamino)phenoxy)heptanoate (946 mg, 1.68 mmole) was added 9 ml methanol and 3 ml water. To the suspension, lithium hydroxide monohydrate (141 mg, 3.35 mmole) was added. Additional 9 ml of methanol was added after an hour to aid the solubility. The reaction was stirred at room temperature overnight. Additional lithium hydroxide monohydrate (14 mg, 0.34 mmole) was added the second day and the reaction was let go for one more day. Ethyl acetate and water were added. The aqueous layer was acidified with 1N HCl. The layers were separated and the aqueous layer was extracted with ethyl acetate. The combined organic layer was dried with $Na_2SO_4$ and concentrated. The crude product was used without further purifications.

Step 3: Preparation of 7-(4-(6-(cyclohexylamino)-9-(tetrahydro-2H-pyran-2-yl)-9H-purin-2-ylamino)phenoxy)-N-(tetrahydro-2H-pyran-2-yloxy)heptanamide 7-(4-(6-(cyclohexylamino)-9-(tetrahydro-2H-pyran-2-yl)-9H-purin-2-ylamino)phenoxy)heptanoic acid (680 mg, 1.27 mmole) was dissolved in 8 ml dimethyl formamide. 1-hydroxybenzotriazole monohydrate (253 mg, 1.65 mmole) and N-(3-dimethylaminopropyl)-N'-ethylcarbodiimide hydrochloride (365 mg, 1.90 mmole) were added. After 30 min, triethylamine (514 mg, 5.08 mmole) and O-(tetrahydro-2H-pyran-2-yl)hydroxylamine (164 mg, 1.40 mmole) were added and the mixture was stirred overnight. The next day, additional O-(tetrahydro-2H-pyran-2-yl)hydroxylamine (82 mg, 1.40 mmole) were added and the mixture was stirred for 1.5 hours. To the mixture, water and ethyl acetate were added. The layers were separated and the aqueous layer was extracted with ethyl acetate. The combined organic layer was dried with $Na_2SO_4$ and concentrated. Flash chromatography, gradient elution with 20%/80% EtOAc/hex to EtOAC to get 7-(4-(6-(cyclohexylamino)-9-(tetrahydro-2H-pyran-2-yl)-9H-purin-2-ylamino)phenoxy)-N-(tetrahydro-2H-pyran-2-yloxy)heptanamide (700 mg, 87%).

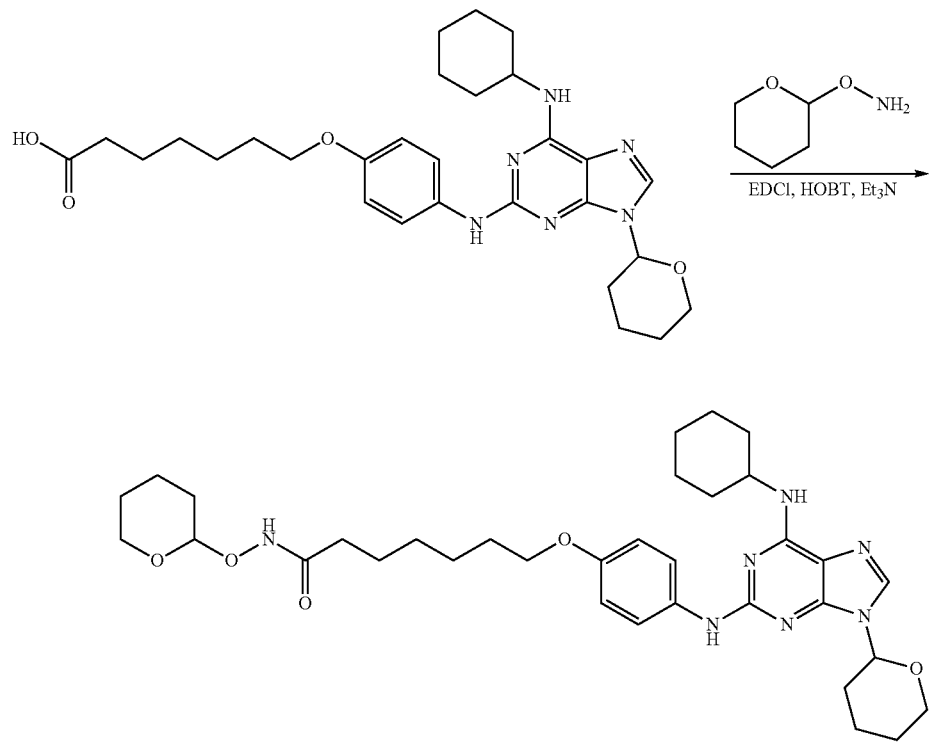 [SMILES: O=C(O)CCCCCCOc1ccc(Nc2nc(NC3CCCCC3)c3ncn(C4CCCCO4)c3n2)cc1 ; NOC1CCCCO1 ; O=C(CCCCCCOc1ccc(Nc2nc(NC3CCCCC3)c3ncn(C4CCCCO4)c3n2)cc1)NOC1CCCCO1]

Step 4: Preparation of 7-(4-(6-(cyclohexylamino)-9H-purin-2-ylamino)phenoxy)-N-hydroxyheptanamide hydrochloride salt

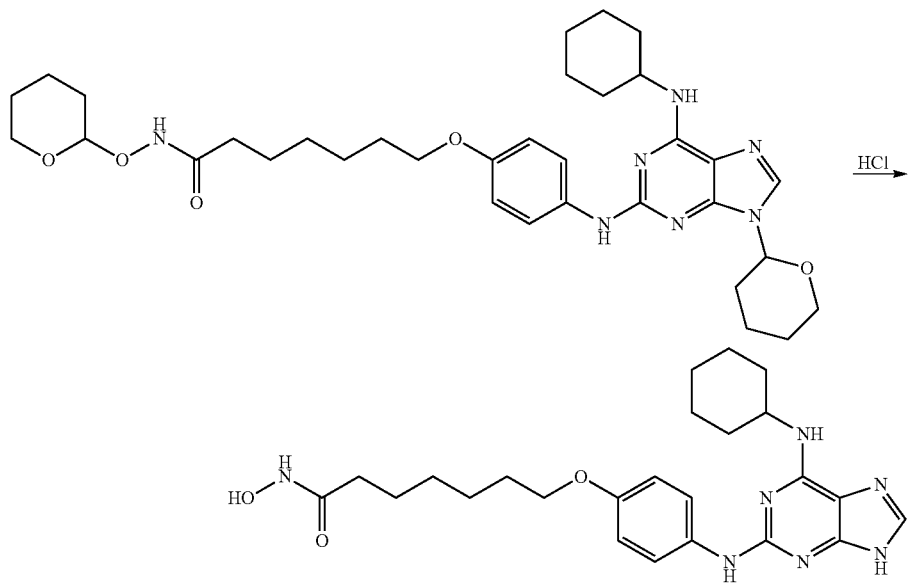

7-(4-(6-(Cyclohexylamino)-9-(tetrahydro-2H-pyran-2-yl)-9H-purin-2-ylamino)phenoxy)-N-(tetrahydro-2H-pyran-2-yloxy)heptanamide (500 mg, 0.79 mmole) was dissolved in 4 ml dichloromethane. 4 ml 4N HCl in dioxane was added and the mixture was stirred at room temperature for 4 hours. Ether was added and the precipitate was filtered, and washed with ether to get 7-(4-(6-(cyclohexylamino)-9H-purin-2-ylamino)phenoxy)-N-hydroxyheptanamide as its hydrochloride salt. Mass Spec(m/z): 468.2 (M+1)

Example 3: Preparation of 6-(4-(6-(cyclohexylamino)-9H-purin-2-ylamino)phenoxy)-N-hydroxyhexanamide hydrochloride salt Synthesized according to the procedure described above in Examples 1 and 2. Mass Spec(m/z): 454.2 (M+1)

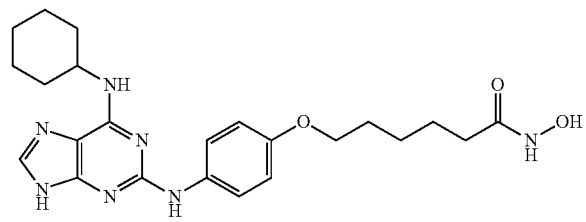 [SMILES: O=C(CCCCCOc1ccc(Nc2nc(NC3CCCCC3)c3nc[nH]c3n2)cc1)NO]

Example 4: Preparation of 5-(4-(6-(cyclohexylamino)-9H-purin-2-ylamino)phenoxy)-N-hydroxypentanamide hydrochloride salt Synthesized according to the procedure described above in Examples 1 and 2. Mass Spec(m/z): 440.2 (M+1)

Example 5: Preparation of 4-(4-(6-(cyclohexylamino)-9H-purin-2-ylamino)phenoxy)-N-hydroxybutanamide hydrochloride salt Synthesized according to the procedure described above in Examples 1 and 2. Mass Spec(m/z): 426.2 (M+1)

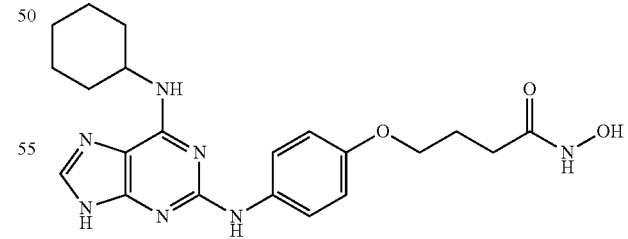

Example 6: Preparation of 8-(4-(6-(cyclohexylamino)-9H-purin-2-ylamino)phenoxy)-N-hydroxyoctanamide hydrochloride salt Synthesized according to the procedure described above in Examples 1 and 2. Mass Spec(m/z): 482.3 (M+1)

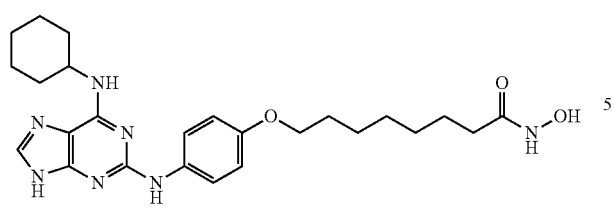

Example 7: Preparation of 4-(6-(cyclohexylamino)-9-methyl-9H-purin-2-ylamino)phenol

Step 1: Preparation of 2-chloro-N-cyclohexyl-9-methyl-9H-purin-6-amine

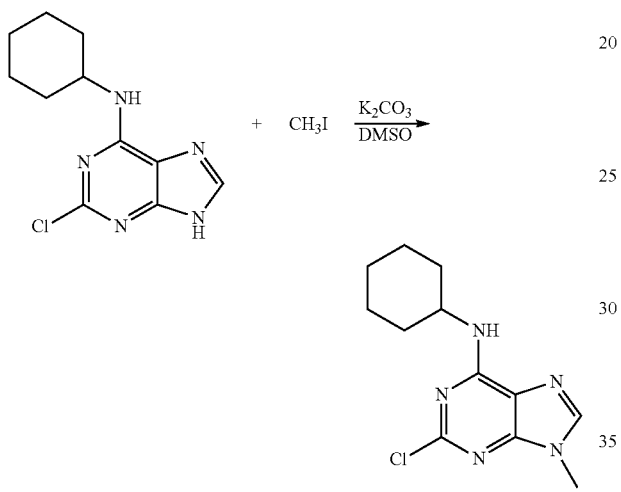

A mixture 2-chloro-N-cyclohexyl-9H-purin-6-amine and triethylamine hydrochloride salt (300 mg, 0.715 mmole) was dissolved in 10 ml dimethyl sulfoxide. Potassium carbonate (593 mg, 4.3 mmole) was added, followed by iodomethane (507 mg, 3.6 mmole). The mixture was stirred at room temperature overnight. To the mixture, water and EtOAc were added. The layers were separated and the aqueous layer was extracted with EtOAc. The combined organic layer was dried over Na₂SO₄ and concentrated. The crude product was purified on a silica gel column, eluted with 50% to 100% EtOAc/Hexane to get 180 mg (95% yield) of 2-chloro-N-cyclohexyl-9-methyl-9H-purin-6-amine.

Step 2: Preparation of 2 N6-cyclohexyl-9-methyl-N2-(4-(triisopropylsilyloxy)phenyl)-9H-purine-2,6-diamine

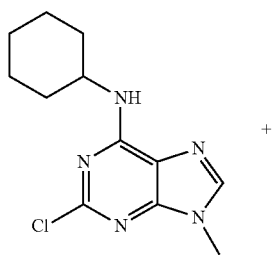

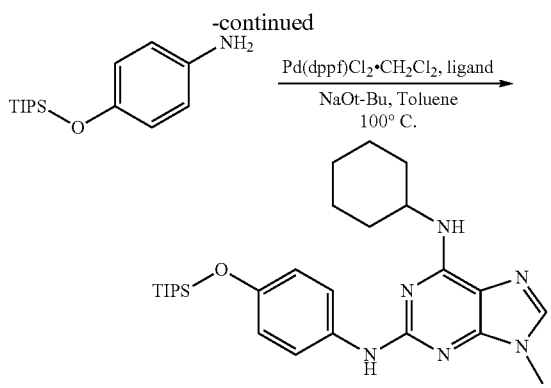

To a solution of 2-chloro-N-cyclohexyl-9-methyl-9H-purin-6-amine (1.06 g, 3.99 mmole) in 15 ml toluene was added 4-(triisopropylsilyloxy) aniline (1.27 g, 4.79 mmole) and 2-di-tert-butylphosphino-2',4',6'-triisopropylbiphenyl (0.17 g, 0.40 mmole). The reaction mixture was degassed using Argon for 10 min after which Pd(dppf)Cl₂ complex with CH₂Cl₂ (0.16 g, 0.20 mmole) was added, followed by sodium t-butoxide (0.77 g, 7.98 mmole). The reaction flask was put into a preheated oil-bath at 100° C. and stirred overnight. The mixture was cooled to room temperature. To the mixture, water and EtOAc were added. The layers were separated and the aqueous layer was extracted with EtOAc. The combined organic layer was dried over Na₂SO₄ and concentrated. The crude product was purified on a silica gel column, eluted with 50% to 100% EtOAc/Hexane, then EtOAc, then 5% MeOH/EtOAc to get 1.3 g (66% yield) of N6-cyclohexyl-9-methyl-N2-(4-(triisopropylsilyloxy)phenyl)-9H-purine-2,6-diamine.

Step 3: Preparation of 4-(6-(cyclohexylamino)-9-methyl-9H-purin-2-ylamino)phenol

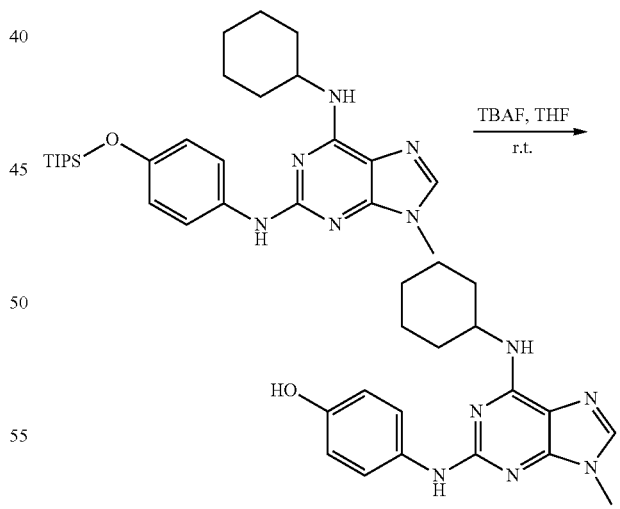

N6-Cyclohexyl-9-methyl-N2-(4-(triisopropylsilyloxy)phenyl)-9H-purine-2,6-diamine (1.3 g, 2.63 mmole) was dissolved in 35 ml THF and 2.7 ml TBAF (1.0M in THF, 2.7 mmole) was added. The mixture was stirred for 45 min. The solvent was evaporated and the mixture was purified on a silica gel column, eluted with 60% to 100% EtOAc/hexane, then EtOAc, then 10% MeOH in EtOAc to get 0.85 g (96% yield) of 4-(6-(cyclohexylamino)-9-methyl-9H-purin-2-ylamino)phenol.

Example 8: Preparation of 7-(4-(6-(Cyclohexylamino)-9-methyl-9H-purin-2-ylamino)phenoxy)-N-hydroxyheptanamide hydrochloride salt Step 1: Preparation of ethyl 7-(4-(6-(cyclohexylamino)-9-methyl-9H-purin-2-ylamino)phenoxy)heptanoate

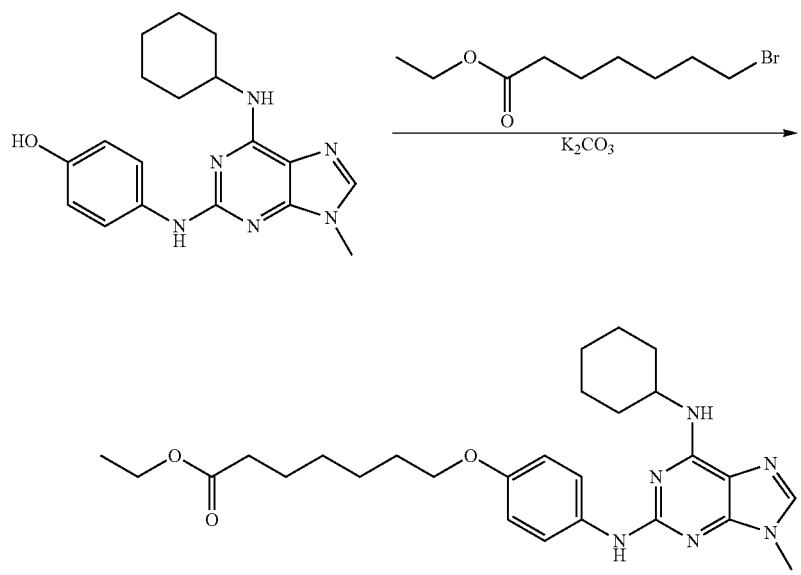

4-(6-(Cyclohexylamino)-9-methyl-9H-purin-2-ylamino)phenol (500 mg, 1.48 mmole) was dissolved in 4 ml dimethylformamide. Ethyl 7-bromoheptanoate (701 mg, 2.96 mmole) and potassium carbonate (613 mg, 4.43 mmole) were added. The mixture was heated at 70° C. overnight. Additional ethyl 7-bromoheptanoate (350 mg, 1.48 mmole) was added and heated for a day. Additional ethyl 7-bromoheptanoate (175 mg, 0.74 mmole) and potassium carbonate (204 mg, 1.48 mmole) were added and heated two more days. The mixture was cooled to room temperature. To the mixture, water and EtOAc were added. The layers were separated and the aqueous layer was extracted with EtOAc. The combined organic layer was dried with $Na_2SO_4$ and concentrated. The residue was placed under a stream of air to blow off DMF. It was then purified on a silica gel column, eluted with EtOAc, the 5% MeOH/EtOAc to get ethyl 7-(4-(6-(cyclohexylamino)-9-methyl-9H-purin-2-ylamino)phenoxy)heptanoate (300 mg, 48% yield).

Step 2: Preparation of 7-(4-(6-(Cyclohexylamino)-9-methyl-9H-purin-2-ylamino)phenoxy)heptanoic acid

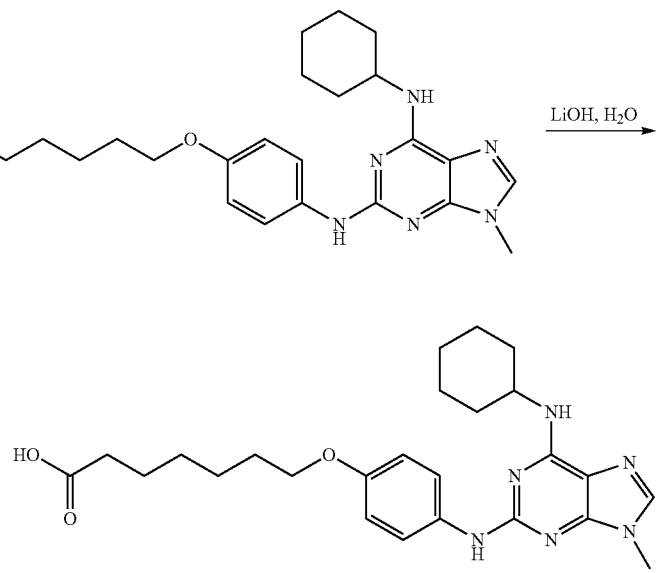

To ethyl 7-(4-(6-(cyclohexylamino)-9-methyl-9H-purin-2-ylamino)phenoxy)heptanoate (350 mg, 0.708 mmole) was added 3 ml methanol and 0.5 ml water. To the suspension, lithium hydroxide monohydrate (74 mg, 1.76 mmole) was added. The reaction was stirred at room temperature until LC/MS showed completion of the reaction. Ethyl acetate and water were added. The aqueous layer was acidified with 1N HCl. The layers were separated and the aqueous layer was extracted with ethyl acetate. The combined organic layer was dried with Na$_2$SO$_4$ and concentrated. The crude product was used without further purifications.

Step 3: Preparation of 7-(4-(6-(cyclohexylamino)-9-methyl-9H-purin-2-ylamino)phenoxy)-N-(tetrahydro-2H-pyran-2-yloxy)heptanamide

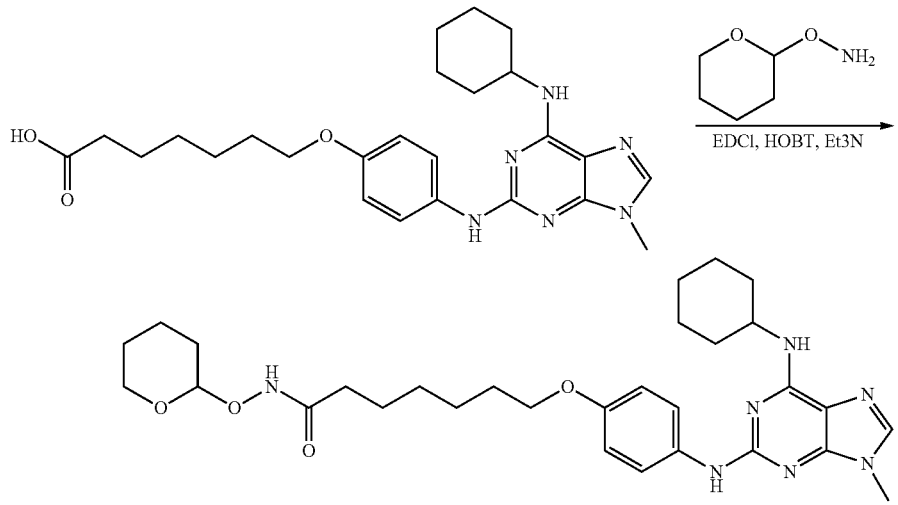

7-(4-(6-(Cyclohexylamino)-9-methyl-9H-purin-2-ylamino)phenoxy)heptanoic acid (140 mg, 0.30 mmole) was dissolved in 1 ml dimethyl formamide. 1-hydroxybenzotriazole monohydrate (60 mg, 0.39 mmole) and N-(3-dimethylaminopropyl)-N'-ethylcarbodiimide hydrochloride (75 mg, 0.39 mmole) were added. After 5 min, triethylamine (122 mg, 1.2 mmole) and O-(tetrahydro-2H-pyran-2-yl) hydroxylamine (46 mg, 0.39 mmole) were added and the mixture was stirred overnight. Additional same amount of reagents were added, and the reaction was stirred for another day. To the mixture, water and ethyl acetate were added. The layers were separated and the aqueous layer was extracted with ethyl acetate. The combined organic layer was dried with Na$_2$SO$_4$ and concentrated. Flash chromatography, gradient elution with 1:1 EtOAc/hex to EtOAC, then eluted with EtOAc, then eluted with 10% MeOH in EtOAc to get 7-(4-(6-(cyclohexylamino)-9-methyl-9H-purin-2-ylamino)phenoxy)-N-(tetrahydro-2H-pyran-2-yloxy)heptanamide (170 mg, 100%).

Step 4: Preparation of 7-(4-(6-(Cyclohexylamino)-9-methyl-9H-purin-2-ylamino)phenoxy)-N-hydroxyheptanamide hydrochloride salt

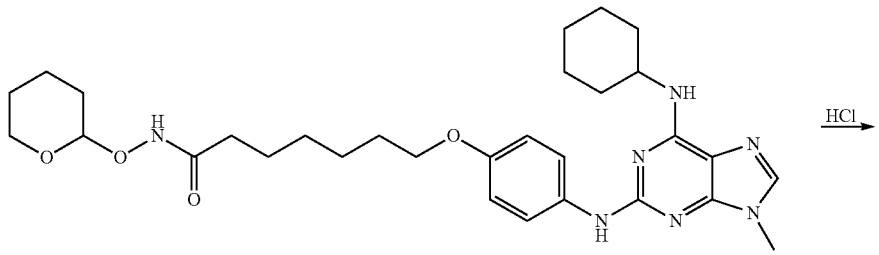

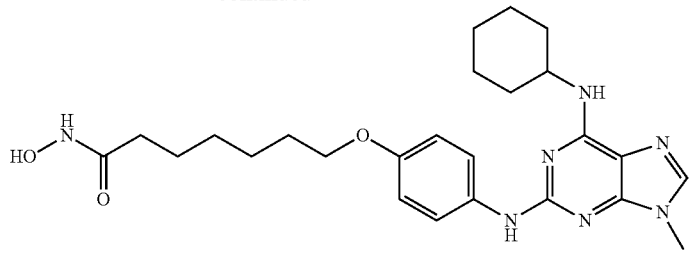

7-(4-(6-(Cyclohexylamino)-9-methyl-9H-purin-2-ylamino)phenoxy)-N-(tetrahydro-2H-pyran-2-yloxy)heptanamide (285 mg, 0.50 mmole) was dissolved in 3 ml dichloromethane. 3 ml 4N HCl in dioxane was added and the mixture was stirred at room temperature for 4 hours. Ether was added and the white precipitate was filtered, and washed with ether to get 7-(4-(6-(Cyclohexylamino)-9-methyl-9H-purin-2-ylamino)phenoxy)-N-hydroxyheptanamide as its hydrochloride salt. Mass Spec(m/z): 482.3 (M+1).

Example 9: Preparation of methyl 6-bromohexanoate, 6-(4-(6-(cyclohexylamino)-9-methyl-9H-purin-2-ylamino)phenoxy)-N-hydroxyhexanamide hydrochloride salt

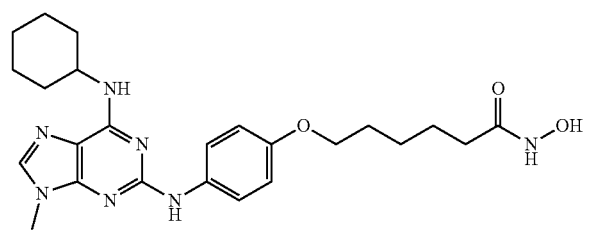 [SMILES: Cn1cnc2c(NC3CCCCC3)nc(Nc3ccc(OCCCCCC(=O)NO)cc3)nc21]

Synthesized according to the procedure described above in Examples 7 and 8, using appropriate starting materials. Mass Spec(m/z): 468.2 (M+1).

Example 10: Preparation of 2-chloro-N-phenyl-9-(tetrahydro-2H-pyran-2-yl)-9H-purin-6-amine

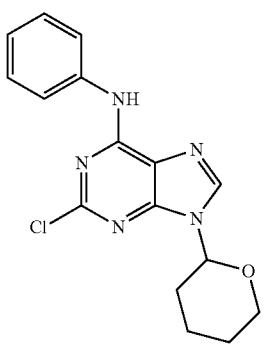 [SMILES: Clc1nc(Nc2ccccc2)c2ncn(C3CCCCO3)c2n1]

Synthesized according to the procedure described above in Example 1, step 1 and step 2.

Example 11: Preparation of N-hydroxy-7-(4-(6-(phenylamino)-9H-purin-2-ylamino)phenoxy)heptanamide hydrochloride salt

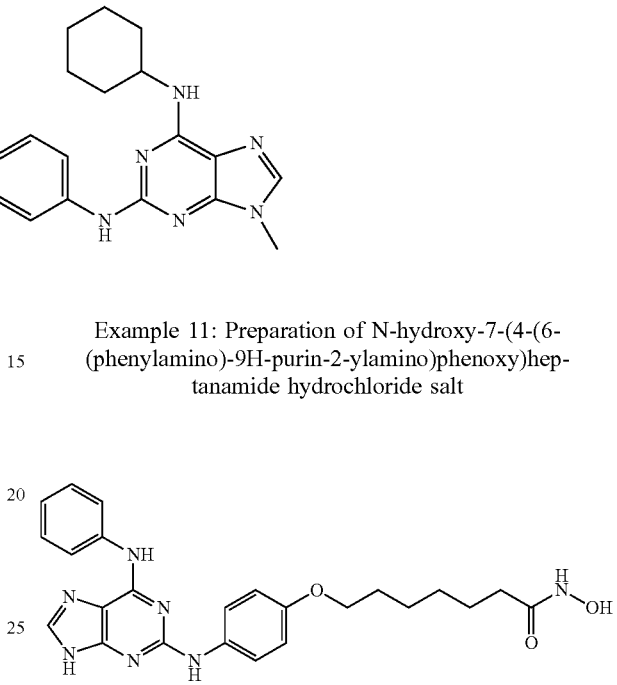

Synthesized using intermediate XX according to the procedure described above in Examples 2, alternative step 1, step 2, step 3 and step 4. Mass Spec(m/z): 462.2 (M+1)

Example 12: Preparation of 2-chloro-6-isopropoxy-9-(tetrahydro-2H-pyran-2-yl)-9H-purine

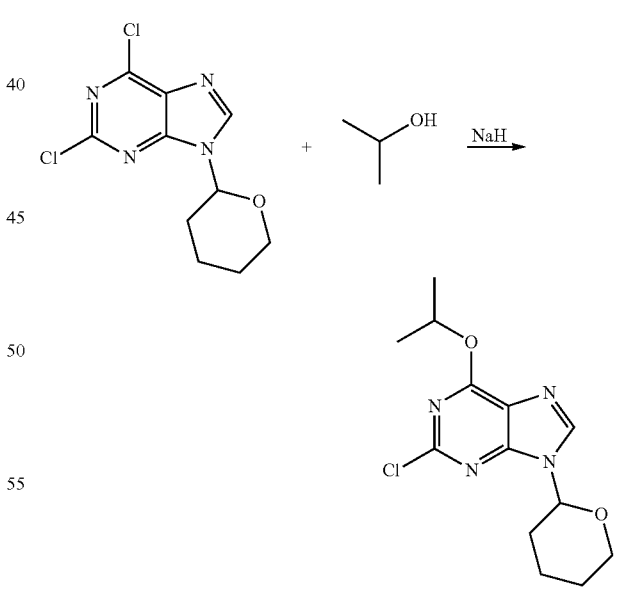

Diisopropyl alcohol (44 mg, 0.73 mmole) was dissolved in 5 ml dry THF. Sodium hydride (60% weight, 29.3 mg, 0.73 mmole) was added to the solution and the mixture was stirred at room temperature for 30 min at which time Dichloropurine (100 mg, 0.37 mmole) were added. The mixture was heated in a sealed tube at 65° C. overnight. Column purification to get the desired product.

Example 13: Preparation of N-hydroxy-7-(4-(6-isopropoxy-9H-purin-2-ylamino)phenoxy)heptanamide hydrochloride salt

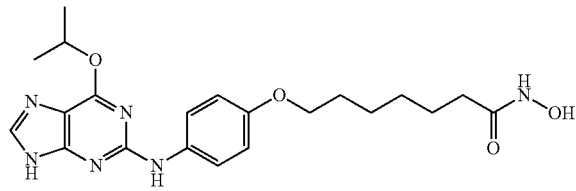 [SMILES: CC(C)Oc1nc(Nc2ccc(OCCCCCCC(=O)NO)cc2)nc2[nH]cnc12]

Synthesized using intermediate XX according to the procedure described above in Examples 2, alternative step 1, step 2, step 3 and step 4. Mass Spec(m/z): 429.2 (M+1)

Example 14: Preparation of 2-(3-(4-(6-(cyclohexylamino)-9H-purin-2-ylamino)phenoxy)propylamino)-N-hydroxyacetamide hydrochloride salt

Step 1: Preparation of 2-(3-(4-(6-(cyclohexylamino)-9-(tetrahydro-2H-pyran-2-yl)-9H-purin-2-ylamino)phenoxy)propyl)isoindoline-1,3-dione

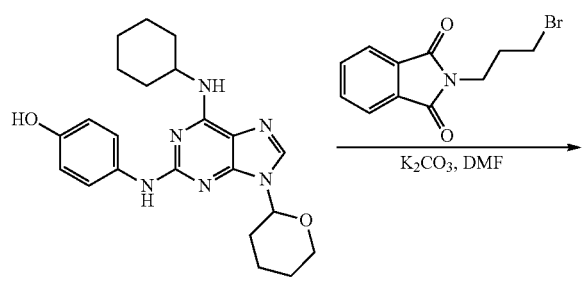

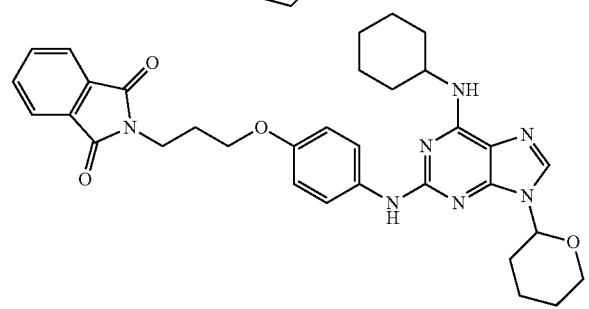

4-(6-(Cyclohexylamino)-9-(tetrahydro-2H-pyran-2-yl)-9H-purin-2-ylamino)phenol (240 mg, 0.59 mmole) was dissolved in 3 ml dimethyl formamide. Potassium carbonate (243 mg, 1.76 mmole) and N-(3-bromopropyl)phthalimide (316 mg, 1.2 mmole) were added. The mixture was heated at 60° C. Additional reagents were added until LC/MS showed completion of the reaction. Water and ethyl acetate were added. The layers were separated and the aqueous layer was extracted with ethyl acetate. The combined organic layer was dried with Na$_2$SO$_4$ and concentrated. Flash chromatography to get the desired product 2-(3-(4-(6-(cyclohexylamino)-9-(tetrahydro-2H-pyran-2-yl)-9H-purin-2-ylamino)phenoxy)propyl)-isoindoline-1,3-dione (87 mg, 25%).

Step 2: Preparation of N2-(4-(3-aminopropoxy)phenyl)-N6-cyclohexyl-9-(tetrahydro-2H-pyran-2-yl)-9H-purine-2,6-diamine

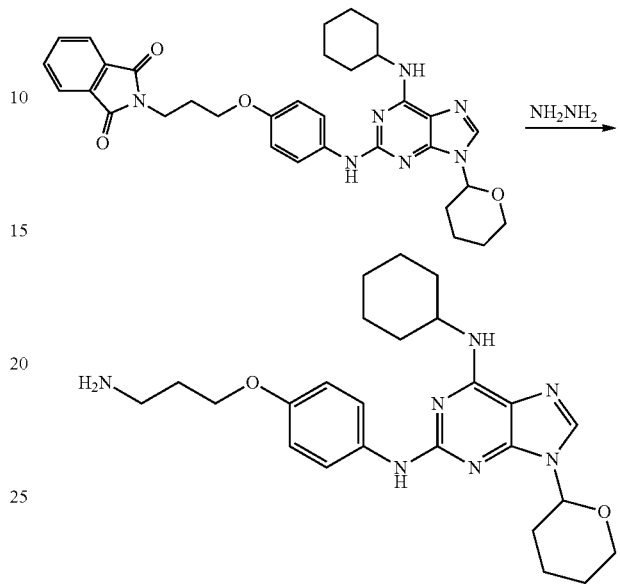

2-(3-(4-(6-(cyclohexylamino)-9-(tetrahydro-2H-pyran-2-yl)-9H-purin-2-ylamino)phenoxy)propyl)isoindoline-1,3-dione (260 mg, 0.44 mmole) was dissolved in 5 ml ethanol. Hydrazine monohydrate (44 mg, 0.88 mmole) was added. The mixture was stirred at 60° C. for several hours. The solvent was removed and flash chromatography to get the desired product N2-(4-(3-aminopropoxy)phenyl)-N6-cyclohexyl-9-(tetrahydro-2H-pyran-2-yl)-9H-purine-2,6-diamine (130 mg, 64%).

Step 3: Preparation of methyl 2-(3-(4-(6-(cyclohexylamino)-9-(tetrahydro-2H-pyran-2-yl)-9H-purin-2-ylamino)phenoxy)propylamino)acetate

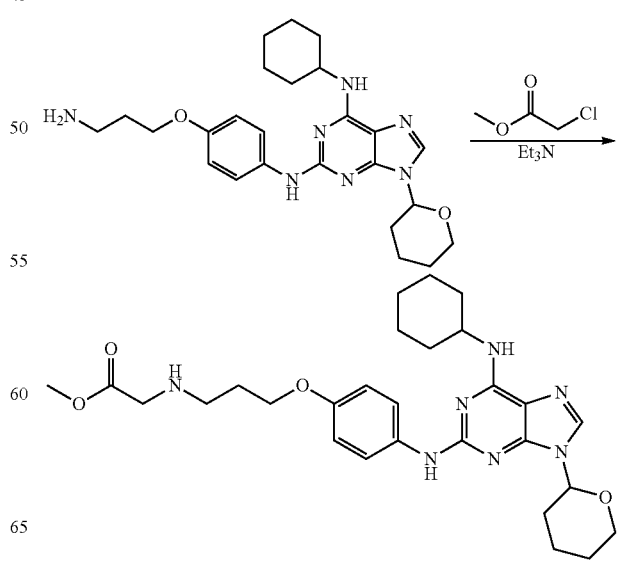

4 N2-(4-(3-aminopropoxy)phenyl)-N6-cyclohexyl-9-(tetrahydro-2H-pyran-2-yl)-9H-purine-2,6-diamine (20 mg, 0.043 mmole) was dissolved in 1 ml dimethyl formamide. Triethylamine (6.5 mg, 0.64 mmole) and methyl chloroacetate (7 mg, 0.64 mmole) were added. The mixture was heated at 70° C. for two hours. Water and ethyl acetate were added. The layers were separated and the aqueous layer was extracted with ethyl acetate. The combined organic layer was dried with Na₂SO₄ and concentrated. Flash chromatography to get the desired product methyl 2-(3-(4-(6-(cyclohexylamino)-9-(tetrahydro-2H-pyran-2-yl)-9H-purin-2-ylamino)phenoxy)propylamino)acetate (9 mg, 39%).

Step 4: Preparation of methyl 2-(tert-butoxycarbonyl(3-(4-(6-(cyclohexylamino)-9-(tetrahydro-2H-pyran-2-yl)-9H-purin-2-ylamino)phenoxy)propyl)amino)acetate

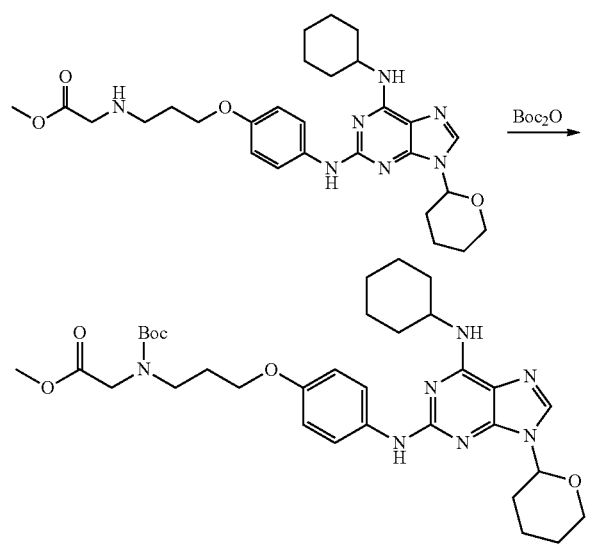

Methyl 2-(3-(4-(6-(cyclohexylamino)-9-(tetrahydro-2H-pyran-2-yl)-9H-purin-2-ylamino)phenoxy)propylamino)acetate (9 mg, 0.017 mmole) was dissolved in 0.5 ml dichloromethane. Boc anhydride (4.5 mg, 0.021 mmole) in 1 ml dichloromethane was then added. The mixture was stirred overnight. Solvent was evaporated and the product was purified by column chromatography to get the desired product.

Step 5: Preparation of 2-(tert-butoxycarbonyl(3-(4-(6-(cyclohexylamino)-9-(tetrahydro-2H-pyran-2-yl)-9H-purin-2-ylamino)phenoxy)propyl)amino)acetic acid

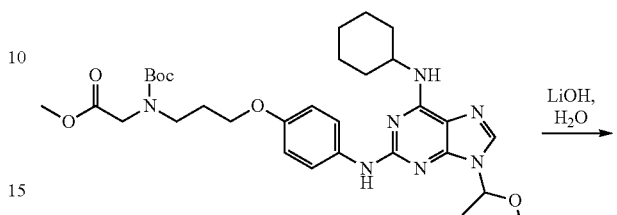

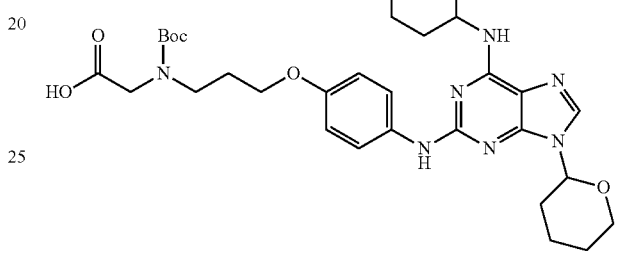

To methyl 2-(tert-butoxycarbonyl(3-(4-(6-(cyclohexylamino)-9-(tetrahydro-2H-pyran-2-yl)-9H-purin-2-ylamino)phenoxy)propyl)amino)acetate (80 mg, 0.126 mmole) was added 3 ml methanol and 0.8 ml water. To the suspension, lithium hydroxide monohydrate (11 mg, 0.25 mmole) was added. The reaction was stirred at room temperature overnight. Ethyl acetate and water were added. The aqueous layer was acidified with 1N HCl. The layers were separated and the aqueous layer was extracted with ethyl acetate. The combined organic layer was dried with Na₂SO₄ and concentrated. The crude product (41 mg) was used without further purifications.

Step 6: Preparation of tert-butyl 3-(4-(6-(cyclohexylamino)-9-(tetrahydro-2H-pyran-2-yl)-9H-purin-2-ylamino)phenoxy)propyl(2-oxo-2-(tetrahydro-2H-pyran-2-yloxyamino)ethyl)carbamate

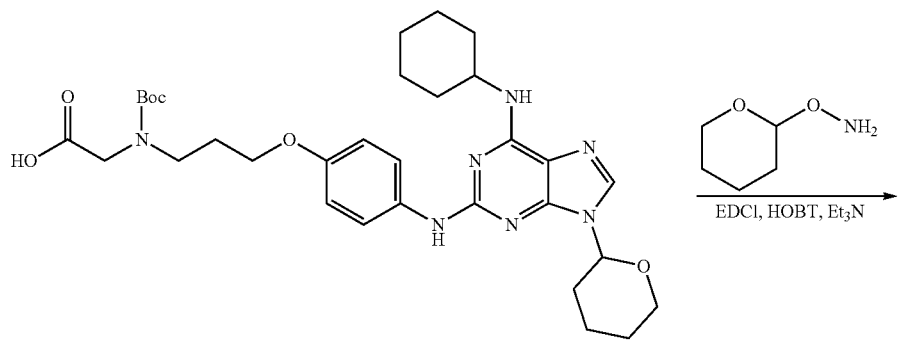

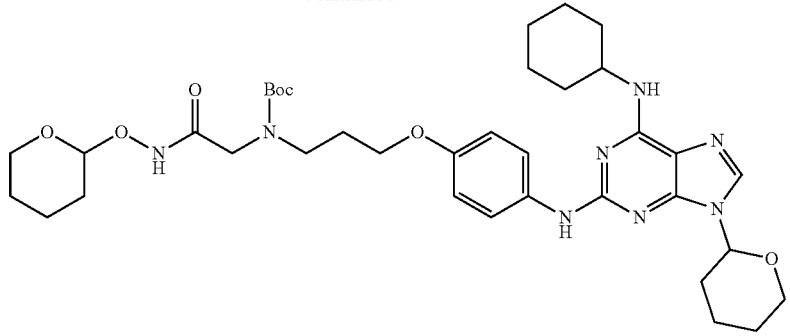

2-(Tert-Butoxycarbonyl(3-(4-(6-(cyclohexylamino)-9-(tetrahydro-2H-pyran-2-yl)-9H-purin-2-ylamino)phenoxy)propyl)amino)acetic acid (41 mg, 0.066 mmole) was dissolved in 1 ml dimethyl formamide. 1-Hydroxybenzotriazole monohydrate (13 mg, 0.086 mmole) and N-(3-dimethylaminopropyl)-N'-ethylcarbodiimide hydrochloride (19 mg, 0.099 mmole) were added. After 5 min, triethylamine (27 mg, 0.264 mmole) and O-(tetrahydro-2H-pyran-2-yl)hydroxylamine (9 mg, 0.073 mmole) were added and the mixture was stirred overnight. To the mixture, water and ethyl acetate were added. The layers were separated and the aqueous layer was extracted with ethyl acetate. The combined organic layer was dried with $Na_2SO_4$ and concentrated. Flash chromatography to get tert-butyl 3-(4-(6-(cyclohexylamino)-9-(tetrahydro-2H-pyran-2-yl)-9H-purin-2-ylamino)phenoxy)propyl(2-oxo-2-(tetrahydro-2H-pyran-2-yloxyamino)ethyl)carbamate (30 mg, 63%).

Step 7: Preparation of 2-(3-(4-(6-(cyclohexylamino)-9H-purin-2-ylamino)phenoxy)propylamino)-N-hydroxyacetamide hydrochloride salt

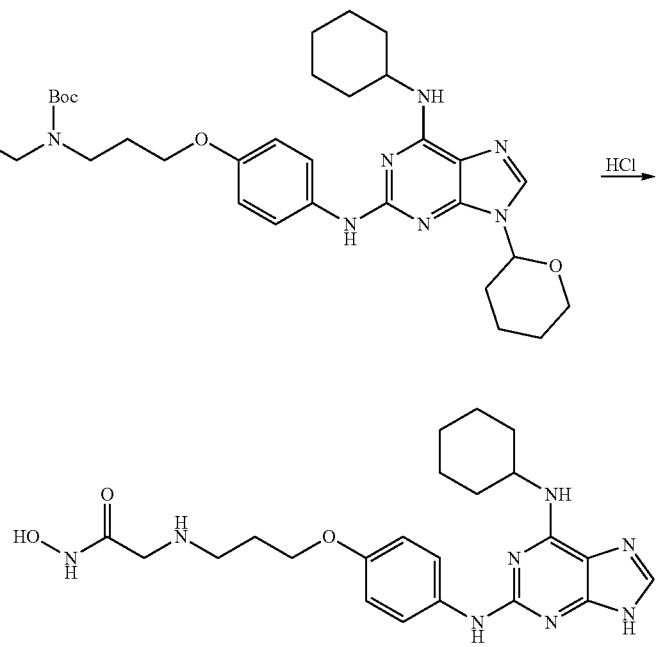

Tert-Butyl 3-(4-(6-(cyclohexylamino)-9-(tetrahydro-2H-pyran-2-yl)-9H-purin-2-ylamino)phenoxy)propyl(2-oxo-2-(tetrahydro-2H-pyran-2-yloxyamino)ethyl)carbamate (40 mg, 0.055 mmole) was dissolved in 1 ml dichloromethane. Then 0.15 ml 4N HCl in dioxane was added and the mixture was stirred at room temperature for 3 hours. Ether was added and the white precipitate was filtered, and washed with ether to get 2-(3-(4-(6-(cyclohexylamino)-9H-purin-2-ylamino)phenoxy)propylamino)-N-hydroxyacetamide hydrochloride salt. Mass Spec(m/z): 455.3 (M+1).

Example 15: Preparation of 2-(4-(4-(6-(cyclohexy-lamino)-9H-purin-2 ylamino)phenyl)piperazin-1-yl)-N-hydroxyacetamide hydrochloride salt Step 1: Preparation of N6-cyclohexyl-N2-(4-(piper-azin-1-yl)phenyl)-9-(tetrahydro-2H-pyran-2-yl)-9H-purine-2,6-diamine

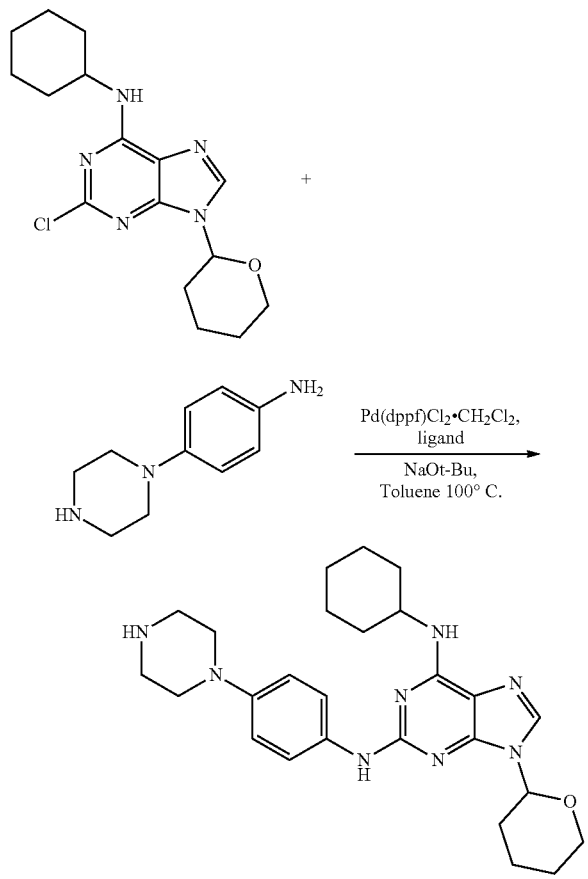

To a solution of 2-chloro-N-cyclohexyl-9-(tetrahydro-2H-pyran-2-yl)-9H-purin-6-amine (0.50 g, 1.5 mmole) in 7.5 ml toluene was added 4-(piperazin-1-yl)aniline (317 mg, 1.8 mmole) and 2-di-tert-butylphosphino-2',4',6'-triisopropylbi-phenyl (63 mg, 0.15 mmole). The reaction mixture was degassed using Argon for 10 min after which Pd(dppf)Cl$_2$ complex with CH$_2$Cl$_2$ (61 mg, 0.075 mmole) was added, followed by sodium t-butoxide (286 mg, 3.0 mmole). The reaction flask was put into a preheated oil-bath at 100° C. and stirred overnight. The mixture was cooled to room temperature. To the mixture, water and EtOAc were added. The layers were separated and the aqueous layer was extracted with EtOAc. The combined organic layer was dried over Na$_2$SO$_4$ and concentrated. The crude product was purified on a silica gel column, eluted EtOAc, then 10% MeOH in EtOAc, then 20% MeOH in EtOAc to get 480 mg (68% yield) of N6-cyclohexyl-N2-(4-(piperazin-1-yl)phe-nyl)-9-(tetrahydro-2H-pyran-2-yl)-9H-purine-2,6-diamine.

Step 2: Preparation of methyl 2-(4-(4-(6-(cyclo-hexylamino)-9-(tetrahydro-2H-pyran-2-yl)-9H-pu-rin-2-ylamino)phenyl)piperazin-1-yl)acetate

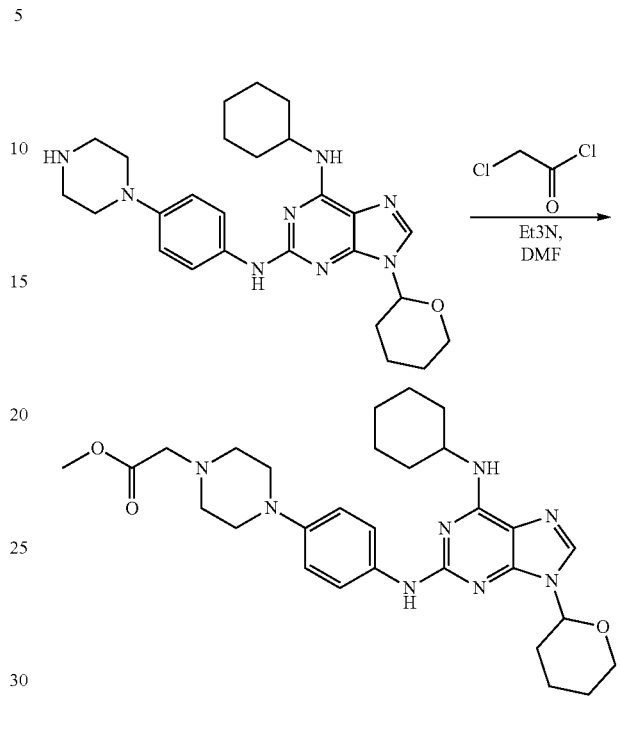

To a solution of N6-cyclohexyl-N2-(4-(piperazin-1-yl) phenyl)-9-(tetrahydro-2H-pyran-2-yl)-9H-purine-2,6-di-amine (87.5 mg, 0.184 mmole) in 1.5 ml dimethyl forma-mide was added triethylamine (74 mg, 0.74 mmole) and methyl chloroacetate (22 mg, 0.20 mmole) were added. The mixture was heated at 40° C. overnight. Water and ethyl acetate were added. The layers were separated and the aqueous layer was extracted with ethyl acetate. The com-bined organic layer was dried with Na$_2$SO$_4$ and concen-trated. Flash chromatography to get the desired product methyl 2-(4-(4-(6-(cyclohexylamino)-9-(tetrahydro-2H-pyran-2-yl)-9H-purin-2-ylamino)phenyl)piperazin-1-yl)ac-etate (80 mg, 80%).

Step 3: Preparation of 2-(4-(4-(6-(cyclohexy-lamino)-9-(tetrahydro-2H-pyran-2-yl)-9H-purin-2-ylamino)phenyl)piperazin-1-yl) acetic acid

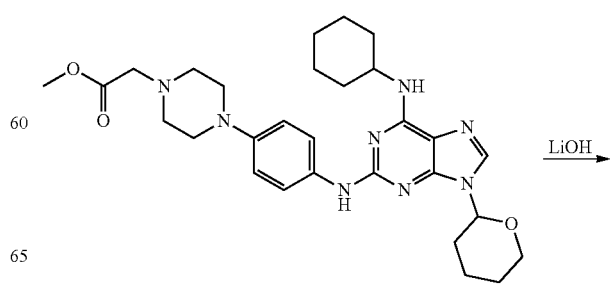

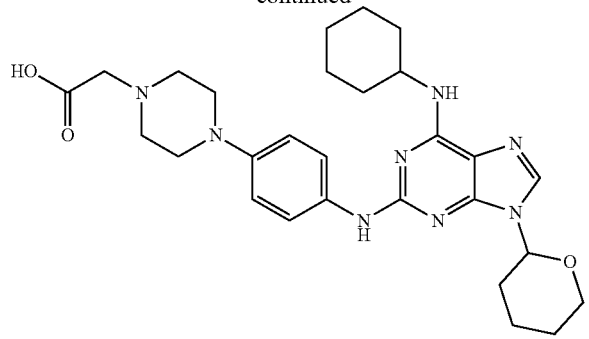

To methyl 2-(4-(4-(6-(cyclohexylamino)-9-(tetrahydro-2H-pyran-2-yl)-9H-purin-2-ylamino)phenyl)piperazin-1-yl) acetate (80 mg, 0.15 mmole) was added 0.7 ml methanol and 0.2 ml water. To the mixture, lithium hydroxide monohydrate (12.3 mg, 0.29 mmole) was added. The reaction was stirred at room temperature overnight. Ethyl acetate and water were added. The aqueous layer was acidified with 1N HCl. The layers were separated and the aqueous layer was extracted with ethyl acetate. The combined organic layer was dried with $Na_2SO_4$ and concentrated. The crude product (70 mg) was used without further purifications.

Step 4: Preparation of 2-(4-(4-(6-(cyclohexylamino)-9-(tetrahydro-2H-pyran-2-yl)-9H-purin-2-ylamino)phenyl)piperazin-1-yl)-N-(tetrahydro-2H-pyran-2-yloxy)acetamide

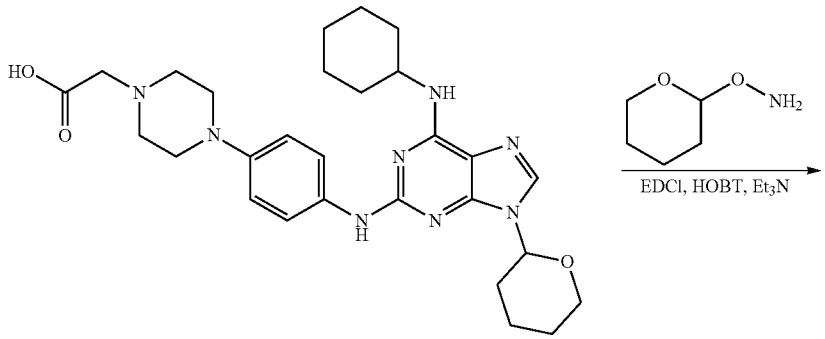

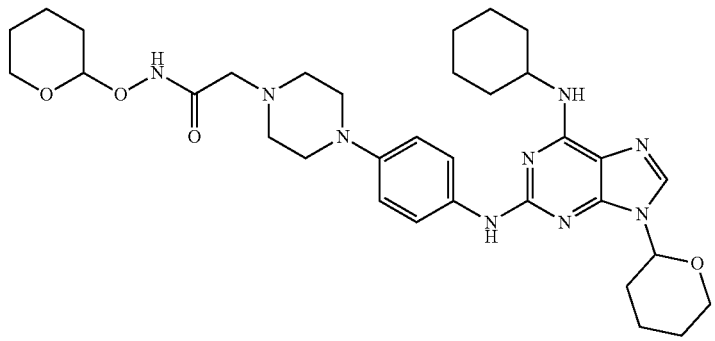

2-(4-(4-(6-(cyclohexylamino)-9-(tetrahydro-2H-pyran-2-yl)-9H-purin-2-ylamino)phenyl)piperazin-1-yl) acetic acid (70 mg, 0.131 mmole) was dissolved in 1 ml dimethyl formamide. 1-Hydroxybenzotriazole monohydrate (26 mg, 0.17 mmole) and N-(3-dimethylaminopropyl)-N'-ethylcarbodiimide hydrochloride (38 mg, 0.20 mmole) were added. After 5 min, triethylamine (53 mg, 0.524 mmole) and O-(tetrahydro-2H-pyran-2-yl)hydroxylamine (17 mg, 0.14 mmole) were added and the mixture was stirred for three hours. To the mixture, water and ethyl acetate were added. The layers were separated and the aqueous layer was extracted with ethyl acetate. The combined organic layer was dried with $Na_2SO_4$ and concentrated. Flash chromatography to get 2-(4-(4-(6-(cyclohexylamino)-9-(tetrahydro-2H-pyran-2-yl)-9H-purin-2-ylamino)phenyl)piperazin-1-yl)-N-(tetrahydro-2H-pyran-2-yloxy)acetamide (6 mg, 7% yield).

Step 5: Preparation of 2-(4-(4-(6-(cyclohexy-lamino)-9H-purin-2-ylamino)phenyl)piperazin-1-yl)-N-hydroxyacetamide hydrochloride salt

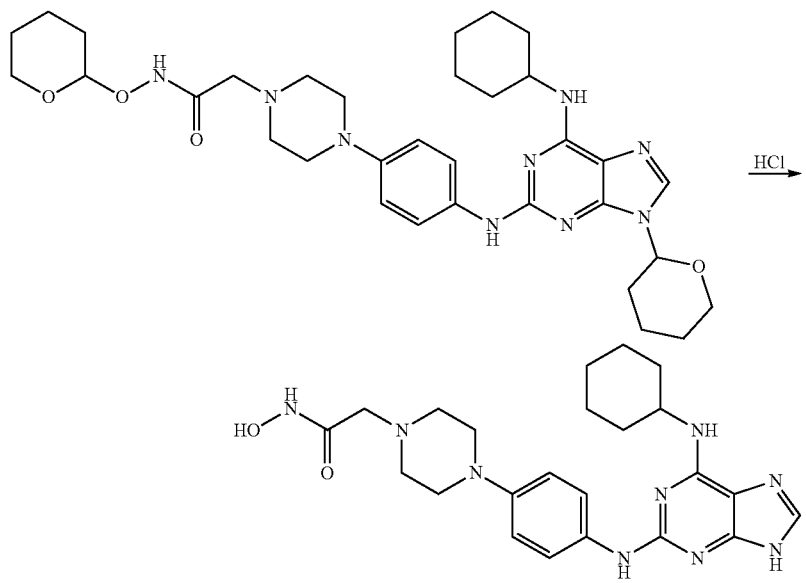

2-(4-(4-(6-(Cyclohexylamino)-9-(tetrahydro-2H-pyran-2-yl)-9H-purin-2-ylamino)phenyl)piperazin-1-yl)-N-(tetrahydro-2H-pyran-2-yloxy)acetamide (6 mg, 0.01 mmole) was dissolved in 0.2 ml methanol. Then 0.2 ml 4N HCl in dioxane was added and the mixture was stirred at room temperature for 2 hours. Solvent was evaporated the mixture was washed with ether to get 2-(4-(4-(6-(cyclohexylamino)-9H-purin-2-ylamino)phenyl)piperazin-1-yl)-N-hydroxyacetamide hydrochloride salt. Mass Spec(m/z): 466.2 (M+1).

Example 16: Preparation of 4-(4-(6-(cyclohexy-lamino)-9H-purin-2-ylamino)phenyl)-N-hydroxypiperazine-1-carboxamide hydrochloride salt Step 1: Preparation of 4-(4-(6-(cyclohexylamino)-9-(tetrahydro-2H-pyran-2-yl)-9H-purin-2-ylamino)phenyl)-N-hydroxypiperazine-1-carboxamide -continued

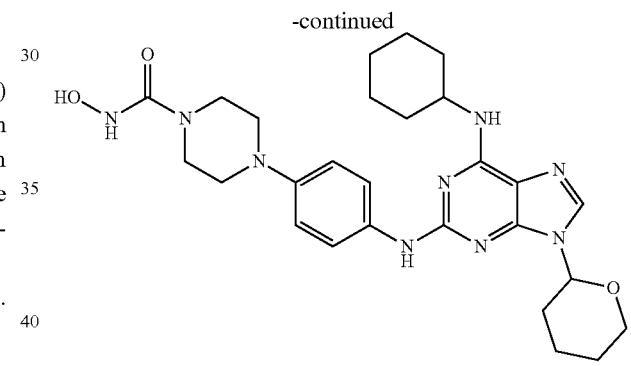

To a solution of N6-cyclohexyl-N2-(4-(piperazin-1-yl)phenyl)-9-(tetrahydro-2H-pyran-2-yl)-9H-purine-2,6-diamine (60 mg, 0.13 mmole) in 1 ml tetrahydrofuran was added phenyl hydroxycarbamate (39 mg, 0.25 mmole). The mixture was heated at 60° C. overnight. Solvent was evaporated. Flash chromatography to get the desired product 4-(4-(6-(cyclohexylamino)-9-(tetrahydro-2H-pyran-2-yl)-9H-purin-2-ylamino)phenyl)-N-hydroxypiperazine-1-carboxamide (22 mg, 32% yield).

Step 2: Preparation of 4-(4-(6-(cyclohexylamino)-9H-purin-2-ylamino)phenyl)-N-hydroxypiperazine-1-carboxamide hydrochloride salt

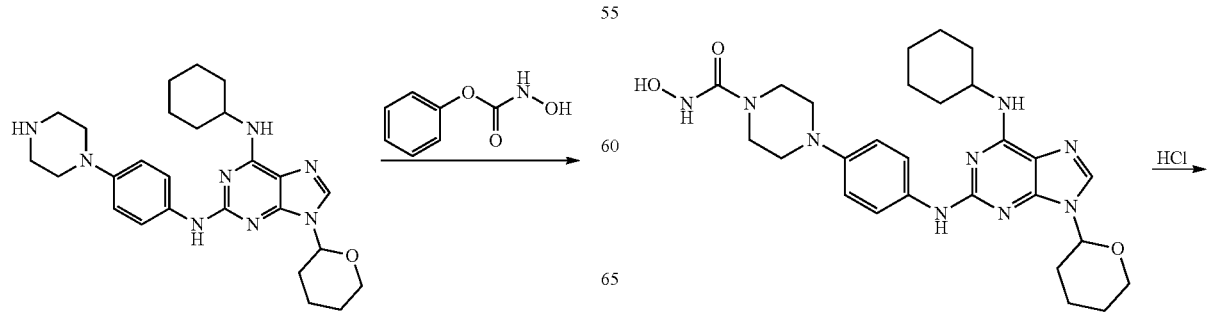

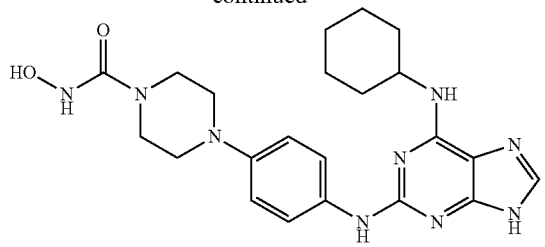

4-(4-(6-(cyclohexylamino)-9-(tetrahydro-2H-pyran-2-yl)-9H-purin-2-ylamino)phenyl)-N-hydroxypiperazine-1-carboxamide (22 mg, 0.041 mmole) was dissolved in 0.165 ml methanol. Then 0.165 ml 4N HCl in dioxane was added and the mixture was stirred at room temperature overnight. Solvent was evaporated. Ether was added and the precipitate was washed with ether to get 4-(4-(6-(cyclohexylamino)-9H-purin-2-ylamino)phenyl)-N-hydroxypiperazine-1-carboxamide hydrochloride salt. Mass Spec(m/z): 452.2 (M+1).

Example 17: Preparation of 7-(4-((6-(tert-butylamino)-9H-purin-2-yl)amino)phenoxy)-N-hydroxyheptanamide Step 1: Preparation of N-(tert-butyl)-2-chloro-9-(tetrahydro-2H-pyran-2-yl)-9H-purin-6-amine

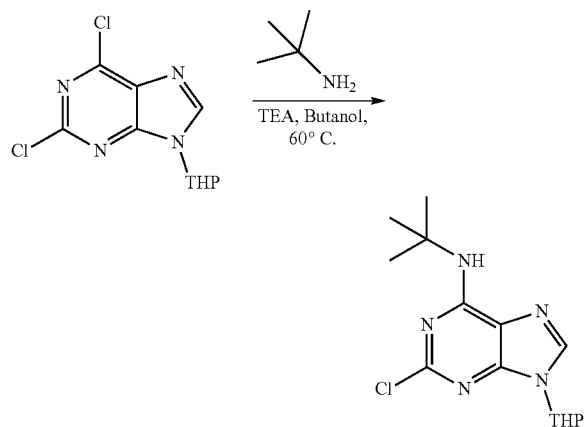

A mixture of 2, 6-dichloro-9-(tetrahydro-2H-pyran-2-yl)-9H-purine (2.0 g, 7.3 mol) and tert-Butylamine (0.58 g, 7.9 mmol) in butanol (10 mL) and TEA (1.5 g, 14.6 mmol) was heated to 60° C. and stirred for 3 hrs. Then the mixture was poured in water and extracted with EtOAc. The organic layer was dried and concentrated. The residue was purified by column to give an oil (1.2 g, 53%).

Step 2: Preparation of methyl 7-(4-((6-(tert-butylamino)-9-(tetrahydro-2H-pyran-2-yl)-9H-purin-2-yl)amino)phenoxy)heptanoate

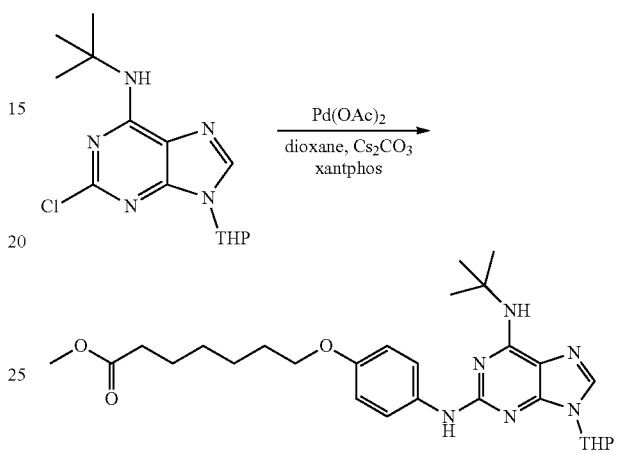

To a solution of N-(tert-butyl)-2-chloro-9-(tetrahydro-2H-pyran-2-yl)-9H-purin-6-amine (1.0 g, 3.24 mmol) in dioxane (10 mL) was added methyl 7-(4-aminophenoxy)heptanoate (analogous to Example 2; step 1 alternative procedure) (0.9 g, 3.56 mmol), xantphos (188 mg, 0.324 mmol), Cs₂CO₃ (1.58 g, 4.86 mmol) and Pd(OAc)₂ (72.7 mg, 0.324 mol). The mixture was degassed using argon for 10 min. The reaction flask was put into a preheated oil-bath at 80° C. and stirred overnight. The mixture was cooled to r.t and extracted with DCM and washed with sat. NH₄Cl aq. Purification with column chromatography gave methyl 7-(4-((6-(tert-butylamino)-9-(tetrahydro-2H-pyran-2-yl)-9H-purin-2-yl)amino)phenoxy)heptanoate as a brown solid (1.2 g, 70%).

Step 3: Preparation of 7-(4-((6-(tert-butylamino)-9-(tetrahydro-2H-pyran-2-yl)-9H-purin-2-yl)amino)phenoxy)heptanoic acid

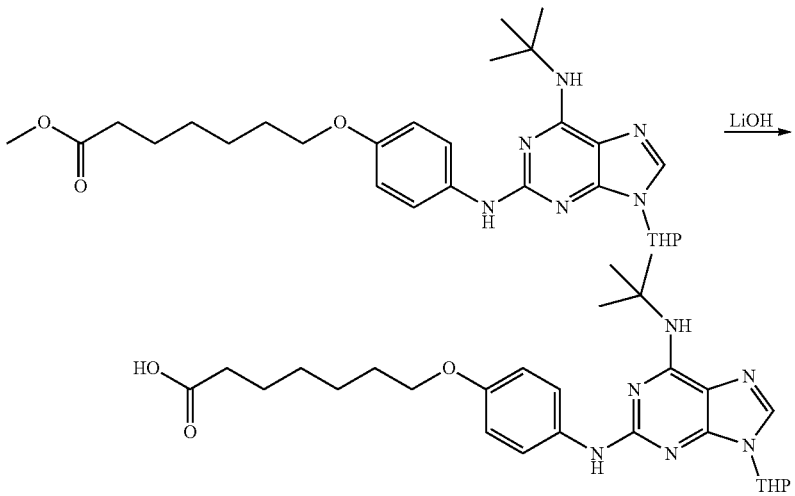

To the solution of methyl 7-(4-((6-(tert-butylamino)-9-(tetrahydro-2H-pyran-2-yl)-9H-purin-2-yl)amino)phenoxy)heptanoate (0.6 g, 1.17 mmol) in THF (10 mL) and water (2 mL) was added lithium hydroxide monohydrate (200 mg, 4.76 mmol) at r.t. The mixture was stirred for 4 hrs. EtOAc was added and washed with dilute HCl. The organic layer was dried and concentrated to give crude 7-(4-((6-(tert-butylamino)-9-(tetrahydro-2H-pyran-2-yl)-9H-purin-2-yl)amino)phenoxy)heptanoic acid (0.50 g) which was used without further purification.

Step 4: Preparation of 7-(4-((6-(tert-butylamino)-9-(tetrahydro-2H-pyran-2-yl)-9H-purin-2-yl)amino)phenoxy)-N-((tetrahydro-2H-pyran-2-yl)oxy)heptanamide

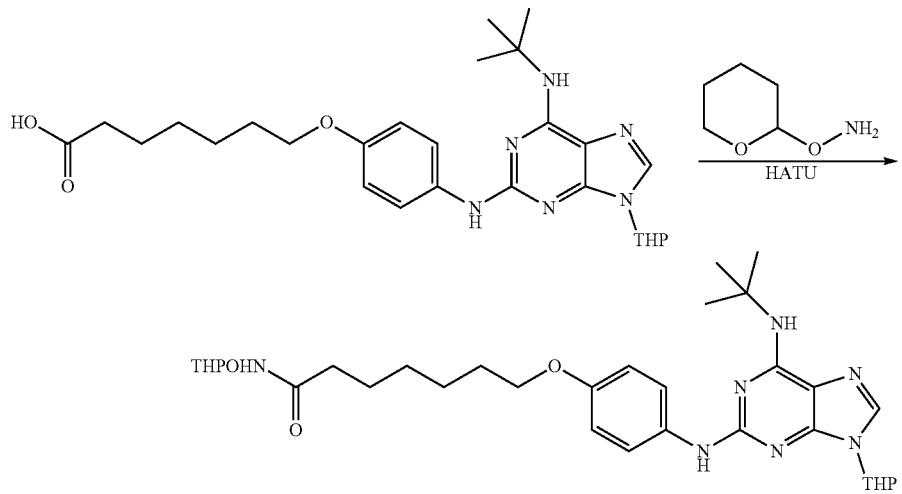

To the solution of 7-(4-((6-(tert-butylamino)-9-(tetrahydro-2H-pyran-2-yl)-9H-purin-2-yl)amino)phenoxy)heptanoic acid (0.5 g) and O-(Tetrahydro-pyran-2-yl)-hydroxylamine (137 mg, 1.17 mmol) in DMF was added TEA (297 mg, 2.94 mmol) and HATU (0.56 g, 1.47 mol) at r.t. and stirred overnight. To the mixture, water and EtOAc were added. The aqueous layer was extracted twice; the organic layer was dried, concentrated, and purified by column chromatography to give 7-(4-((6-(tert-butylamino)-9-(tetrahydro-2H-pyran-2-yl)-9H-purin-2-yl)amino)phenoxy)-N-((tetrahydro-2H-pyran-2-yl)oxy)heptanamide (0.41 g) as a solid.

Step 5: Preparation of 7-(4-((6-(tert-butylamino)-9H-purin-2-yl)amino)phenoxy)-N-hydroxyheptanamide

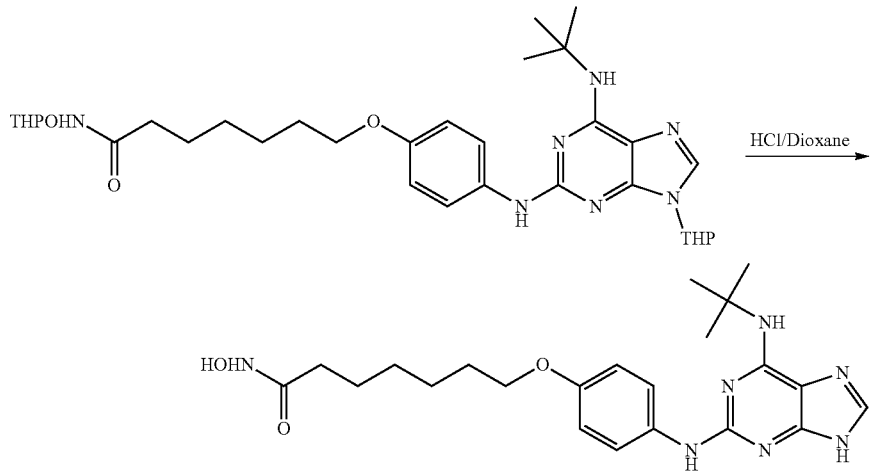

To the solution of 7-(4-((6-(tert-butylamino)-9-(tetrahydro-2H-pyran-2-yl)-9H-purin-2-yl)amino)phenoxy)-N-((tetrahydro-2H-pyran-2-yl)oxy)heptanamide (0.4 g) in DCM (10 mL) was added HCl/Dioxane (10 mL, 4 mol/L). The mixture was stirred for 4 hrs at r.t. MTBE was added and stirred for 30 min. The suspension was filtrated, filtrated cake was dried and purified by preparative HPLC to give 7-(4-((6-(tert-butylamino)-9H-purin-2-yl)amino)phenoxy)-N-hydroxyheptanamide (0.13 g). Mass Spec(m/z): 442.2 (M+1).

Example 18: Preparation of 7-(4-((7-(cyclohexylamino)-3H-imidazo[4,5-b]pyridin-5-yl)amino)phenoxy)-N-hydroxyheptanamide Step 1: Preparation of 5,7-dichloro-3-(tetrahydro-2H-pyran-2-yl)-3H-imidazo[4,5-b]pyridine

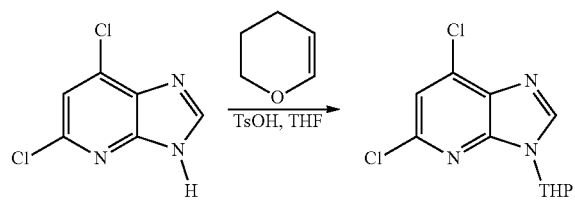

Synthesized according to the procedure described above in Example 1, Step 1. Purification by column chromatography gave 5,7-dichloro-3-(tetrahydro-2H-pyran-2-yl)-3H-imidazo[4,5-b]pyridine as a gray solid (0.8 g, 55%).

Step 2: Preparation of 5-chloro-N-cyclohexyl-3-(tetrahydro-2H-pyran-2-yl)-3H-imidazo[4,5-b]pyridin-7-amine

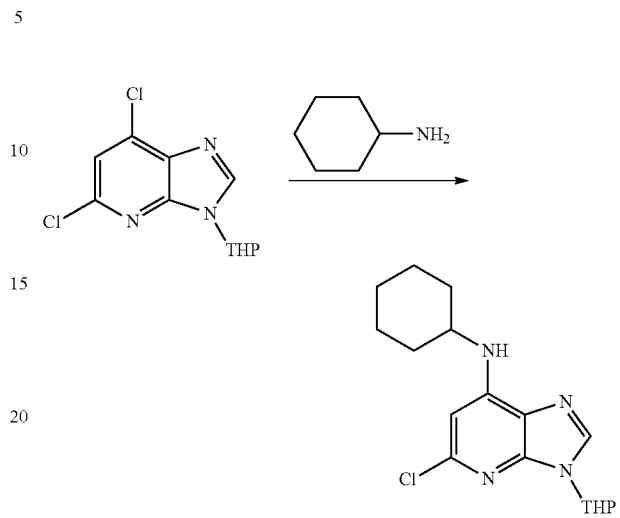

Synthesized according to the procedure described above in Example 1, Step 2 Purification by column chromatography gave 5-chloro-N-cyclohexyl-3-(tetrahydro-2H-pyran-2-yl)-3H-imidazo[4,5-b]pyridin-7-amine as an oil (0.8 g, 65%).

Step 3: Preparation of methyl 7-(4-((7-(cyclohexylamino)-3-(tetrahydro-2H-pyran-2-yl)-3H-imidazo[4,5-b]pyridin-5-yl)amino)phenoxy)heptanoate

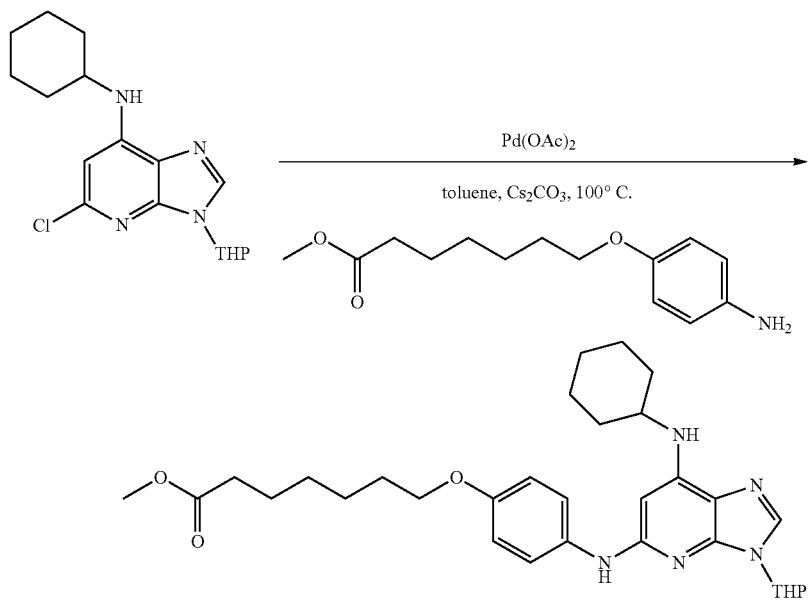

Synthesized according to the procedure described above in Example 17, Step 2 Purification by column chromatography gave methyl 7-(4-((7-(cyclohexylamino)-3-(tetrahydro-2H-pyran-2-yl)-3H-imidazo[4,5-b]pyridin-5-yl)amino)phenoxy)heptanoate (0.6 g).

Step 4: Preparation of: 7-(4-((7-(cyclohexylamino)-3-(tetrahydro-2H-pyran-2-yl)-3H-imidazo[4,5-b]pyridin-5-yl)amino)phenoxy)heptanoic acid

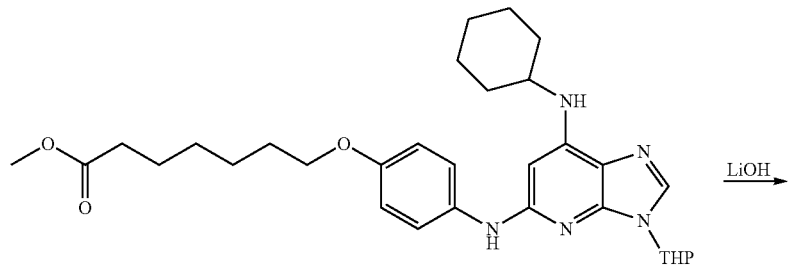

Synthesized according to the procedure described above in Example 17, Step 3. It gave 7-(4-((7-(cyclohexylamino)-3-(tetrahydro-2H-pyran-2-yl)-3H-imidazo[4,5-b]pyridin-5-yl)amino)phenoxy)heptanoic acid as an oil (0.4 g, crude).

Step 5: Preparation of 7-(4-((7-(cyclohexylamino)-3-(tetrahydro-2H-pyran-2-yl)-3H-imidazo[4,5-b]pyridin-5-yl)amino)phenoxy)-N-((tetrahydro-2H-pyran-2-yl)oxy)heptanamide

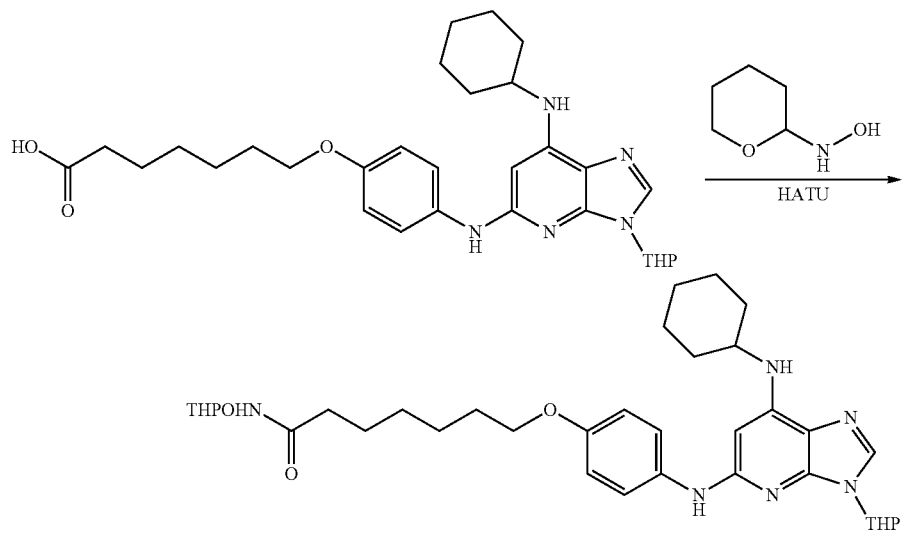

Synthesized according to the procedure described above in Example 17, Step 4. Purification by column chromatography gave 7-(4-((7-(cyclohexylamino)-3-(tetrahydro-2H-pyran-2-yl)-3H-imidazo[4,5-b]pyridin-5-yl)amino)phenoxy)-N-((tetrahydro-2H-pyran-2-yl)oxy)heptanamide as an oil (0.3 g, 65%).

Step 6: Preparation of 7-(4-((7-(cyclohexylamino)-3H-imidazo[4,5-b]pyridin-5-yl)amino)phenoxy)-N-hydroxyheptanamide

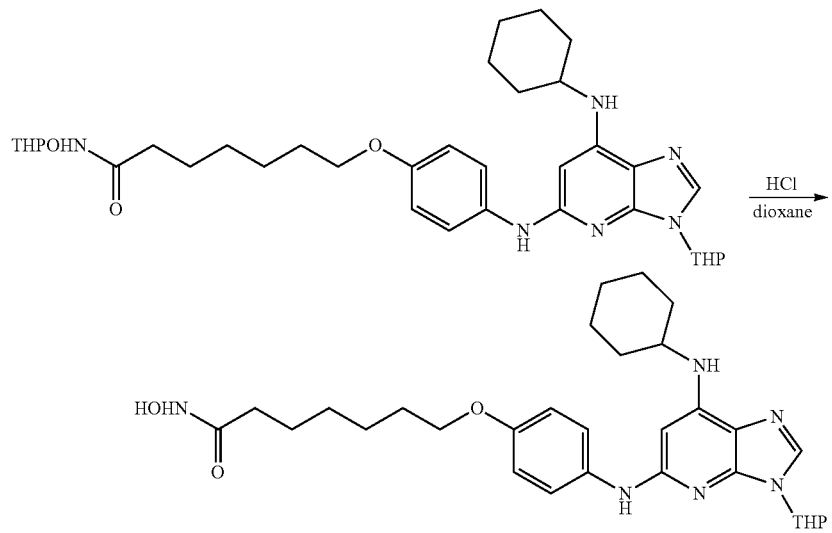

Synthesized according to the procedure described above in Example 17, Step 5. Purification by preparative HPLC gave 7-(4-((7-(cyclohexylamino)-3H-imidazo[4,5-b]pyridin-5-yl)amino)phenoxy)-N-hydroxyheptanamide as an oil (0.3 g, 64.7%). Mass Spec(m/z): 467.2 (M+1).

Example 19: Preparation of: methyl 7-((4-aminophenyl)thio)heptanoate

Step 1: Preparation of tert-butyl (4-mercaptophenyl)carbamate

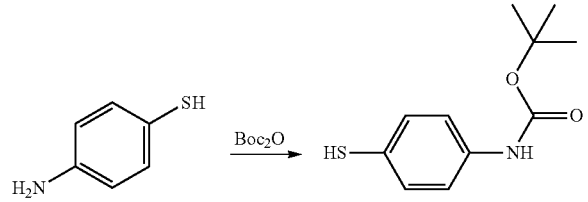

To a solution of 4-aminobenzenethiol (5.0 g, 40 mmol) and TEA (8.08 g, 80 mmol) in MeOH (50 mL) was added Boc$_2$O (9.6 g, 1.1 eq.) portion wise at 0-5° C. After addition, the mixture was stirred at r.t for 2 hrs. The mixture was poured into water, extracted with MTBE, dried, concentrated and purified by column chromatography to give tert-butyl (4-mercaptophenyl)carbamate (6.0 g, 67%)

Step 2: Preparation of methyl 7-((4-((tert-butoxycarbonyl)amino)phenyl)thio)heptanoate

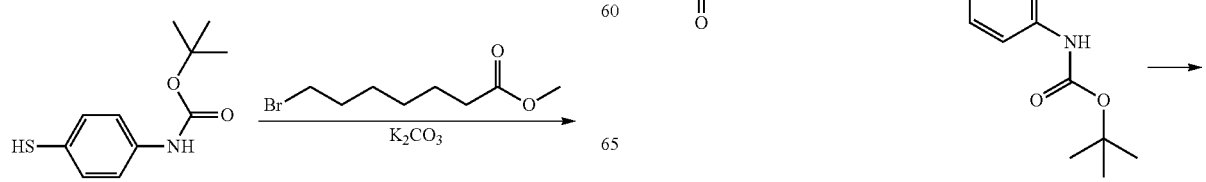

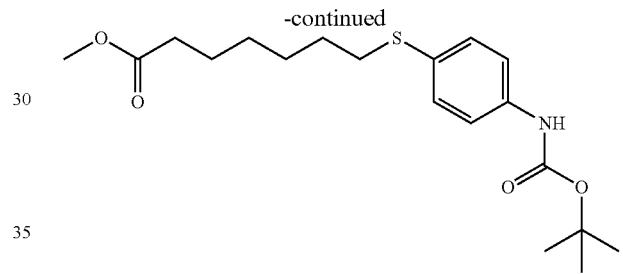

A mixture of tert-butyl (4-mercaptophenyl)carbamate (4.5 g, 20 mol), 7-Bromo-heptanoic acid methyl ester (4.4 g, 21 mmol) and K$_2$CO$_3$ (5.5 g, 40 mmol) was heated at 80-90° C. and stirred overnight. The mixture was cooled, concentrated, the residue was dissolved in MTBE, washed with brine, dried, concentrated and purified by column chromatography to give methyl 7-((4-((tert-butoxycarbonyl)amino)phenyl)thio)heptanoate as a white solid (3.1 g, 41%).

Step 3: Preparation of methyl 7-((4-aminophenyl)thio)heptanoate

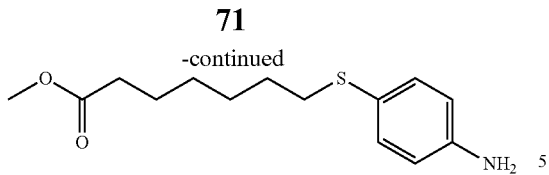

To a solution of 7-((4-((tert-butoxycarbonyl)amino)phenyl)thio)heptanoate (3.0 g, 8.17 mmol) in DCM (30 mL) was added TFA (6 mL) dropwise at 0-5° C. The mixture was stirred for 4 hrs at r.t. and poured into aq. NaHCO$_3$ solution. The mixture was extracted with EtOAc, dried and concentrated to give methyl 7-((4-aminophenyl)thio)heptanoate as a brown solid (1.6 g, 73.4%) which was used without further purification.

Example 20: Preparation of 7-((4-((6-(cyclohexylamino)-9H-purin-2-yl)amino)phenyl)thio)-N-hydroxyheptanamide

Step 1: Preparation of methyl 7-((4-((6-(cyclohexylamino)-9-(tetrahydro-2H-pyran-2-yl)-9H-purin-2-yl)amino)phenyl)thio)heptanoate

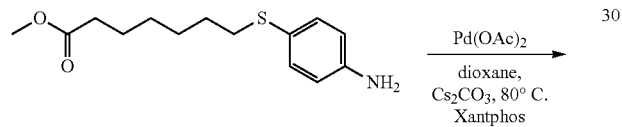

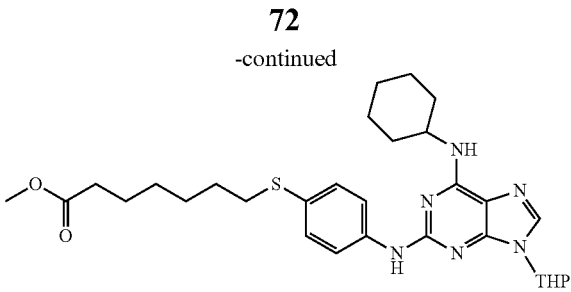

To a solution of methyl 7-((4-aminophenyl)thio)heptanoate (1.0 g, 3.74 mmol) in dioxane (10 mL) was added 2-chloro-N-cyclohexyl-9-(tetrahydro-2H-pyran-2-yl)-9H-purin-6-amine (1.25 g, 3.74 mmol), Xantphos (216 mg, 0.374 mmol), Cs$_2$CO$_3$ (1.84 g, 5.6 mmol) and Pd(OAc)$_2$ (84 g, 0.374 mol). The mixture was degassed using argon for 10 min. The reaction flask was put into a preheated oil-bath at 80° C. and stirred overnight. The mixture was cooled to r.t and extracted with DCM and washed with sat. NH$_4$Cl aq., organic layer was dried, concentrated and purified to give brown solid (0.6 g, 27%).

Step 2: Preparation of 7-((4-((6-(cyclohexylamino)-9-(tetrahydro-2H-pyran-2-yl)-9H-purin-2-yl)amino)phenyl)thio)heptanoic acid

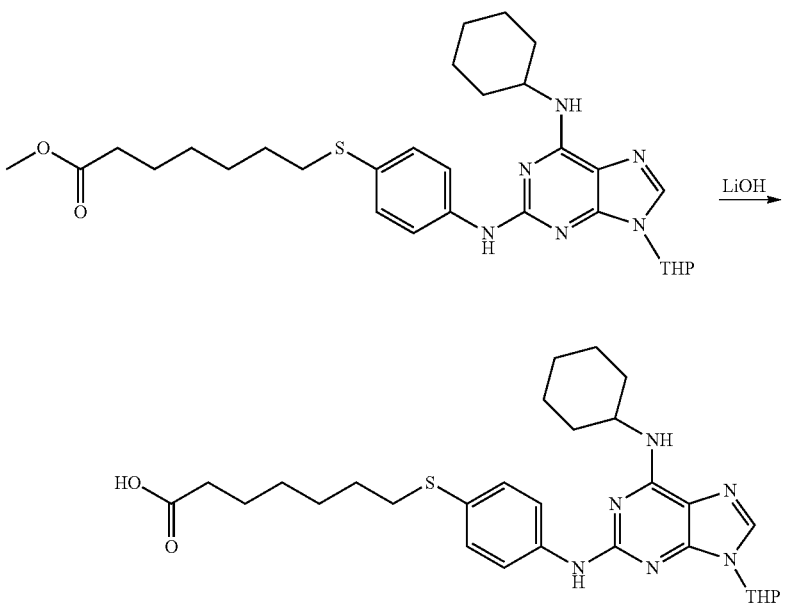

Synthesized according to the procedure described above in Example 17, Step 3. The crude product, 7-((4-((6-(cyclohexylamino)-9-(tetrahydro-2H-pyran-2-yl)-9H-purin-2-yl)amino)phenyl)thio)heptanoic acid was used without further purification (0.4 g).

Step 3: Preparation of: 7-((4-((6-(cyclohexylamino)-9-(tetrahydro-2H-pyran-2-yl)-9H-purin-2-yl)amino)phenyl)thio)-N-((tetrahydro-2H-pyran-2-yl)oxy)heptanamide

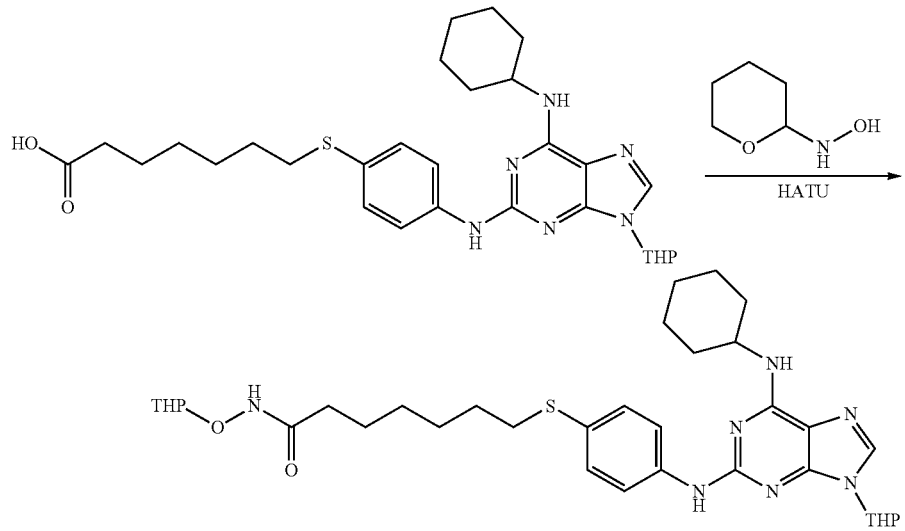

Synthesized according to the procedure described above in Example 17, Step 4. Purification by column chromatography gave 7-((4-((6-(cyclohexylamino)-9-(tetrahydro-2H-pyran-2-yl)-9H-purin-2-yl)amino)phenyl)thio)-N-((tetrahydro-2H-pyran-2-yl)oxy)heptanamide (0.32 g).

Step 4: Preparation of 7-((4-((6-(cyclohexylamino)-9H-purin-2-yl)amino)phenyl)thio)-N-hydroxyheptanamide

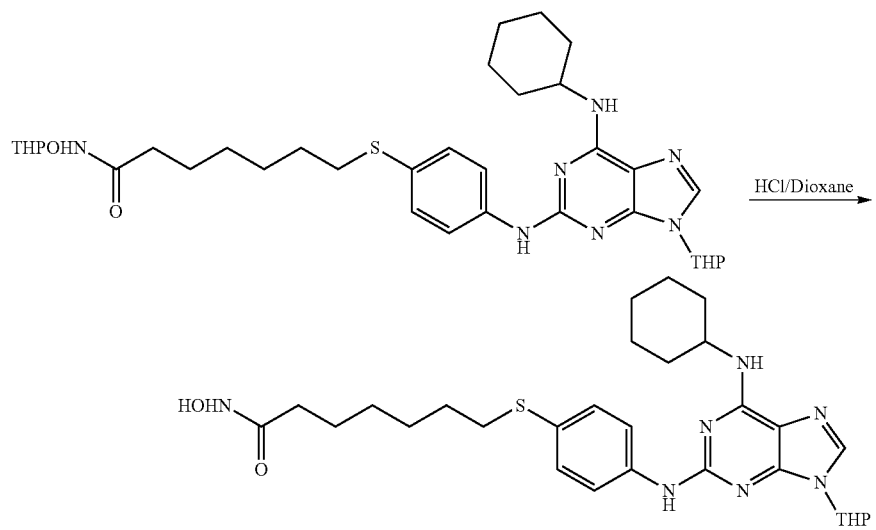

Synthesized according to the procedure described above in Example 17, Step 5. Purification by preparative HPLC gave 7-((4-((6-(cyclohexylamino)-9H-purin-2-yl)amino)phenyl)thio)-N-hydroxyheptanamide (0.10 g). Mass Spec (m/z): 484.1 (M+1).

Example 21: Preparation of 7-((4-((6-(cyclohexylamino)-9H-purin-2-yl)amino)phenyl)sulfonyl)-N-hydroxyheptanamide

Step 1: Preparation of methyl 7-((4-((6-(cyclohexylamino)-9-(tetrahydro-2H-pyran-2-yl)-9H-purin-2-yl)amino)phenyl)sulfonyl)heptanoate

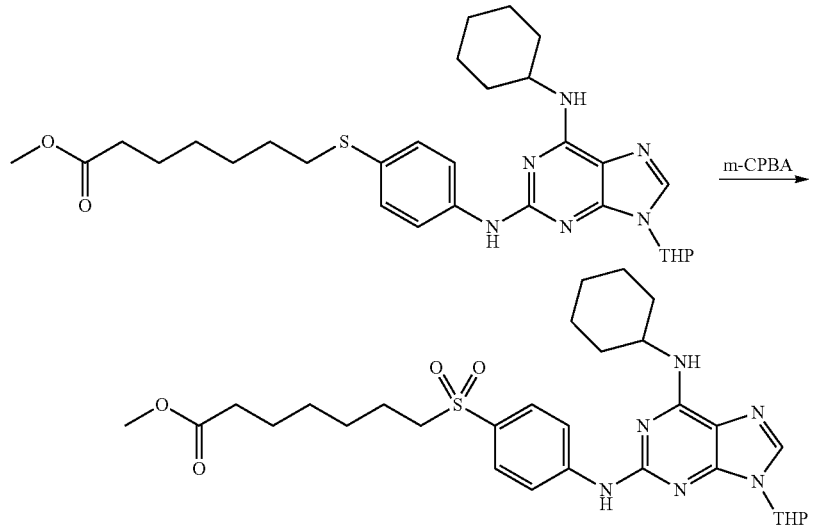

To a solution of methyl 7-((4-((6-(cyclohexylamino)-9-(tetrahydro-2H-pyran-2-yl)-9H-purin-2-yl)amino)phenyl)thio)heptanoate (0.59 g) in DCM (20 mL) was added mCPBA (0.42 g) at 0-5° C. and the reaction was slowly warmed up to r.t. and stirred overnight. The mixture was washed sequentially with aq. NaHSO₃ solution and aq. Na₂CO₃ solution. The organic layer was dried and concentrated to give methyl 7-((4-((6-(cyclohexylamino)-9-(tetrahydro-2H-pyran-2-yl)-9H-purin-2-yl)amino)phenyl)sulfonyl)heptanoate (0.60 g) which was used without further purification.

Step 2: Preparation of 7-((4-((6-(cyclohexylamino)-9-(tetrahydro-2H-pyran-2-yl)-9H-purin-2-yl)amino)phenyl)sulfonyl)heptanoic acid

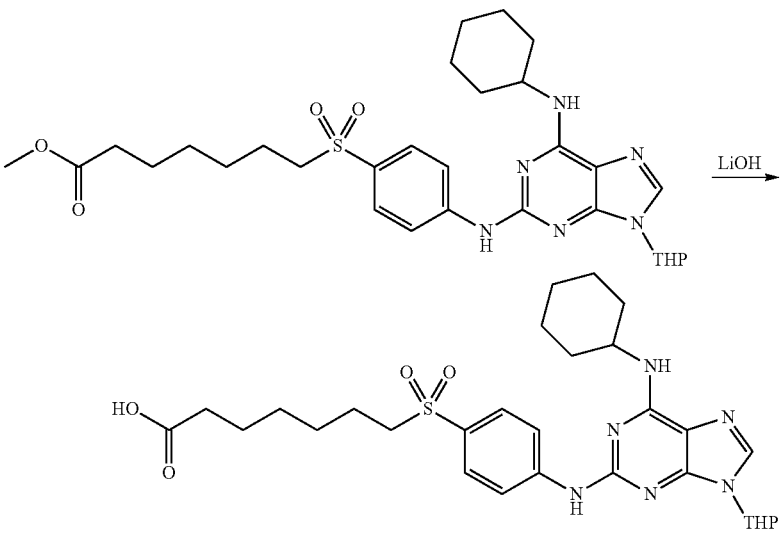

Synthesized according to the procedure described above in Example 17, Step 3. The crude product.
7-((4-((6-(cyclohexylamino)-9-(tetrahydro-2H-pyran-2-yl)-9H-purin-2-yl)amino)phenyl)sulfonyl)heptanoic acid (0.38 g), was used without further purification.

Step 3: Preparation of 7-((4-(((6-(cyclohexylamino)-9-(tetrahydro-2H-pyran-2-yl)-9H-purin-2-yl)amino)phenyl)sulfonyl)-N-((tetrahydro-2H-pyran-2-yl)oxy)heptanamide

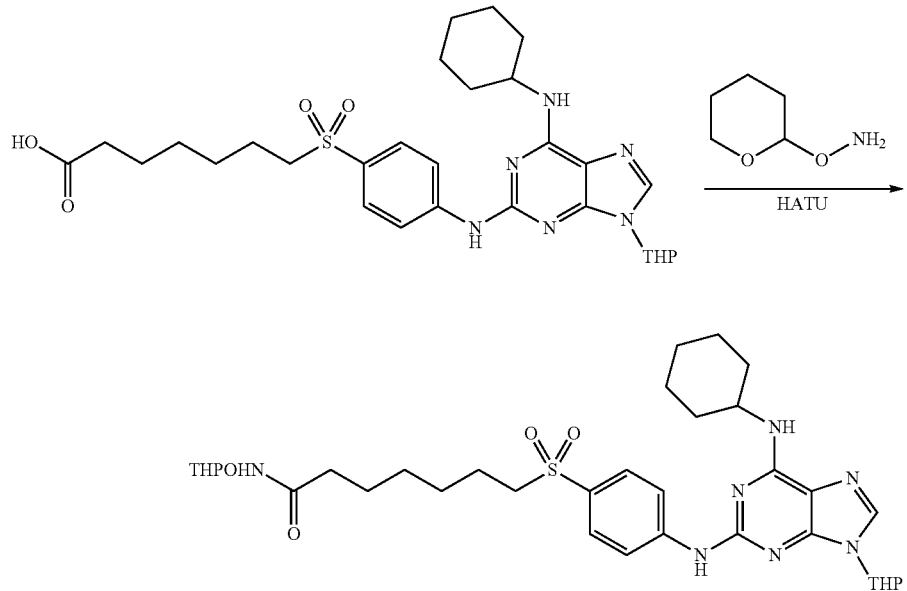

Synthesized according to the procedure described above in Example 17, Step 4. Purification by column chromatography gave 7-((4-(((6-(cyclohexylamino)-9-(tetrahydro-2H-pyran-2-yl)-9H-purin-2-yl)amino)phenyl)sulfonyl)-N-((tetrahydro-2H-pyran-2-yl)oxy)heptanamide (0.41 g).

Step 4: Preparation of 7-((4-(((6-(cyclohexylamino)-9H-purin-2-yl)amino)phenyl)sulfonyl)-N-hydroxyheptanamide

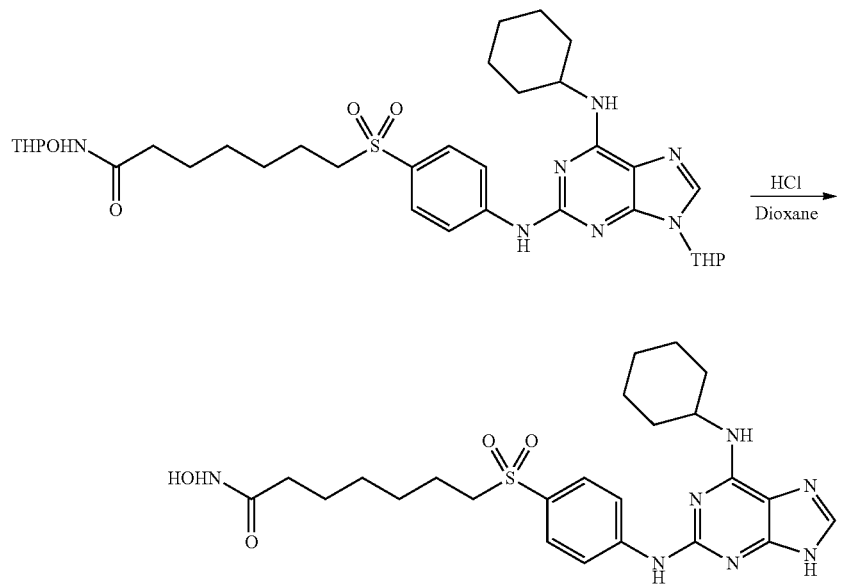

Synthesized according to the procedure described above in Example 17, Step 5 Purification by preparative HPLC gave 7-((4-((6-(cyclohexylamino)-9H-purin-2-yl)amino)phenyl)sulfonyl)-N-hydroxyheptanamide as a white solid (0.12 g). Mass Spec(m/z): 516.2 (M+1).

Example 22: Preparation of methyl 8-(4-aminophenyl)octanoate

Step 1: Preparation of (E)-methyl 8-(4-nitrophenyl)oct-7-enoate

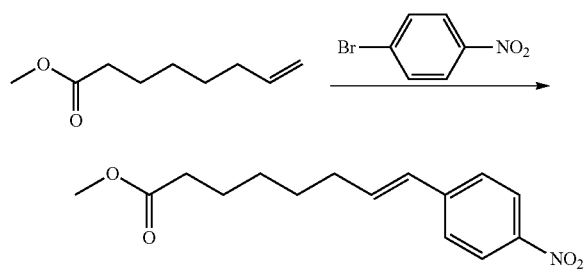

To a solution of methyl oct-7-enoate (1.8 g, 11.53 mmol) in dioxane (10 mL) was added 1-Bromo-4-nitro-benzene (1.43 g, 5.77 mmol), xantphos (1.32 g, 2.3 mmol), KOAc (1.692 g, 17.3 mmol) and Pd(OAc)$_2$ (258.3 mg, 1.15 mol). The mixture was degassed using argon for 5 min. and the reaction flask was placed into a preheated oil-bath at 80° C. and stirred overnight. The mixture was cooled to r.t, quenched with water and extracted with DCM. The combined extracts were washed with sat. aq. NH$_4$Cl solution, dried, concentrated and the residue was purified by column chromatography to give methyl 8-(4-aminophenyl)octanoate as an oil (1.1 g, 68%).

Step 2: Preparation of methyl 8-(4-aminophenyl)octanoate

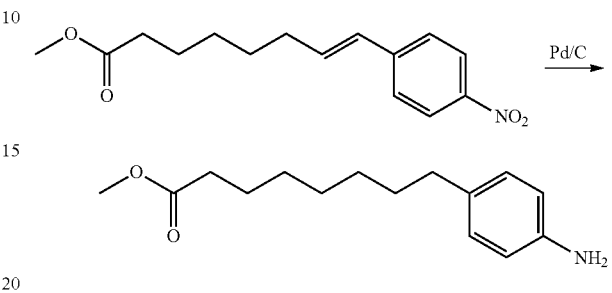

A mixture of methyl 8-(4-aminophenyl)octanoate (1.1 g, 3.97 mmol) and Pd/C (200 mg) in MeOH (10 mL) was stirred under an H$_2$ atmosphere at r.t overnight. The suspension was then filtered, concentrated and the residue purified by column chromatography to give methyl 8-(4-aminophenyl)octanoate (0.4 g, 40%) as colorless oil.

Example 23: Preparation of 8-(4-((6-(cyclohexylamino)-9H-purin-2-yl)amino)phenyl)-N-hydroxyoctanamide Step 1: Preparation of methyl 8-(4-((6-(cyclohexylamino)-9-(tetrahydro-2H-pyran-2-yl)-9H-purin-2-yl)amino)phenyl)octanoate

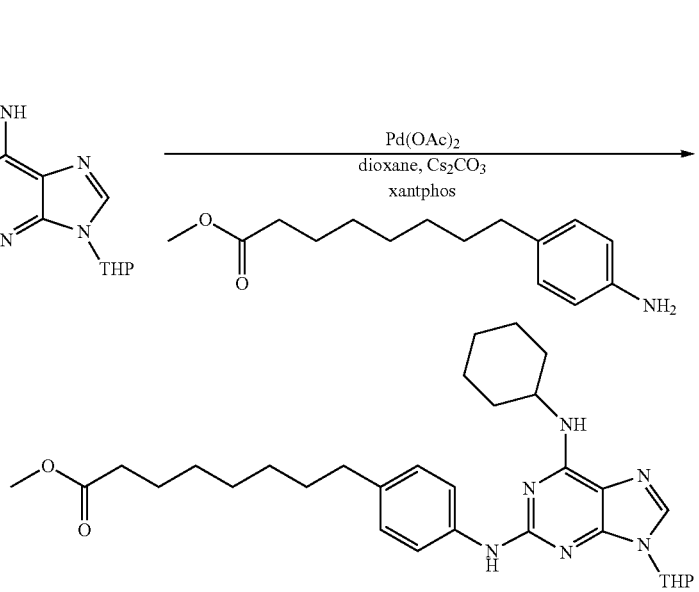

Synthesized according to the procedure described above in Example 17, Step 2. Purification by column chromatography gave methyl 8-(4-((6-(cyclohexylamino)-9-(tetrahydro-2H-pyran-2-yl)-9H-purin-2-yl)amino)phenyl)octanoate as a brown solid (0.4 g, 37%).

Step 2: Preparation of 8-(4-((6-(cyclohexylamino)-
9-(tetrahydro-2H-pyran-2-yl)-9H-purin-2-yl)amino)
phenyl)octanoic acid

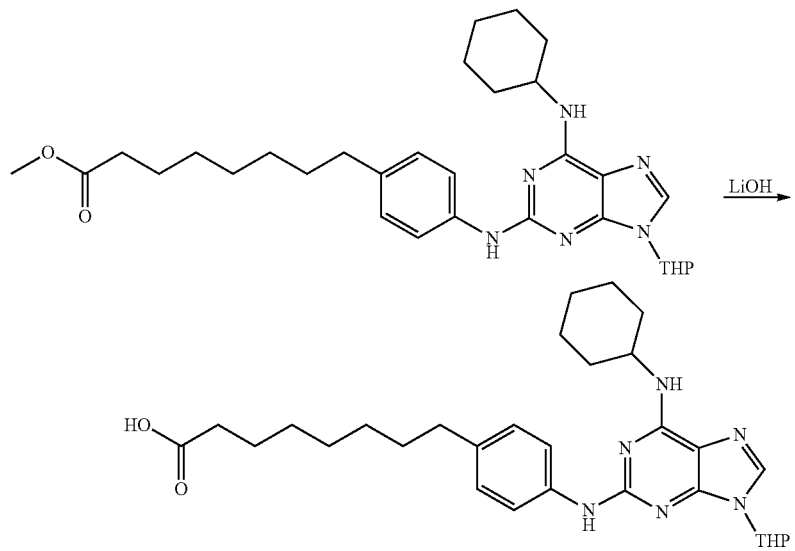

Synthesized according to the procedure described above in Example 17, Step 3. The crude product 8-(4-((6-(cyclohexylamino)-9-(tetrahydro-2H-pyran-2-yl)-9H-purin-2-yl)amino)phenyl)octanoic acid (0.6 g). was used without further purification.

Step 3: Preparation of 8-(4-((6-(cyclohexylamino)-
9-(tetrahydro-2H-pyran-2-yl)-9H-purin-2-yl)amino)
phenyl)-N-((tetrahydro-2H-pyran-2-yl)oxy)octana-
mide

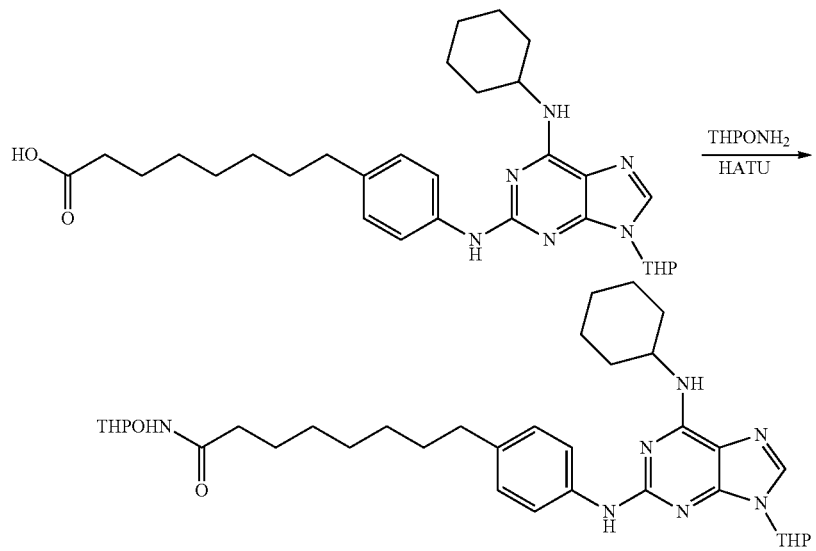

Synthesized according to the procedure described above in Example 17, Step 4. Purification by column chromatography gave 8-(4-((6-(cyclohexylamino)-9-(tetrahydro-2H-pyran-2-yl)-9H-purin-2-yl)amino)phenyl)-N-((tetrahydro-2H-pyran-2-yl)oxy)octanamide (0.35 g)

Step 4: Preparation of 8-(4-((6-(cyclohexylamino)-9H-purin-2-yl)amino)phenyl)-N-hydroxyoctanamide

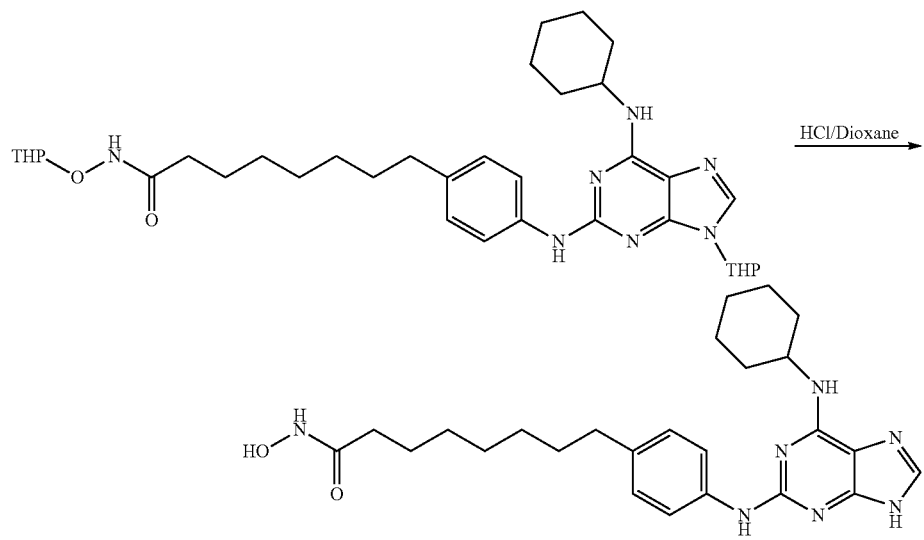

Synthesized according to the procedure described above in Example 17, Step 5. Purification by preparative HPLC gave 8-(4-((6-(cyclohexylamino)-9H-purin-2-yl)amino)phenyl)-N-hydroxyoctanamide as a white solid (0.15 g). Mass Spec(m/z): 466.3 (M+1).

Example 24: Preparation of 7-(4-((9H-purin-2-yl)amino)phenoxy)-N-hydroxyheptanamide Step 1: Preparation of 2-chloro-9-(tetrahydro-2H-pyran-2-yl)-9H-purine

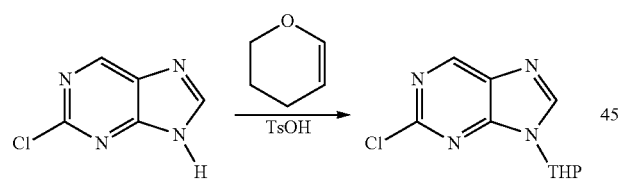

Synthesized according to the procedure described above in Example 1, Step 1. Purification by column chromatography gave a gray solid (1.0 g, 42%).

Step 2: Preparation of methyl 7-(4-((9-(tetrahydro-2H-pyran-2-yl)-9H-purin-2-yl)amino)phenoxy)heptanoate

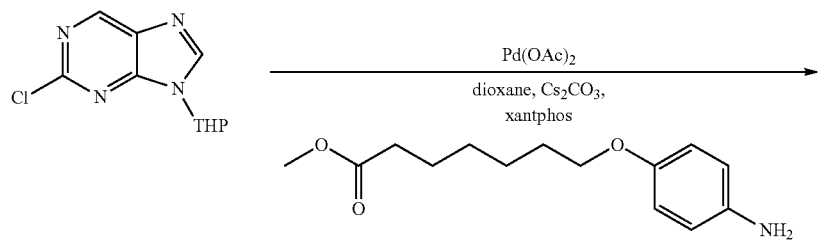

-continued

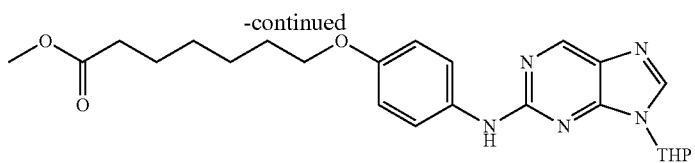

Synthesized according to the procedure described above in Example 17, Step 2. Purification by column chromatography gave brown solid (0.8 g, 70%).

Step 3: Preparation of 7-(4-((9-(tetrahydro-2H-pyran-2-yl)-9H-purin-2-yl)amino)phenoxy)heptanoic acid

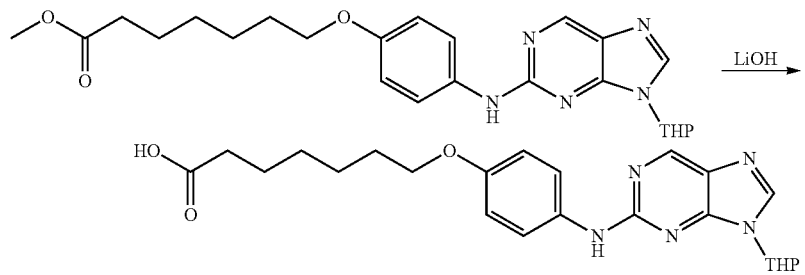

Synthesized according to the procedure described above in Example 17, Step 3. The crude product 7-(4-((9-(tetrahydro-2H-pyran-2-yl)-9H-purin-2-yl)amino)phenoxy)heptanoic acid was used without further purification (0.6 g).

Step 4: Preparation of 7-(4-((9-(tetrahydro-2H-pyran-2-yl)-9H-purin-2-yl)amino)phenoxy)-N-((tetrahydro-2H-pyran-2-yl)oxy)heptanamide

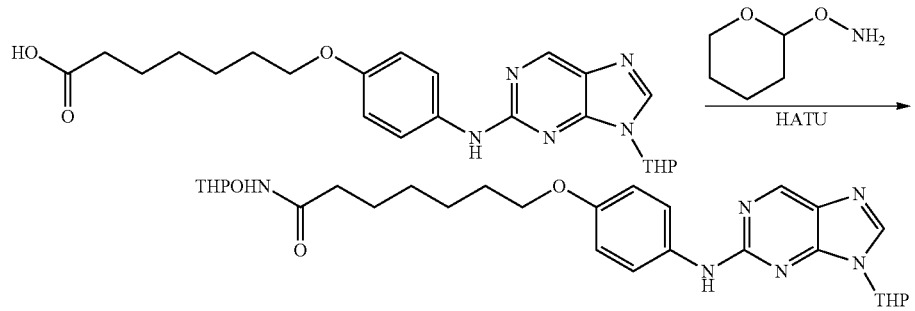

Synthesized according to the procedure described above in Example 17, Step 4. The crude product was purified by column chromatography to give 7-(4-((9-(tetrahydro-2H-pyran-2-yl)-9H-purin-2-yl)amino)phenoxy)-N-((tetrahydro-2H-pyran-2-yl)oxy)heptanamide (0.3 g).

Step 5: Preparation of 7-(4-((9H-purin-2-yl)amino)phenoxy)-N-hydroxyheptanamide

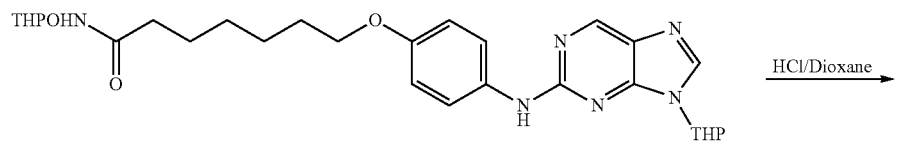

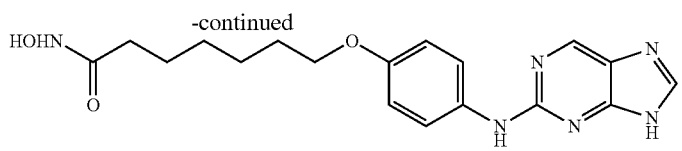

Synthesized according to the procedure described above in Example 17, Step 5 and purified by preparative HPLC to give 7-(4-((9H-purin-2-yl)amino)phenoxy)-N-hydroxyheptanamide (0.17 g). Mass Spec(m/z): 371.1 (M+1).

Example 25: Preparation of 7-(4-(((6-(cyclohexyl(methyl)amino)-9H-purin-2-yl)amino)phenoxy)-N-hydroxyheptanamide Step 1: Preparation of 2-chloro-N-cyclohexyl-N-methyl-9-(tetrahydro-2H-pyran-2-yl)-9H-purin-6-amine

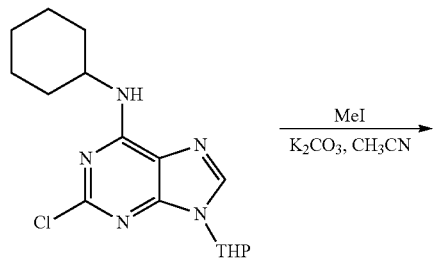

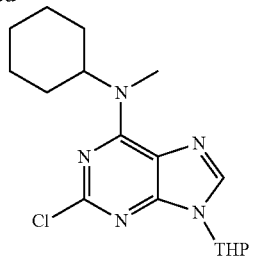

A mixture of 2-chloro-N-cyclohexyl-9-(tetrahydro-2H-pyran-2-yl)-9H-purin-6-amine (2.0 g, 6 mmol), $K_2CO_3$ (1.66 g, 12 mmol) and MeI (1.79 g, 12.6 mol) in acetonitrile (20 mL) was heated to 60° C. with stirring for 6 hrs. The resulting suspension was filtered and filtrate was concentrated to give 2-chloro-N-cyclohexyl-N-methyl-9-(tetrahydro-2H-pyran-2-yl)-9H-purin-6-amine (1.2 g) which was used without further purification.

Step 2: Preparation of methyl 7-(4-(((6-(cyclohexyl(methyl)amino)-9-(tetrahydro-2H-pyran-2-yl)-9H-purin-2-yl)amino)phenoxy)heptanoate

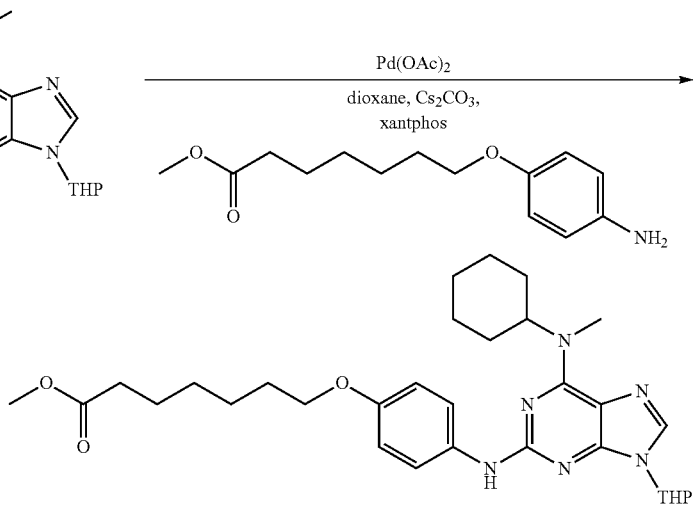

Synthesized according to the procedure described above in Example 17, Step 2 and purified by column chromatography to give methyl 7-(4-(((6-(cyclohexyl(methyl)amino)-9-(tetrahydro-2H-pyran-2-yl)-9H-purin-2-yl)amino)phenoxy)heptanoate (1.2 g, 74%).

Step 3: Preparation of 7-(4-((6-(cyclohexyl(methyl)amino)-9-(tetrahydro-2H-pyran-2-yl)-9H-purin-2-yl)amino)phenoxy)heptanoic acid

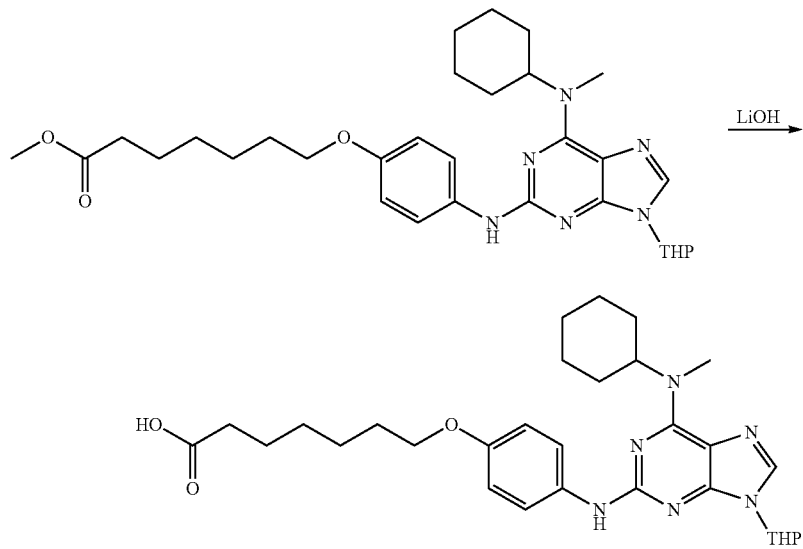

Synthesized according to the procedure described above in Example 17, Step 3 to give 7-(4-((6-(cyclohexyl(methyl)amino)-9-(tetrahydro-2H-pyran-2-yl)-9H-purin-2-yl)amino)phenoxy)heptanoic acid which was used without further purification.

Step 4

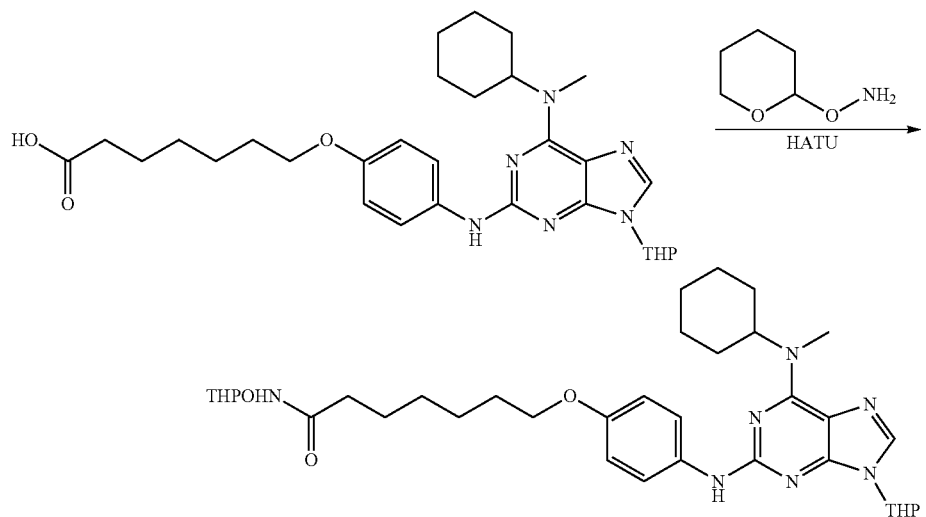

Synthesized according to the procedure described above in Example 17, Step 4 and purified by column chromatography to give 7-(4-((6-(cyclohexyl(methyl)amino)-9-(tetrahydro-2H-pyran-2-yl)-9H-purin-2-yl)amino)phenoxy)-N-((tetrahydro-2H-pyran-2-yl)oxy)heptanamide (0.35 g)

Step 5: Preparation of 7-(4-((6-(cyclohexyl(methyl)amino)-9H-purin-2-yl)amino)phenoxy)-N-hydroxyheptanamide

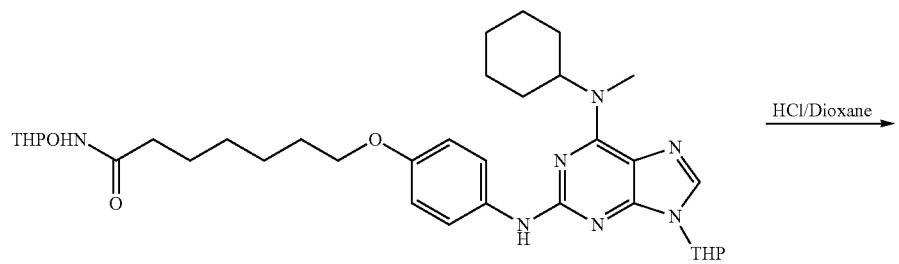

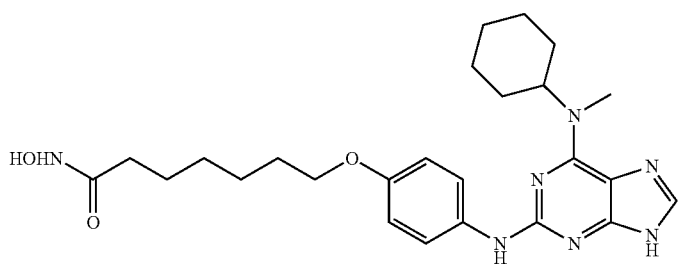

Synthesized according to the procedure described above in Example 17, Step 5 and purified by preparative HPLC to give 7-(4-((6-(cyclohexyl(methyl)amino)-9H-purin-2-yl)amino)phenoxy)-N-hydroxyheptanamide (33 mg). Mass Spec(m/z): (M+1).

Example 26: Preparation of N-hydroxy-7-(4-((6-((1-methylpiperidin-4-yl)amino)-9H-purin-2-yl)amino)phenoxy)heptanamide Step 1: Preparation of 2-chloro-N-(1-methylpiperidin-4-yl)-9-(tetrahydro-2H-pyran-2-yl)-9H-purin-6-amine

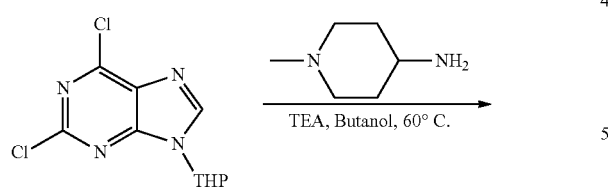

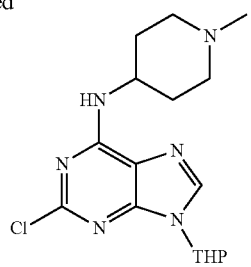

A mixture of 2,6-dichloro-9-(tetrahydro-2H-pyran-2-yl)-9H-purine (1.0 g, 3.7 mol), 1-Methyl-piperidin-4-ylamine (0.42 g, 3.7 mmol) in butanol (10 mL) and TEA (0.75 g, mmol) was heated to 40° C. with stirring for 3 hrs. The mixture was cooled and poured into water, extracted with EA and concentrated to give 2-chloro-N-(1-methylpiperidin-4-yl)-9-(tetrahydro-2H-pyran-2-yl)-9H-purin-6-amine (0.89 g) which was used without further purification.

Step 2: Preparation of methyl 7-(4-((6-((1-methylpiperidin-4-yl)amino)-9-(tetrahydro-2H-pyran-2-yl)-9H-purin-2-yl)amino)phenoxy)heptanoate

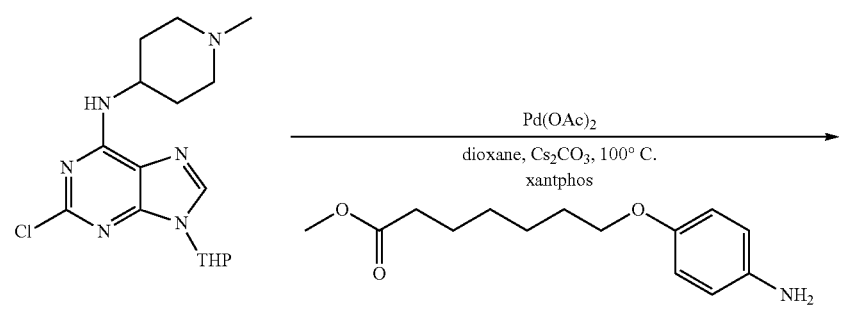

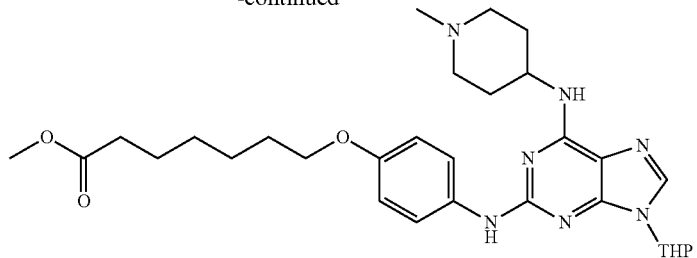

Synthesized according to the procedure described above in Example 21, Step 1 and purified by column chromatography to give methyl 7-(4-((6-((1-methylpiperidin-4-yl)amino)-9-(tetrahydro-2H-pyran-2-yl)-9H-purin-2-yl)amino)phenoxy)heptanoate (0.37 g) as a brown solid.

Step 3: Preparation of 7-(4-((6-((1-methylpiperidin-4-yl)amino)-9-(tetrahydro-2H-pyran-2-yl)-9H-purin-2-yl)amino)phenoxy)heptanoic acid

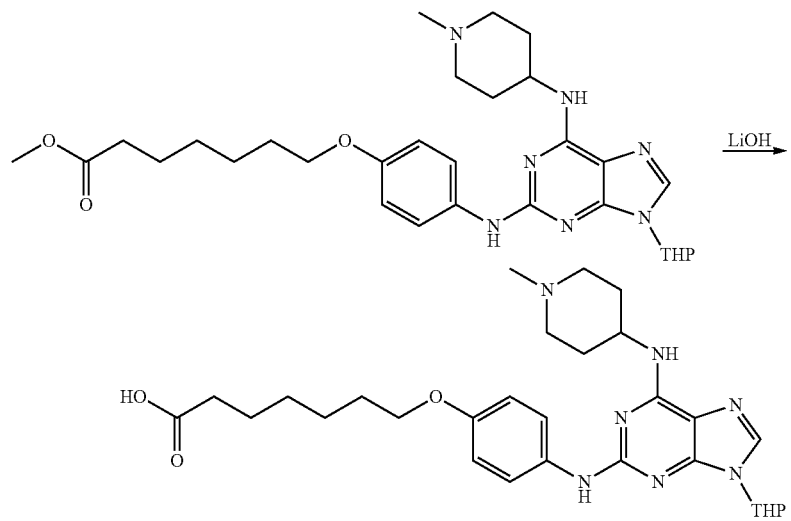

Synthesized according to the procedure described above in Example 18, Step 5 to give 7-(4-((6-((1-methylpiperidin-4-yl)amino)-9-(tetrahydro-2H-pyran-2-yl)-9H-purin-2-yl)amino)phenoxy)heptanoic acid (0.58 g, crude) which was used without further purification.

Step 4: Preparation of 7-(4-((6-((1-methylpiperidin-4-yl)amino)-9-(tetrahydro-2H-pyran-2-yl)-9H-purin-2-yl)amino)phenoxy)-N-((tetrahydro-2H-pyran-2-yl)oxy)heptanamide

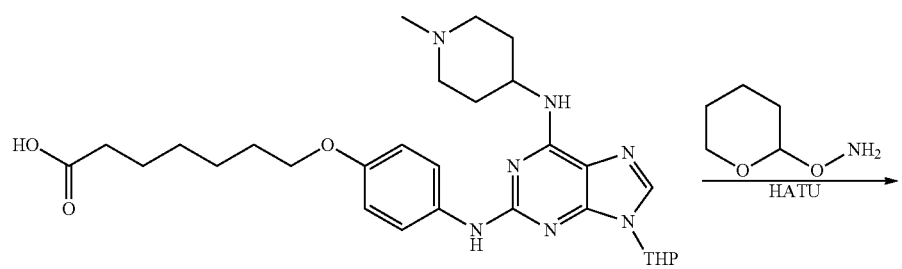

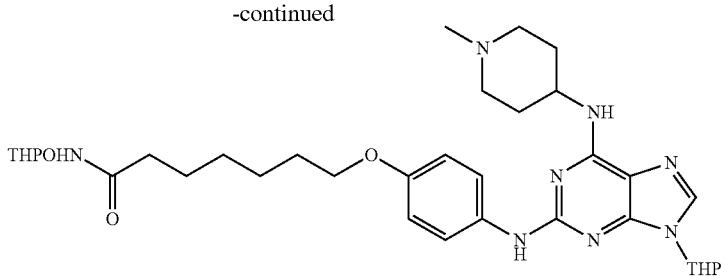

Synthesized according to the procedure described above in Example 18, Step 6 and purified by column chromatography to give 7-(4-((6-((1-methylpiperidin-4-yl)amino)-9-(tetrahydro-2H-pyran-2-yl)-9H-purin-2-yl)amino)phenoxy)-N-((tetrahydro-2H-pyran-2-yl)oxy)heptanamide (0.38 g).

Step 5: Preparation of N-hydroxy-7-(4-((6-((1-methylpiperidin-4-yl)amino)-9H-purin-2-yl)amino)phenoxy)heptanamide

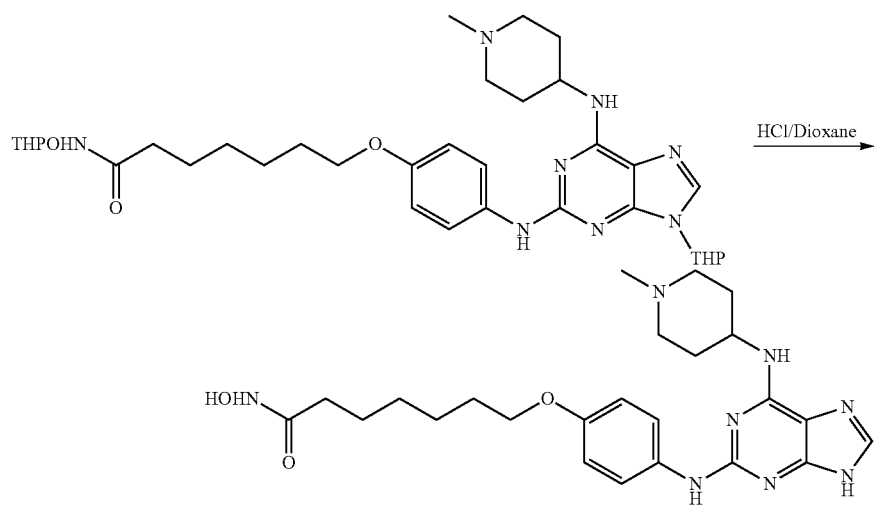

Synthesized according to the procedure described above in Example 18, Step 7 and purified by preparative HPLC to give N-hydroxy-7-(4-((6-((1-methylpiperidin-4-yl)amino)-9H-purin-2-yl)amino)phenoxy)heptanamide (27 mg) as a solid. Mass Spec(m/z): 482.2 (M+1)

Example 27: Preparation of N-hydroxy-7-(4-((6-phenyl-9H-purin-2-yl)amino)phenoxy)heptanamide Step 1: Preparation of 2-chloro-6-phenyl-9-(tetrahydro-2H-pyran-2-yl)-9H-purine

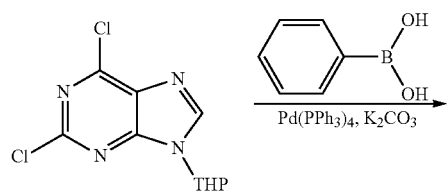

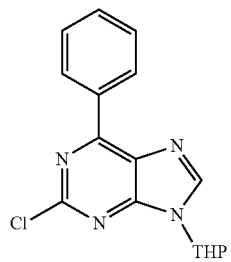

A mixture of 2,6-dichloro-9-(tetrahydro-2H-pyran-2-yl)-9H-purine (2.73 g, 10 mmol), Phenylboronic acid (1.22 g, 10 mmol), $K_2CO_3$ (4.14 g, 30 mmol) and $Pd(PPh)_4$ (273 mg) in toluene (50 mL) was degassed using argon for 10 min. The reaction flask was put into a preheated oil-bath at 100° C. and stirred overnight. The mixture was cooled to r.t., water was added and the resulting mixture was extracted with EtOAc. The combined extracts were washed with brine, dried, concentrated and purified by column chromatography to give 2-chloro-6-phenyl-9-(tetrahydro-2H-pyran-2-yl)-9H-purine as a brown solid (2.0 g, 64%).

Step 2: Preparation of methyl 7-(4-((6-phenyl-9-(tetrahydro-2H-pyran-2-yl)-9H-purin-2-yl)amino)phenoxy)heptanoate

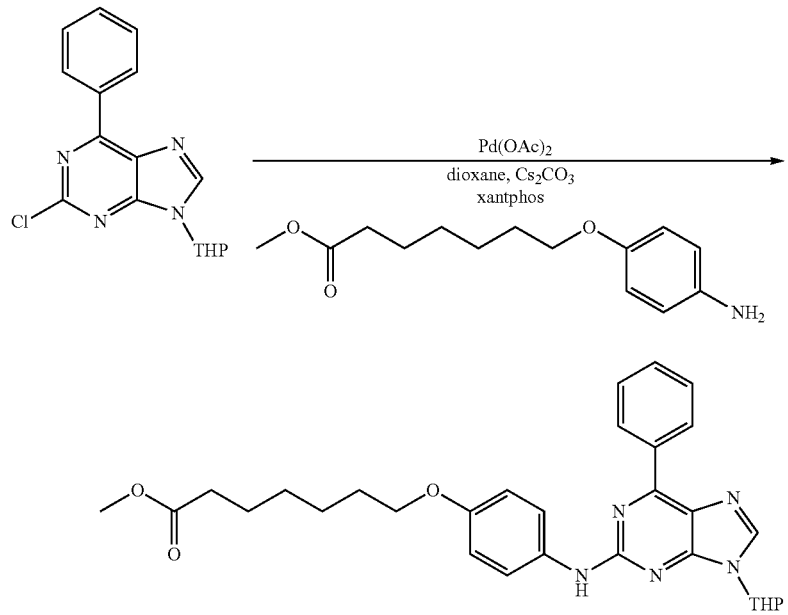

30

Synthesized according to the procedure described above in Example 17, Step 2 and purified by column chromatography to give 7-(4-((6-phenyl-9-(tetrahydro-2H-pyran-2-yl)-9H-purin-2-yl)amino)phenoxy)heptanoate (1.5 g).

Step 3: Preparation of 7-(4-((6-phenyl-9-(tetrahydro-2H-pyran-2-yl)-9H-purin-2-yl)amino)phenoxy)heptanoic acid

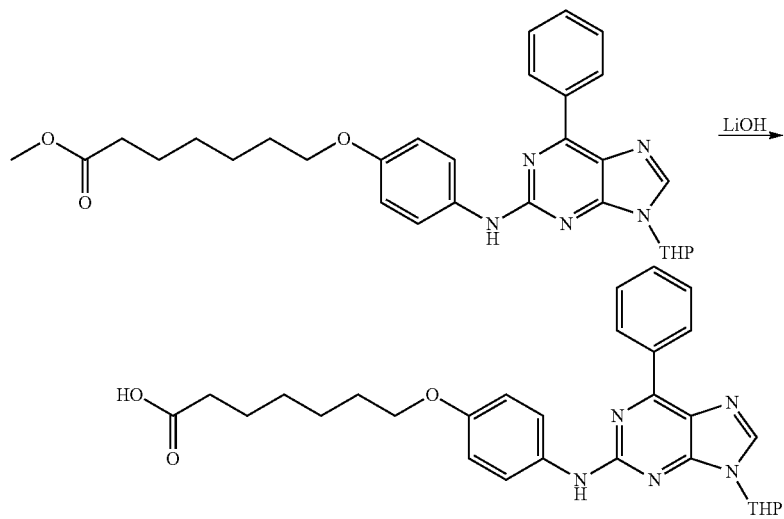

Synthesized according to the procedure described above in Example 17, Step 3 to give 7-(4-((6-phenyl-9-(tetrahydro-2H-pyran-2-yl)-9H-purin-2-yl)amino)phenoxy)heptanoic acid (0.57 g) which was used without further purification.

Step 4: Preparation of 7-(4-(((6-phenyl-9-(tetrahydro-2H-pyran-2-yl)-9H-purin-2-yl)amino)phenoxy)-N-((tetrahydro-2H-pyran-2-yl)oxy)heptanamide

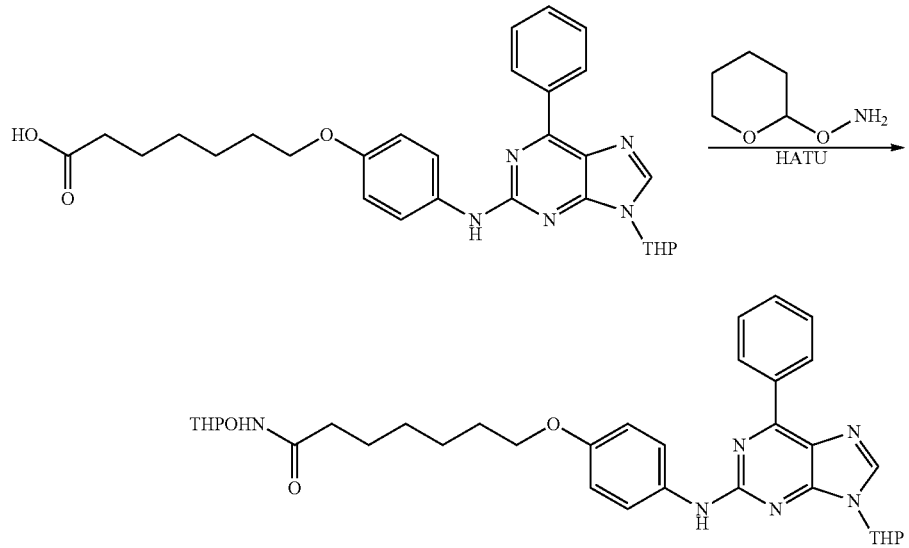

Synthesized according to the procedure described above in Example 17, Step 4 which was purified by column chromatography to give 7-(4-(((6-phenyl-9-(tetrahydro-2H-pyran-2-yl)-9H-purin-2-yl)amino)phenoxy)-N-((tetrahydro-2H-pyran-2-yl)oxy)heptanamide (0.35 g).

Step 5: Preparation of N-hydroxy-7-(4-(((6-phenyl-9H-purin-2-yl)amino)phenoxy)heptanamide

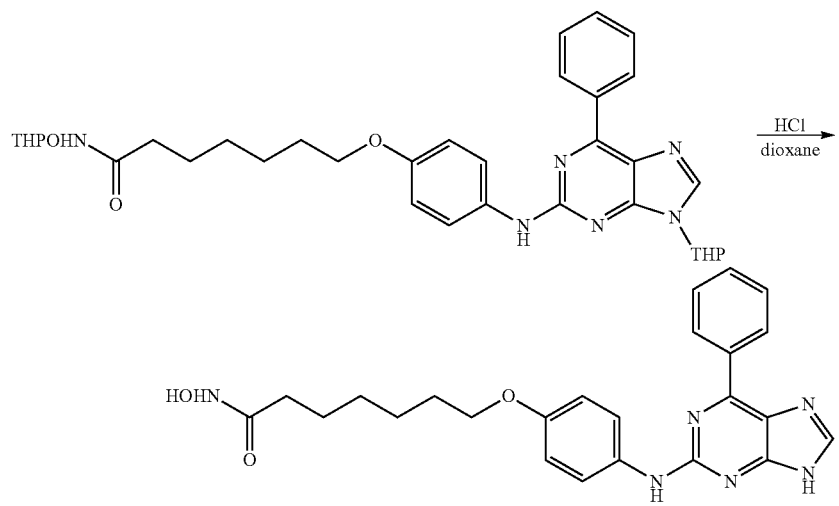

Synthesized according to the procedure described above in Example 17, Step 5 and purified by preparative HPLC to give N-hydroxy-7-(4-(((6-phenyl-9H-purin-2-yl)amino)phenoxy)heptanamide (83 mg). Mass Spec(m/z): 447.1 (M+1)

Example 28: Preparation of methyl 6-(4-aminobenzamido)hexanoate

Step 1: Preparation of methyl 6-(4-((tert-butoxycarbonyl)amino)benzamido)hexanoate

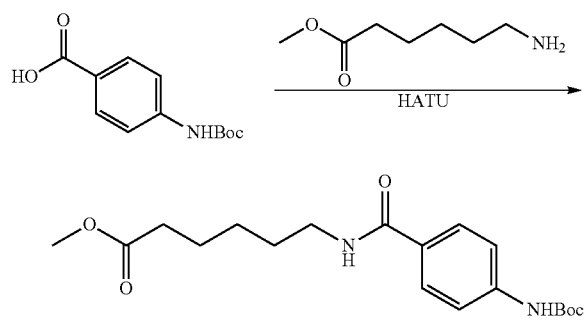

To a solution of 4-((tert-butoxycarbonyl)amino)benzoic acid (0.5 g, 2.1 mmol) and 6-Amino-hexanoic acid methyl ester.HCl (0.46 g, 2.5 mmol) in DMF (20 ml) was added TEA (0.848 g, 8.4 mmol) and HATU (1.2 g, 3.2 mol) at r.t. After stirring overnight, water was added and the mixture was extracted with EtOAc (2×50 ml). The combined organic layer was dried and concentrated, and the residue was purified by column chromatography to give methyl 6-(4-((tert-butoxycarbonyl)amino)benzamido)hexanoate (0.39 g, 54%) as a white solid.

Step 2: Preparation of methyl 6-(4-aminobenzamido)hexanoate

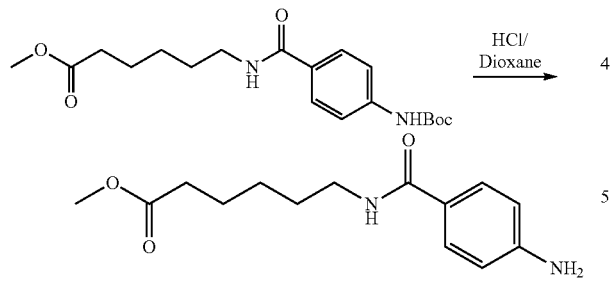

Methyl 6-(4-((tert-butoxycarbonyl)amino)benzamido)hexanoate (0.4 g, 1.1 mmol) was added to a solution of HCl/Dioxane (4M, 5 mL) and was stirred at r.t for 2 hrs. The mixture was then concentrated. To the residue, EtOAc and aq. NaHCO$_3$ solution were added. The layers were separation and the aqueous layer was extracted with EtOAc. The organic extract was dried and concentrated to give methyl 6-(4-aminobenzamido)hexanoate as brown solid (0.30 g) which was used without further purification.

Example 29: Preparation of 4-((6-(cyclohexylamino)-9H-purin-2-yl)amino)-N-(6-(hydroxyamino)-6-oxohexyl)benzamide

Step 1: Preparation of methyl 6-(4-((6-(cyclohexylamino)-9-(tetrahydro-2H-pyran-2-yl)-9H-purin-2-yl)amino)benzamido)hexanoate

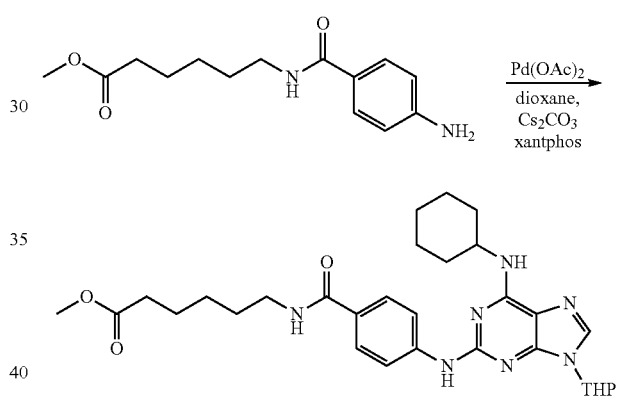

Synthesized according to the procedure described above in Example 17, Step 2 and purified by column chromatography to methyl 6-(4-((6-(cyclohexylamino)-9-(tetrahydro-2H-pyran-2-yl)-9H-purin-2-yl)amino)benzamido)hexanoate (0.49 g) as a brown solid.

Step 2: Preparation of 6-(4-((6-(cyclohexylamino)-9-(tetrahydro-2H-pyran-2-yl)-9H-purin-2-yl)amino)benzamido)hexanoic acid

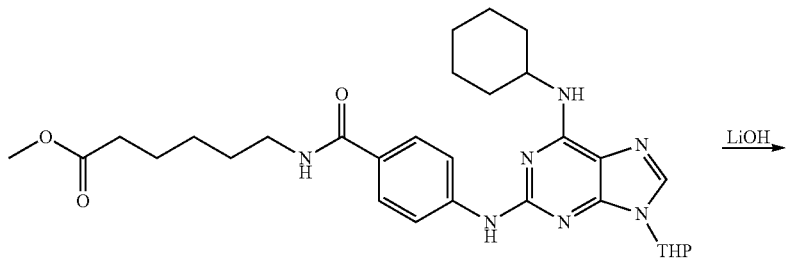

-continued

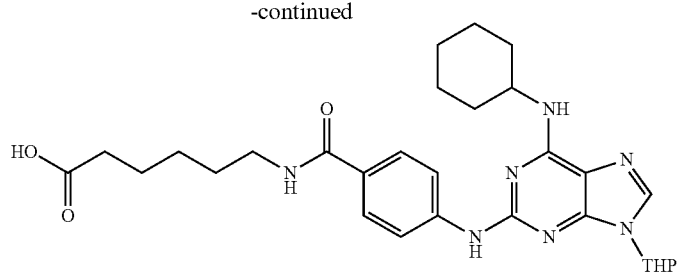

Synthesized according to the procedure described above in Example 17, Step 3 to give 6-(4-(((6-(cyclohexylamino)-9-(tetrahydro-2H-pyran-2-yl)-9H-purin-2-yl)amino)benzamido)hexanoic acid (0.38 g) which was used without further purification.

Step 3: Preparation of 4-((6-(cyclohexylamino)-9-(tetrahydro-2H-pyran-2-yl)-9H-purin-2-yl)amino)-N-(6-oxo-6-(((tetrahydro-2H-pyran-2-yl)oxy)amino)hexyl)benzamide

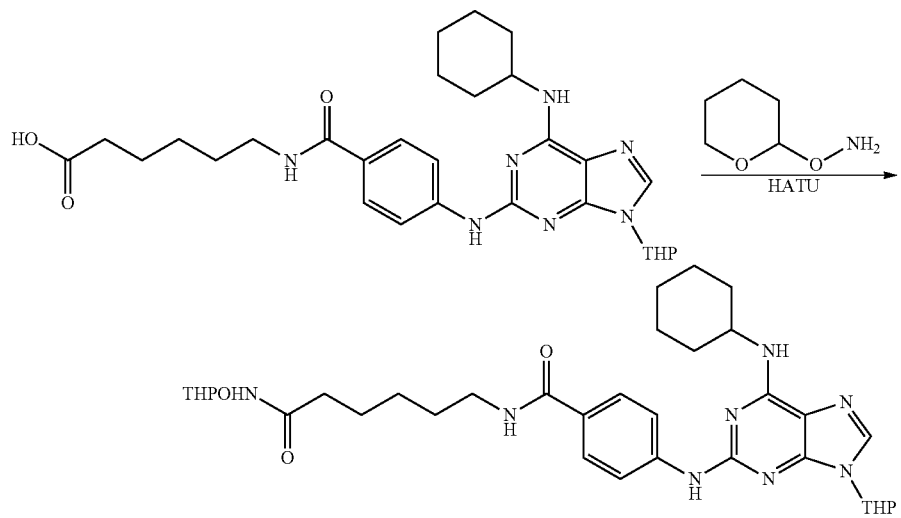

Synthesized according to the procedure described above in Example 17, Step 4 and purified by column chromatography to give 4-((6-(cyclohexylamino)-9-(tetrahydro-2H-pyran-2-yl)-9H-purin-2-yl)amino)-N-(6-oxo-6-(((tetrahydro-2H-pyran-2-yl)oxy)amino)hexyl)benzamide (0.25 g).

Step 4: Preparation of 4-((6-(cyclohexylamino)-9H-purin-2-yl)amino)-N-(6-(hydroxyamino)-6-oxohexyl)benzamide

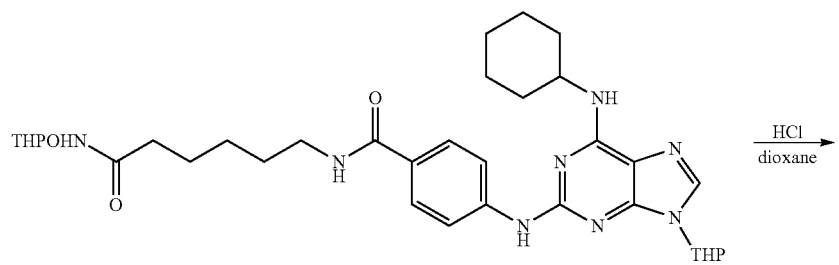

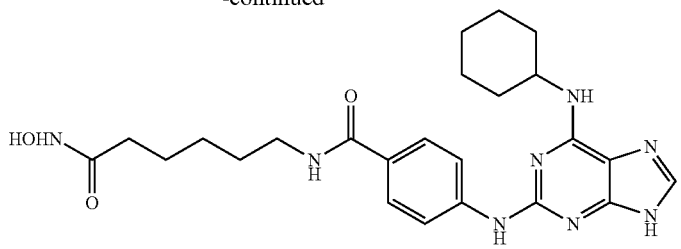

Synthesized according to the procedure described above in Example 17, Step 5 and purified using preparative HPLC to give 4-((6-(cyclohexylamino)-9H-purin-2-yl)amino)-N-(6-(hydroxyamino)-6-oxohexyl)benzamide (110 mg). Mass Spec(m/z): 481.2 (M+1)

Example 30: Preparation of methyl 5-(4-aminobenzamido)pentanoate

Step 1: Preparation of methyl 5-(4-((tert-butoxycarbonyl)amino)benzamido)pentanoate

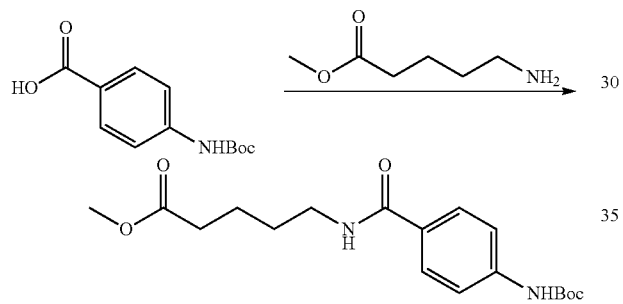

Synthesized according to the procedure described above in Example 28, Step 1 and purified by column chromatography to give methyl 5-(4-((tert-butoxycarbonyl)amino)benzamido)pentanoate as a white solid (0.35 g, 57%).

Step 2: Preparation of methyl 5-(4-aminobenzamido)pentanoate

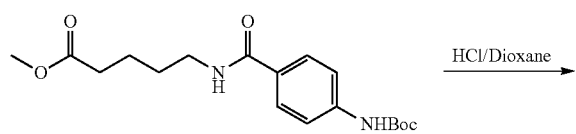

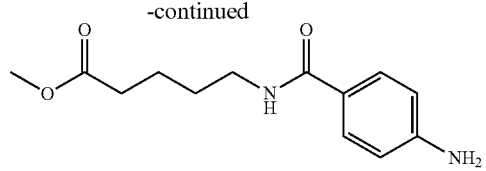

Synthesized according to the procedure described above in Example 28, Step 2 and used without further purification (0.23 g).

Example 31: Preparation of 4-((6-(cyclohexylamino)-9H-purin-2-yl)amino)-N-(5-(hydroxyamino)-5-oxopentyl)benzamide Step 1: Preparation of methyl 5-(4-((6-(cyclohexylamino)-9-(tetrahydro-2H-pyran-2-yl)-9H-purin-2-yl)amino)benzamido)pentanoate

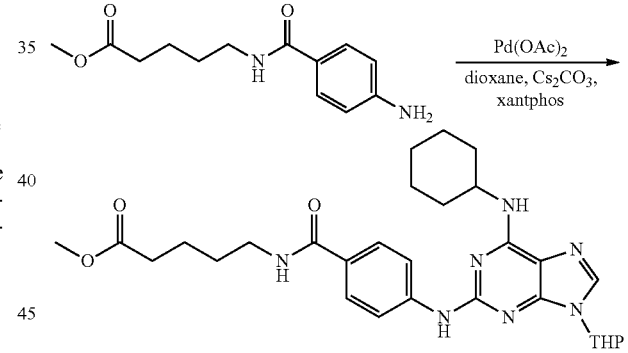

Synthesized according to the procedure described above in Example 17, Step 2 and purified by column chromatography to give methyl 5-(4-((6-(cyclohexylamino)-9-(tetrahydro-2H-pyran-2-yl)-9H-purin-2-yl)amino)benzamido)pentanoate as a brown solid (0.45 g, 82%).

Step 2: Preparation of 5-(4-((6-(cyclohexylamino)-9-(tetrahydro-2H-pyran-2-yl)-9H-purin-2-yl)amino)benzamido)pentanoic acid

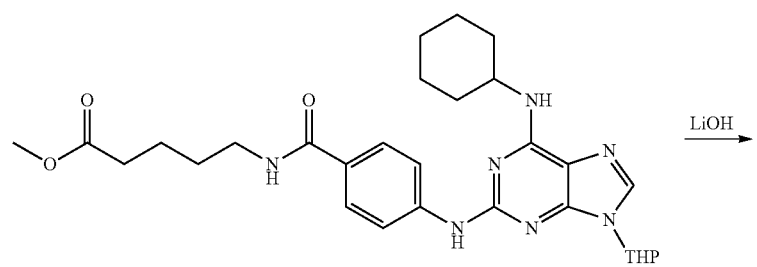

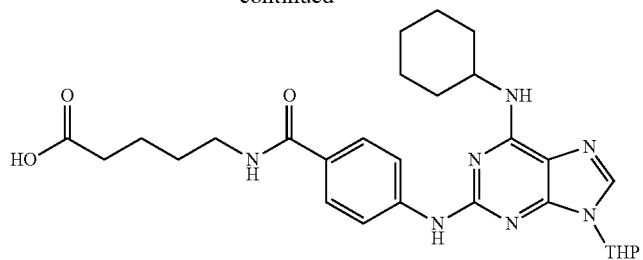

Synthesized according to the procedure described above in Example 17, Step 3 to give 5-(4-((6-(cyclohexylamino)-9-(tetrahydro-2H-pyran-2-yl)-9H-purin-2-yl)amino)benzamido)pentanoic acid (0.34 g) which was used without further purification.

Step 3

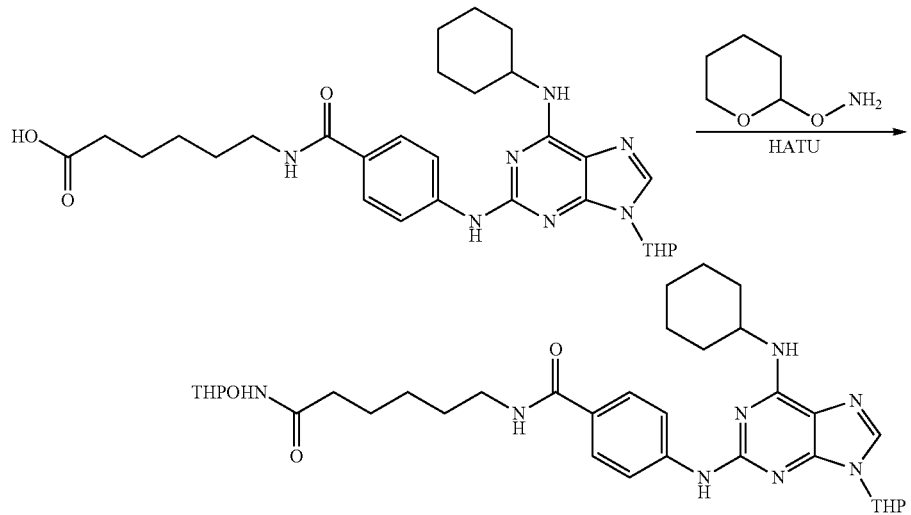

Synthesized according to the procedure described above in Example 17, Step 4 and purified by column chromatography to give 4-((6-(cyclohexylamino)-9-(tetrahydro-2H-pyran-2-yl)-9H-purin-2-yl)amino)-N-(6-oxo-6-(((tetrahydro-2H-pyran-2-yl)oxy)amino)hexyl)benzamide (0.25 g).

Step 4: Preparation of 4-((6-(cyclohexylamino)-9H-purin-2-yl)amino)-N-(5-(hydroxyamino)-5-oxopentyl)benzamide

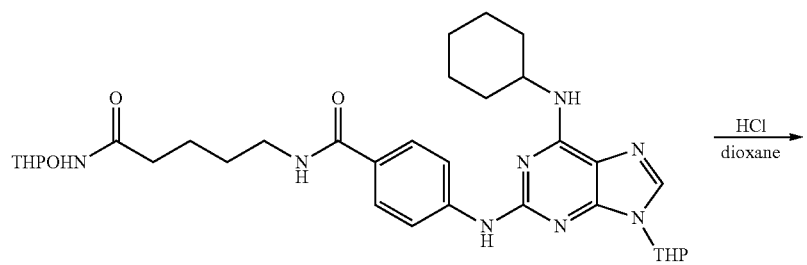

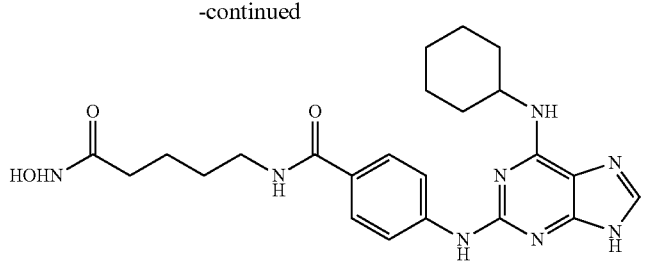

Synthesized according to the procedure described above in Example 17, Step 5 and purified using preparative HPLC to give 4-((6-(cyclohexylamino)-9H-purin-2-yl)amino)-N-(5-(hydroxyamino)-5-oxopentyl)benzamide (24 mg). Mass Spec(m/z): 467.2 (M+1)

Example 32: Preparation of 7-(4-((4-(cyclohexylamino)-1H-imidazo[4,5-c]pyridin-6-yl)amino)phenoxy)-N-hydroxyheptanamide Step 1: Preparation of 4,6-dichloro-1-(tetrahydro-2H-pyran-2-yl)-1H-imidazo[4,5-c]pyridine

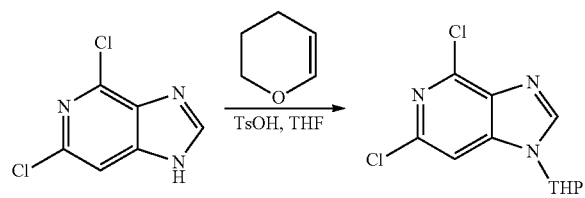

A mixture of 4,6-dichloro-1H-imidazo[4,5-c]pyridine (1.0 g, 5.3 mmol), TsOH (91 mg, 0.53 mmol) and DHP (134 mg, 15.9 mol) in THF (20 mL) was heated to reflux and stirred overnight. Then the mixture was concentrated and purified by column chromatography to give 4,6-dichloro-1-(tetrahydro-2H-pyran-2-yl)-1H-imidazo[4,5-c]pyridine as a gray solid (0.78 g, 55%).

Step 2: Preparation of 6-chloro-N-cyclohexyl-1-(tetrahydro-2H-pyran-2-yl)-1H-imidazo[4,5-c]pyridin-4-amine

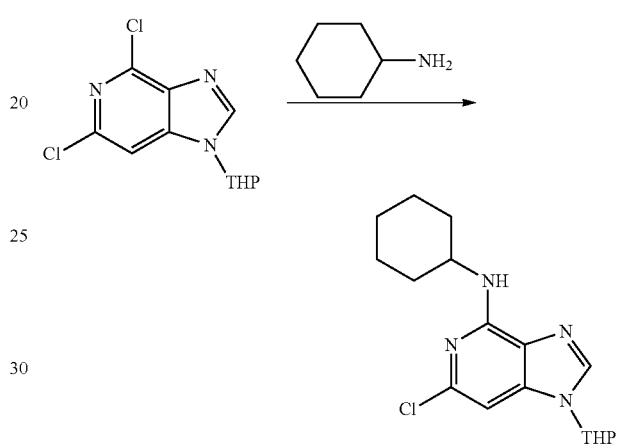

A mixture of 4,6-dichloro-1-(tetrahydro-2H-pyran-2-yl)-1H-imidazo[4,5-c]pyridine1 (1.0 g, 3.69 mol) and cyclohexylamine (5 mL) in butanol (10 mL) was heated to 100° C. and stirred overnight. The mixture was cooled, poured into water and extracted with EA. Purification by column chromatography gave 6-chloro-N-cyclohexyl-1-(tetrahydro-2H-pyran-2-yl)-1H-imidazo[4,5-c]pyridin-4-amine as an oil (0.8 g, 64.7%).

Step 3: Preparation of methyl 7-(4-((4-(cyclohexylamino)-1-(tetrahydro-2H-pyran-2-yl)-1H-imidazo[4,5-c]pyridin-6-yl)amino)phenoxy)heptanoate

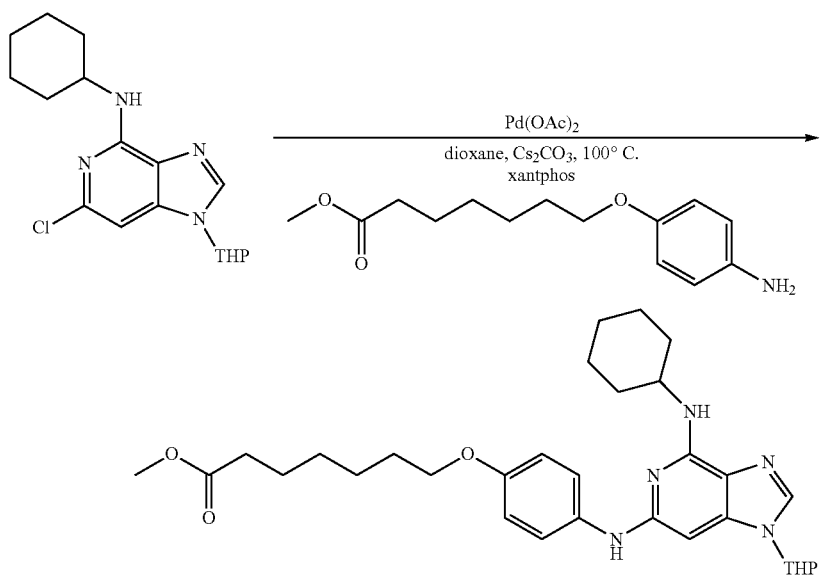

To a solution of 6-chloro-N-cyclohexyl-1-(tetrahydro-2H-pyran-2-yl)-1H-imidazo[4,5-c]pyridin-4-amine (0.6 g, 1.8 mmol) in dioxane (10 mL) was added methyl 7-(4-aminophenoxy)heptanoate (0.5 g, 1.98 mmol), xantphos (104 mg, 0.18 mmol), $Cs_2CO_3$ (880 mg, 2.7 mmol) and $Pd(OAc)_2$ (40 mg, 0.18 mol). The mixture was degassed using argon for 10 min. The reaction flask was emmersed into a preheated oil-bath at 80° C. and stirred overnight. The mixture was cooled to r.t, quenched with water, and extracted with DCM. The combined organic layers were washed with sat. aq. $NH_4Cl$ sol., dried, concentrated and purified by column chromatography to give methyl 7-(4-((4-(cyclohexylamino)-1-(tetrahydro-2H-pyran-2-yl)-1H-imidazo[4,5-c]pyridin-6-yl)amino)phenoxy)heptanoate as a brown solid (0.51 g, 50%).

Step 4: Preparation of 7-(4-((4-(cyclohexylamino)-1-(tetrahydro-2H-pyran-2-yl)-1H-imidazo[4,5-c]pyridin-6-yl)amino)phenoxy)heptanoic acid

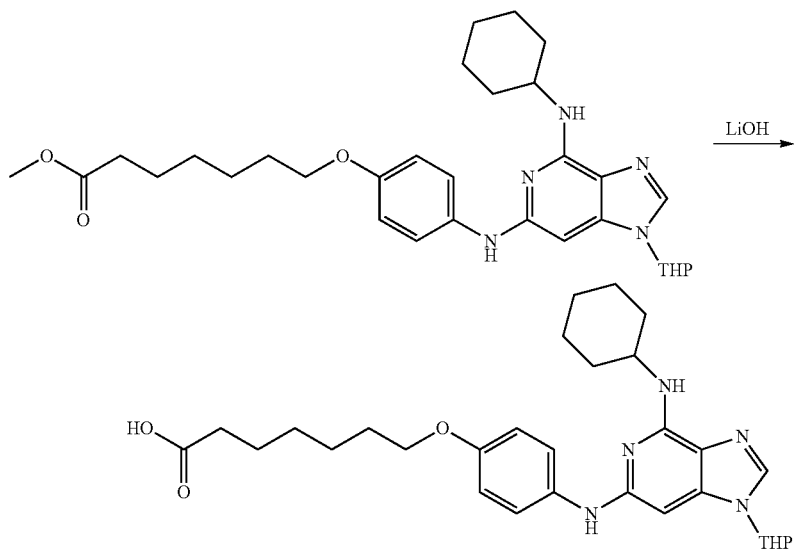

Synthesized according to the procedure described above in Example 18, Step 5 to give 7-(4-((4-(cyclohexylamino)-1-(tetrahydro-2H-pyran-2-yl)-1H-imidazo[4,5-c]pyridin-6-yl)amino)phenoxy)heptanoic acid which was used without further purification.

Step 5: Preparation of 7-(4-((4-(cyclohexylamino)-1-(tetrahydro-2H-pyran-2-yl)-1H-imidazo[4,5-c]pyridin-6-yl)amino)phenoxy)-N-((tetrahydro-2H-pyran-2-yl)oxy)heptanamide

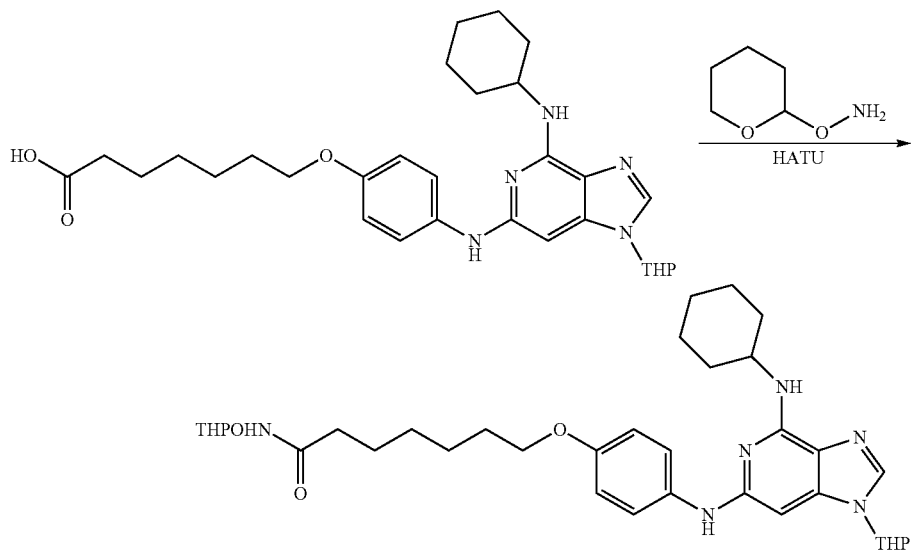

Synthesized according to the procedure described above in Example 18, Step 6 and purified by column chromatography to give 7-(4-((4-(cyclohexylamino)-1-(tetrahydro-2H-pyran-2-yl)-1H-imidazo[4,5-c]pyridin-6-yl)amino)phenoxy)-N-((tetrahydro-2H-pyran-2-yl)oxy)heptanamide (0.27 g)

Step 6: Preparation of 7-(4-((4-(cyclohexylamino)-1H-imidazo[4,5-c]pyridin-6-yl)amino)phenoxy)-N-hydroxyheptanamide

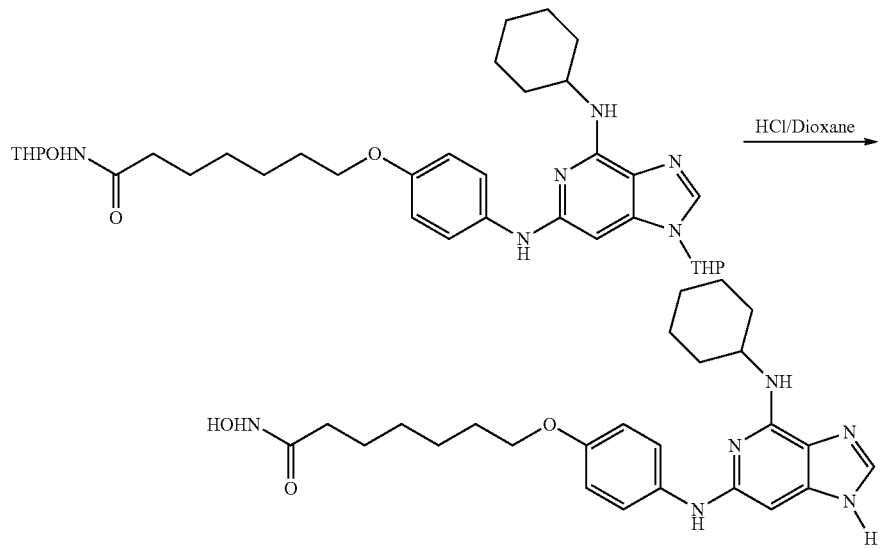

Synthesized according to the procedure described above in Example 18, Step 6 and purified by preparative HPLC to give 7-(4-((4-(cyclohexylamino)-1H-imidazo[4,5-c]pyridin-6-yl)amino)phenoxy)-N-hydroxyheptanamide (25 mg). Mass Spec(m/z): 467.2 (M+1)

Example 33: Preparation of 7-(4-((7-(cyclohexylamino)thiazolo[4,5-d]pyrimidin-5-yl)amino)phenoxy)-N-hydroxyheptanamide Step 1: Preparation of 5-chloro-N-cyclohexylthiazolo[4,5-d]pyrimidin-7-amine

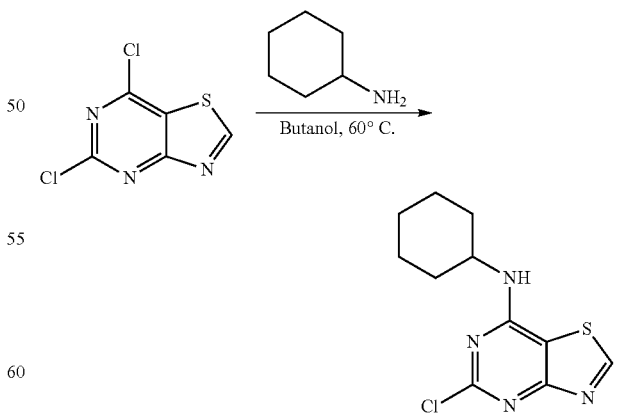

Synthesized according to the procedure described above in Example 1, Step 1 and purified by column chromatography to give 5-chloro-N-cyclohexylthiazolo[4,5-d]pyrimidin-7-amine as an oil (0.37 g 78%)

Step 2: Preparation of methyl 7-(4-((7-(cyclohexy-lamino)thiazolo[4,5-d]pyrimidin-5-yl)amino)phe-noxy)heptanoate

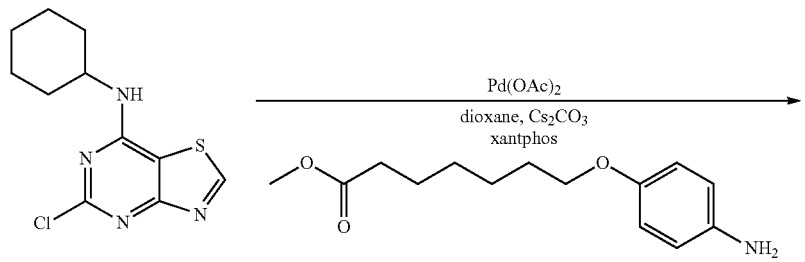

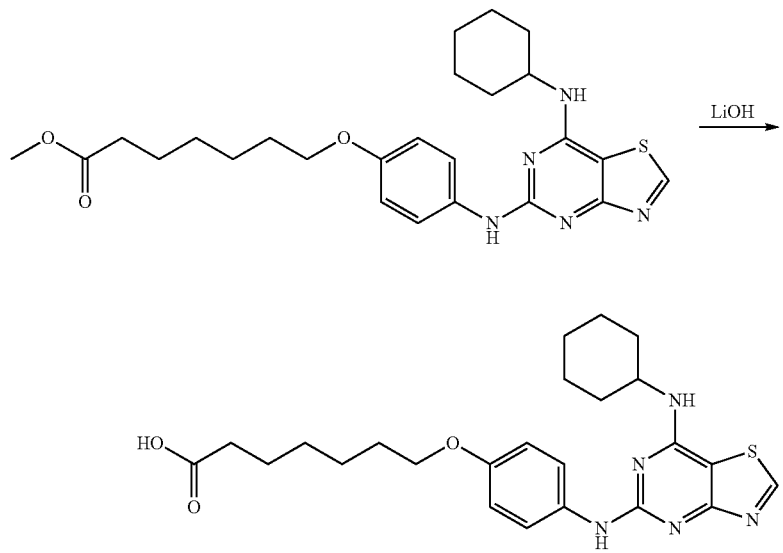

Synthesized according to the procedure described above in Example 17, step 2 and purified by column chromatography (0.49 g, 59%).

Step 3: Preparation of 7-(4-((7-(cyclohexylamino)thiazolo[4,5-d]pyrimidin-5-yl)amino)phenoxy)heptanoic acid Synthesized according to the procedure described above in Example 17, step 3 to give 7-(4-((7-(cyclohexylamino)thiazolo[4,5-d]pyrimidin-5-yl)amino)phenoxy)heptanoic acid which was used without further purification.

Step 4: Preparation of 7-(4-((7-(cyclohexylamino)thiazolo[4,5-d]pyrimidin-5-yl)amino)phenoxy)-N-((tetrahydro-2H-pyran-2-yl)oxy)heptanamide

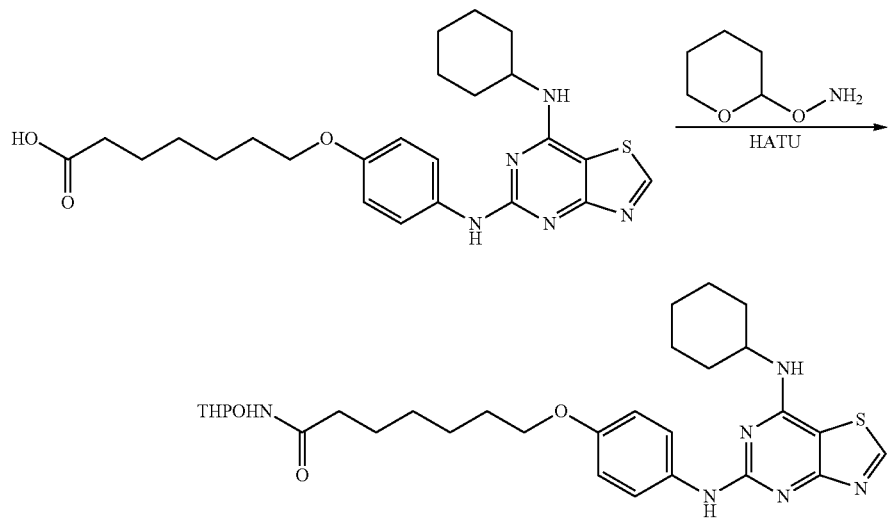

Synthesized according to the procedure described above in Example 17, step 4 and to give 7-(4-((7-(cyclohexylamino)thiazolo[4,5-d]pyrimidin-5-yl)amino)phenoxy)-N-((tetrahydro-2H-pyran-2-yl)oxy)heptanamide (0.31 g)

Step 5: Preparation of 7-(4-((7-(cyclohexylamino)thiazolo[4,5-d]pyrimidin-5-yl)amino)phenoxy)-N-hydroxyheptanamide

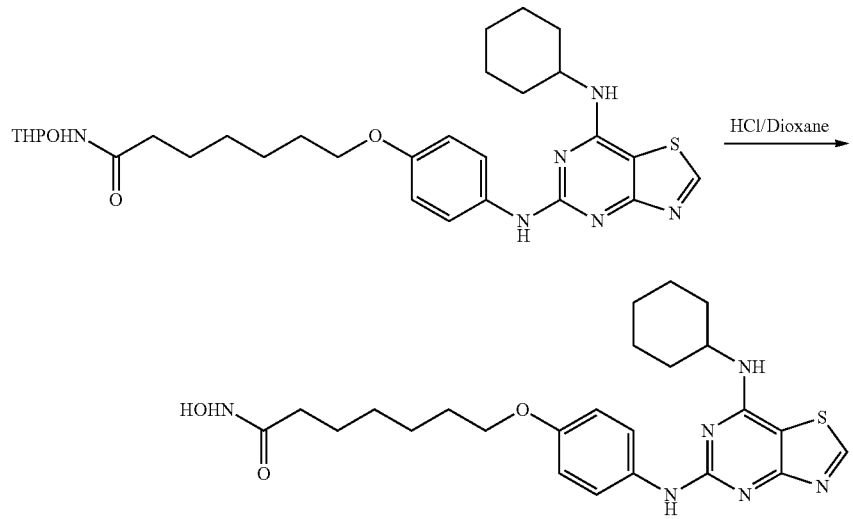

Synthesized according to the procedure described above in Example 17, step 5 and purified by preparative HPLC to give 7-(4-((7-(cyclohexylamino)thiazolo[4,5-d]pyrimidin-5-yl)amino)phenoxy)-N-hydroxyheptanamide (85 mg). Mass Spec(m/z): 485.2 (M+1)

Example 34: Preparation of 7-(4-((4-(cyclohexylamino)-7H-pyrrolo[2,3-d]pyrimidin-2-yl)amino)phenoxy)-N-hydroxyheptanamide

Step 1: Preparation of 2-chloro-N-cyclohexyl-7-tosyl-7H-pyrrolo[2,3-d]pyrimidin-4-amine

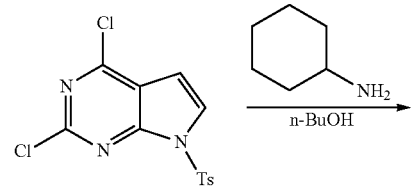

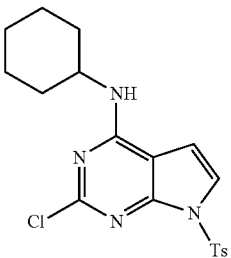

Synthesized according to the procedure described above in Example 1, step 1 and purified by column chromatography to give 2-chloro-N-cyclohexyl-7-tosyl-7H-pyrrolo[2,3-d]pyrimidin-4-amine (0.51 g)

Step 2: Preparation of methyl 7-(4-((4-(cyclohexylamino)-7-tosyl-7H-pyrrolo[2,3-d]pyrimidin-2-yl)amino)phenoxy)heptanoate

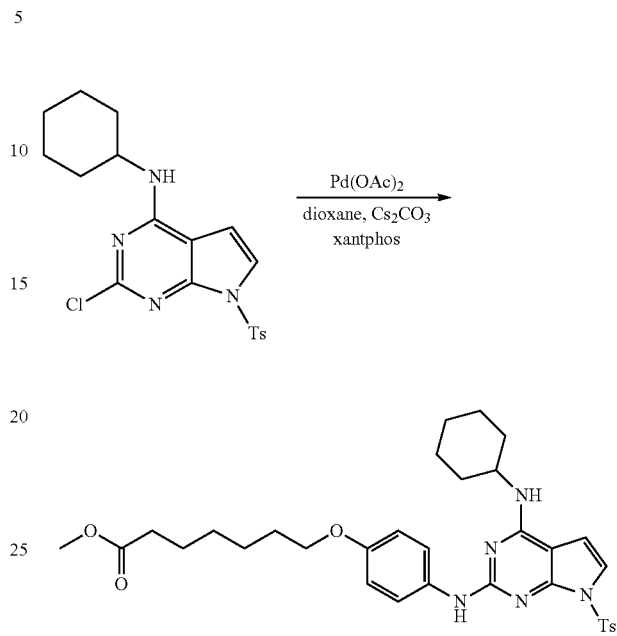

Synthesized according to the procedure described above in Example 17, step 2 and purified by column chromatography to give 7-(4-((4-(cyclohexylamino)-7-tosyl-7H-pyrrolo[2,3-d]pyrimidin-2-yl)amino)phenoxy)heptanoate as a brown solid (0.58 g, 70%)

Step 3: Preparation of 7-(4-((4-(cyclohexylamino)-7-tosyl-7H-pyrrolo[2,3-d]pyrimidin-2-yl)amino)phenoxy)heptanoic acid

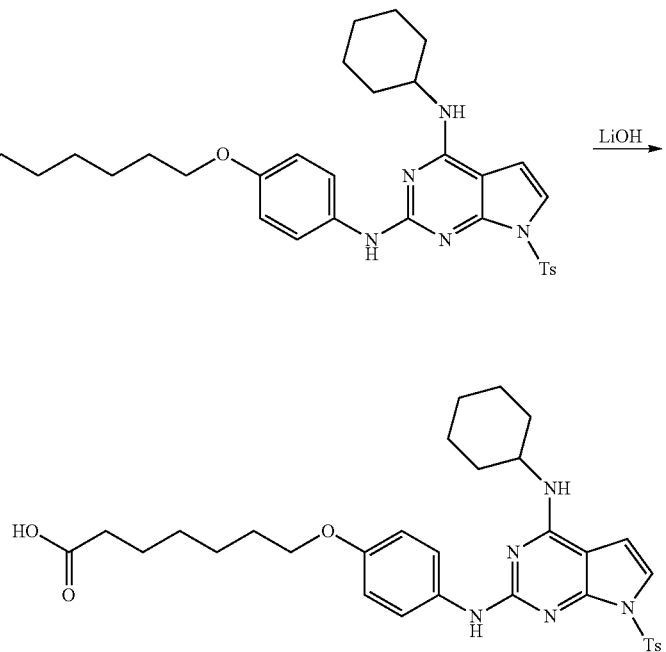

Synthesized according to the procedure described above in Example 17, step 3 and used without further purification.

Step 4: Preparation of 7-(4-((4-(cyclohexylamino)-7H-pyrrolo[2,3-d]pyrimidin-2-yl)amino)phenoxy) heptanoic acid

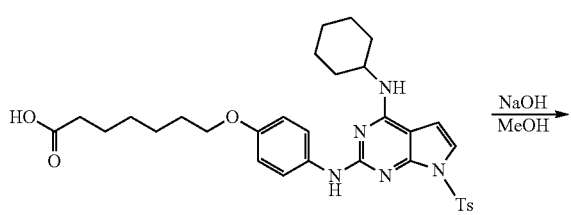

A mixture of 7-(4-((4-(cyclohexylamino)-7-tosyl-7H-pyrrolo[2,3-d]pyrimidin-2-yl)amino)phenoxy)heptanoic acid (0.70 g,) and NaOH (80 mg) in MeOH (20 mL) was heated to reflux with stirring and stirred for 2 hrs. Then the mixture was cooled, concentrated, dissolved in DCM/MeOH (10/1, 20 mL) and washed with dilute HCl solution. The organic layer was dried and concentrated to give 7-(4-((4-(cyclohexylamino)-7H-pyrrolo[2,3-d]pyrimidin-2-yl)amino)phenoxy)heptanoic acid which was used without further purification Step 5: Preparation of 7-(4-((4-(cyclohexylamino)-7H-pyrrolo[2,3-d]pyrimidin-2-yl)amino)phenoxy)-N-((tetrahydro-2H-pyran-2-yl)oxy)heptanamide

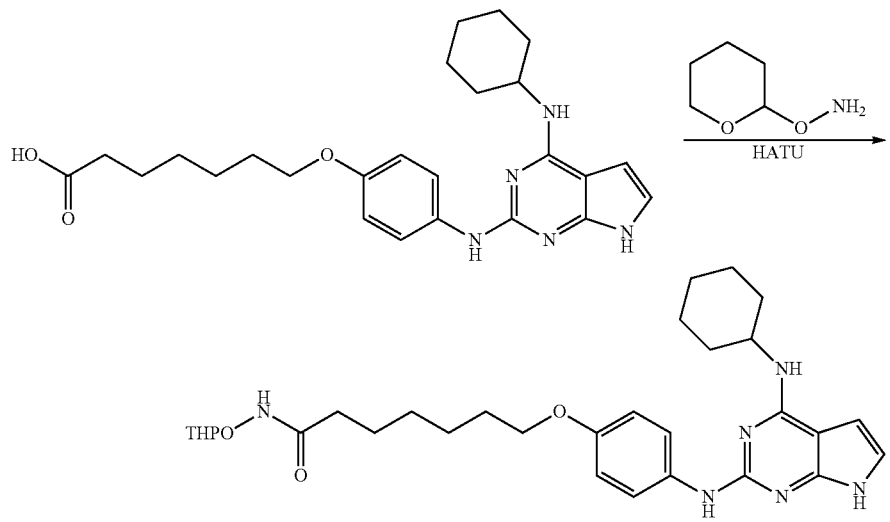

Synthesized according to the procedure described above in Example 17, step 4 and purified by column chromatography to give 7-(4-((4-(cyclohexylamino)-7H-pyrrolo[2,3-d]pyrimidin-2-yl)amino)phenoxy)-N-((tetrahydro-2H-pyran-2-yl)oxy)heptanamide Step 6: Preparation of 7-(4-((4-(cyclohexylamino)-7H-pyrrolo[2,3-d]pyrimidin-2-yl)amino)phenoxy)-N-hydroxyheptanamide

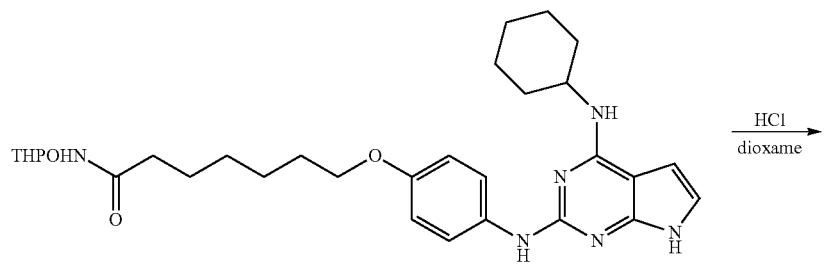

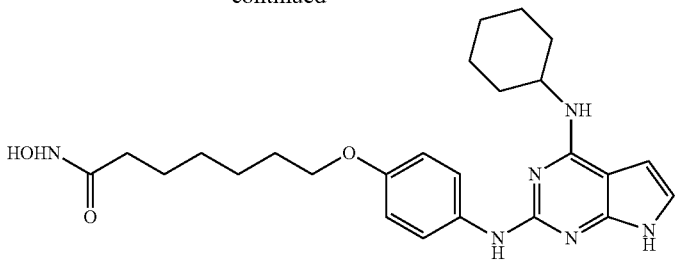

Synthesized according to the procedure described above in Example 17, step 5 and purified by preparative HPLC to give 7-(4-((4-(cyclohexylamino)-7H-pyrrolo[2,3-d]pyrimidin-2-yl)amino)phenoxy)-N-hydroxyheptanamide. Mass Spec(m/z): 467.2 (M+1)

Example 35: Preparation of 7-(4-((6-benzyl-9H-purin-2-yl)amino)phenoxy)-N-hydroxyheptanamide Step 1: Preparation of 2,6-dichloro-9-(4-methoxybenzyl)-9H-purine

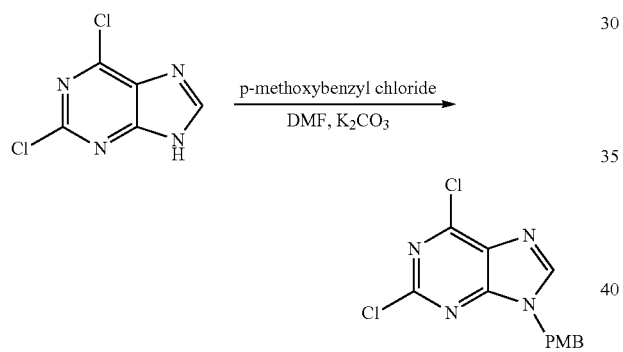

2,6-dichloro-9H-purine (5.0 g, 26 mmol), p-methoxybenzyl chloride (4.42 g, 28.6 mmol) and K$_2$CO$_3$ (7.2 g, 52 mmol) in DMF (50 mL) was heated to 80° C. and stirred for 4 hrs. The mixture was cooled, poured into water (100 ml) and extracted with EtOAc (3×50 ml). The combined extracts were dried, filtered, concentrated and the residue was purified by column chromatography to 2,6-dichloro-9-(4-methoxybenzyl)-9H-purine as a white solid (2 g, 21%).

Step 2: Preparation of 6-benzyl-2-chloro-9-(4-methoxybenzyl)-9H-purine

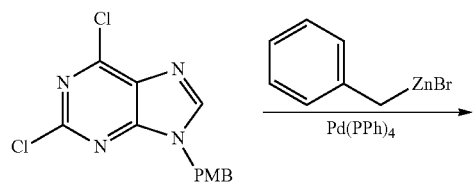

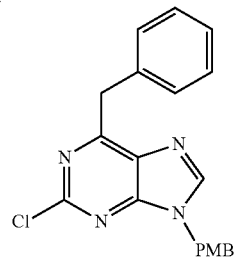

A mixture of 2,6-dichloro-9-(4-methoxybenzyl)-9H-purine (2.0 g, 6.5 mmol), Benzylzinc Bromide (9.8 mL, 1 M in THF), and Pd(PPh)$_4$ (796 mg) in THF (10 mL) was degassed using argon for 10 min. The reaction flask was put into a preheated oil-bath at 60° C. and stirred for 3 hrs. The mixture was cooled to r.t, poured into water, and extracted with EtOAc (2×50 ml). The combined organic layer was washed with brine, dried, and concentrated and purified by column chromatography to give 6-benzyl-2-chloro-9-(4-methoxybenzyl)-9H-purine as a red oil (1.4 g, 58%).

Step 3: Preparation of methyl 7-(4-((6-benzyl-9-(4-methoxybenzyl)-9H-purin-2-yl)amino)phenoxy) heptanoate

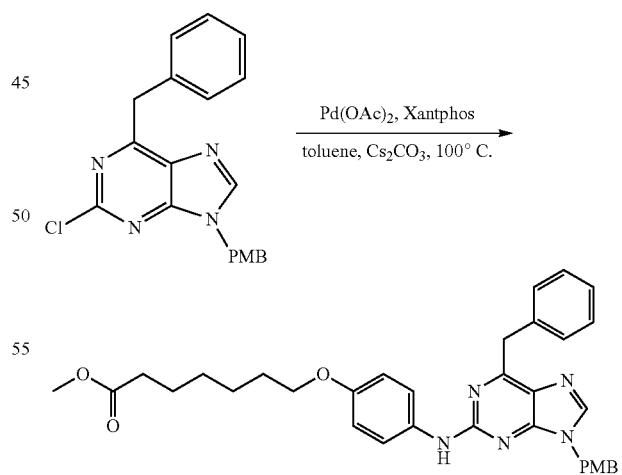

To a solution of 6-benzyl-2-chloro-9-(4-methoxybenzyl)-9H-purine (1.4 g, 3.85 mmol) in dioxane (10 mL) was added methyl 7-(4-aminophenoxy)heptanoate (analogous to Example 2; step 1 alternative procedure) (1.06 g, 4.24 mmol), xantphos (222 mg, 0.385 mmol), Cs$_2$CO$_3$ (1.88 g, 5.78 mmol) and Pd(OAc)$_2$ (86 g, 0.385 mol). The mixture was degassed using argon for 10 min. The reaction flask was put into a preheated oil-bath at 100° C. and stirred overnight. The mixture was cooled to r.t, poured into 50 ml of water and extracted with DCM (2×50 ml). The combined extracts were washed with sat. aq. NH₄Cl., dried and concentrated. Purification with column chromatography gave methyl 7-(4-((6-benzyl-9-(4-methoxybenzyl)-9H-purin-2-yl)amino)phenoxy)heptanoate as a brown solid (0.8 g, 36%).

Step 4: Preparation of methyl 7-(4-((6-benzyl-9H-purin-2-yl)amino)phenoxy)heptanoate

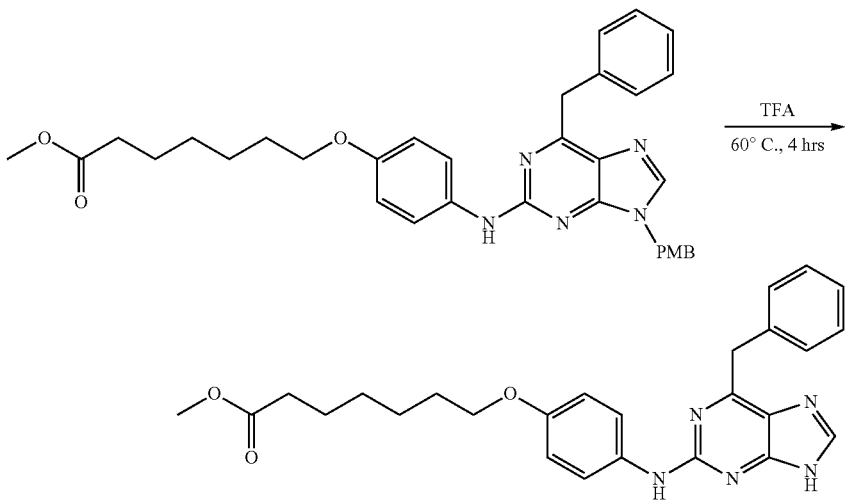

A solution of methyl 7-(4-((6-benzyl-9-(4-methoxybenzyl)-9H-purin-2-yl)amino)phenoxy)heptanoate (0.5 g) in TFA (10 mL) was heated to 60° C. for 4 hrs The solution was cooled to r.t. and concentrated to give methyl 7-(4-((6-benzyl-9H-purin-2-yl)amino)phenoxy)heptanoate (0.5 g, Crude).

Step 5: Preparation of 7-(4-((6-benzyl-9H-purin-2-yl)amino)phenoxy)heptanoic acid

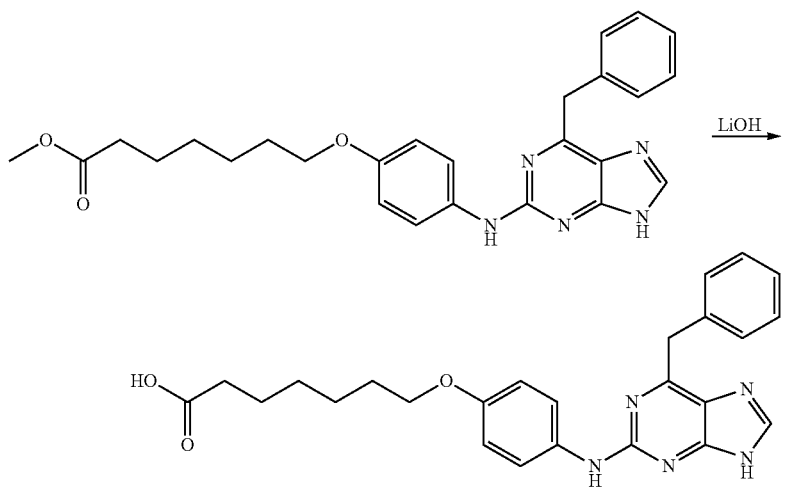

To the solution of methyl 7-(4-((6-benzyl-9-(4-methoxybenzyl)-9H-purin-2-yl)amino)phenoxy)heptanoate (0.5 g, Crude) in THF (10 mL) and water (2 mL) was added lithium hydroxide monohydrate (200 mg, 4.76 mmol) at r.t. After stirring for 4 hrs., EtOAc (20 ml) was added and the solution was washed once with dilute HCl solution. The organic layer was dried and concentrated to give crude product 7-(4-((6-benzyl-9H-purin-2-yl)amino)phenoxy)heptanoic acid (0.5 g). The crude product was used without further purification.

Step 6: Preparation of 7-(4-((6-benzyl-9H-purin-2-yl)amino)phenoxy)-N-((tetrahydro-2H-pyran-2-yl)oxy)heptanamide

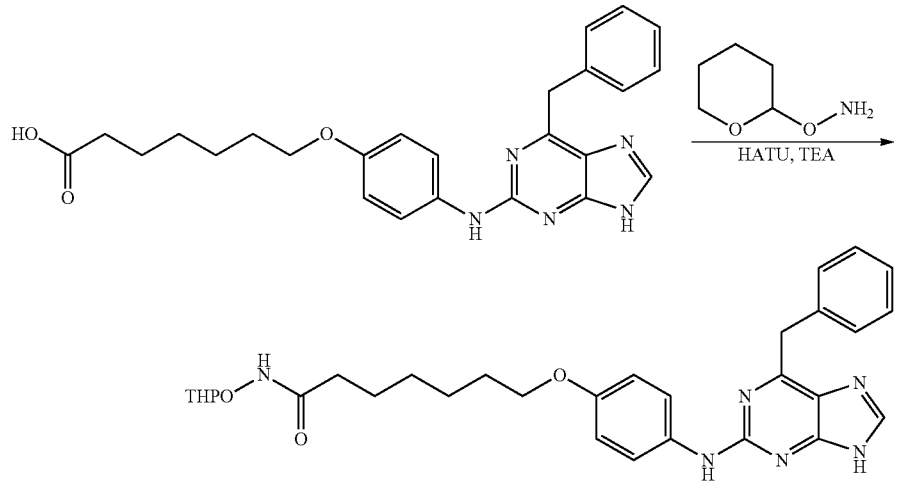

To the solution of 7-(4-((6-benzyl-9H-purin-2-yl)amino)phenoxy)heptanoic acid (152 mg, 1.3 mmol) in DMF was added TEA (0.33 g, 3.2 mmol) and HATU (0.62 g, 1.6 mol) at r.t. After stirring overnight, water was added and the resulting mixture was extracted with EtOAc (2×20 ml). The organic layer was dried and concentrated, and the crude product was purified by column chromatography to give 7-(4-((6-benzyl-9H-purin-2-yl)amino)phenoxy)-N-((tetrahydro-2H-pyran-2-yl)oxy)heptanamide (0.4 g).

Step 7: Preparation of: 7-{4-[(6-benzyl-9H-purin-2-yl)amino]phenoxy}-N-hydroxyheptanamide

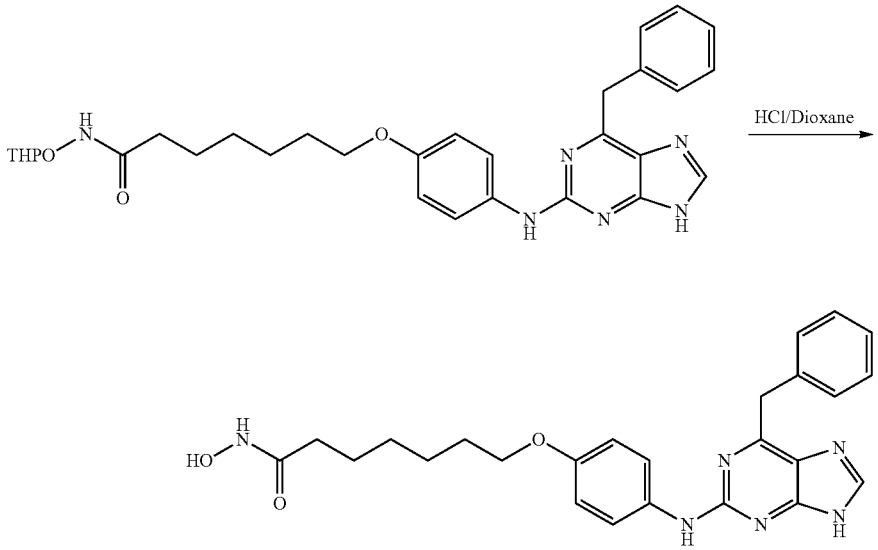

To the solution of 7-(4-((6-benzyl-9H-purin-2-yl)amino)phenoxy)-N-((tetrahydro-2H-pyran-2-yl)oxy)heptanamide (0.5 g) was dissolved in DCM (10 mL) was added HCl/Dioxane (10 mL, 4 mol/L) and the mixture was stirred for 4 hrs at r.t. Then MTBE was added and stirred for 30 min. Suspension was filtrated, filtrated cake was dried and purified by Prep-HPLC to give 7-(4-((6-benzyl-9H-purin-2-yl)amino)phenoxy)-N-hydroxyheptanamide. Mass Spec(m/z): 461.2 (M+1)

Example 36: Preparation of 7-(4-((4-(cyclohexylamino)-6,7-dihydro-5H-pyrrolo[2,3-d]pyrimidin-2-yl)amino)phenoxy)-N-hydroxyheptanamide

Step 1: Preparation of 2,4-dichloro-7-(4-methoxybenzyl)-7H-pyrrolo[2,3-d]pyrimidine

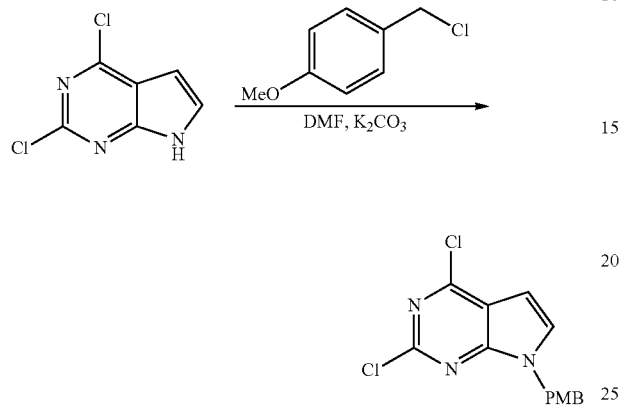

A mixture of 2,6-dichloro-9H-purine (5.0 g, 26 mmol), paramethoxybenzyl chloride (4.42 g, 28.6 mmol) and K$_2$CO$_3$ (7.2 g, 52 mmol) in DMF (50 mL) was heated to 80° C. and stirred for 4 hrs. After cooling, the mixture was poured in water, extracted with EA, and purified by column chromatography to give 2,6-dichloro-9-(4-methoxybenzyl)-9H-purine as a white solid (2 g, 21%).

Step 2: Preparation of 2-chloro-N-cyclohexyl-7-(4-methoxybenzyl)-7H-pyrrolo[2,3-d]pyrimidin-4-amine

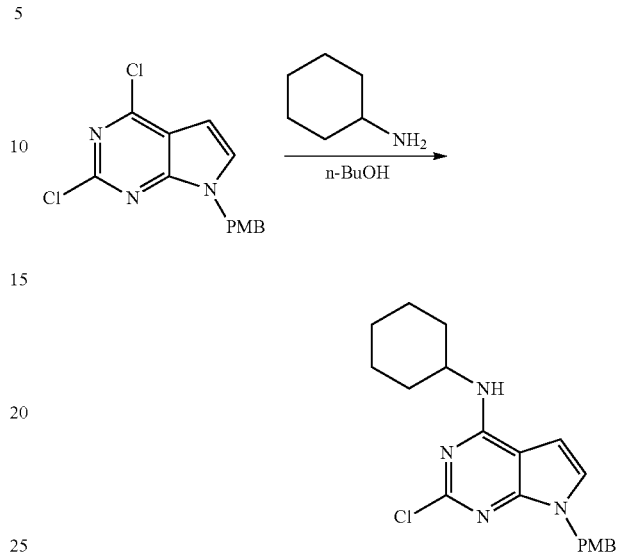

Synthesized according to the procedure described above in Example XX and purified by column chromatography to give 2-chloro-N-cyclohexyl-9-(4-methoxybenzyl)-9H-purin-6-amine (1.2 g, 49%)

Step 3: Preparation of methyl 7-(4-((4-(cyclohexylamino)-7-(4-methoxybenzyl)-7H-pyrrolo[2,3-d]pyrimidin-2-yl)amino)phenoxy)heptanoate

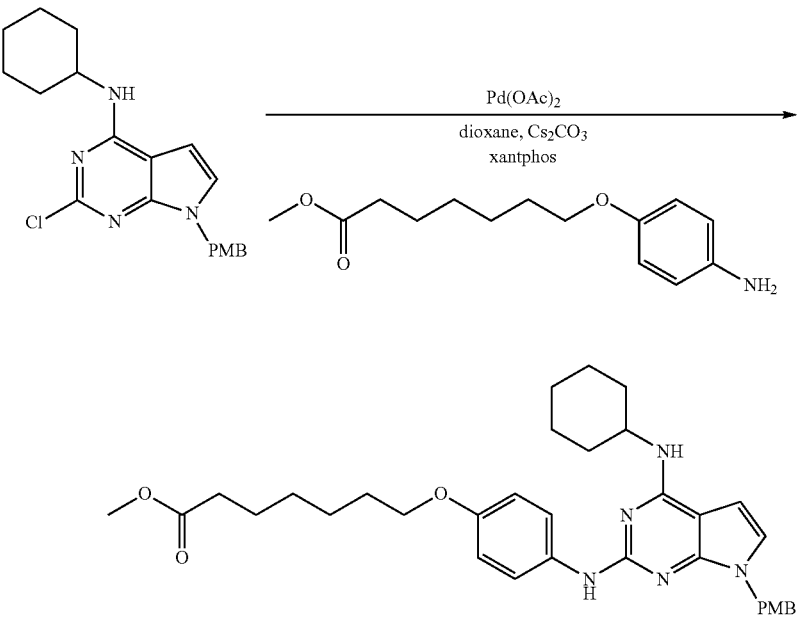

Synthesized according to the procedure described above in Example 17, step 2 and purified by column to give 7-(4-((4-(cyclohexylamino)-7-(4-methoxybenzyl)-7H-pyrrolo[2,3-d]pyrimidin-2-yl)amino)phenoxy)heptanoate as a brown solid (0.98 g, 53%).

Step 4: Preparation of methyl 7-(4-((4-(cyclohexylamino)-7-(4-methoxybenzyl)-6,7-dihydro-5H-pyrrolo[2,3-d]pyrimidin-2-yl)amino)phenoxy)heptanoate

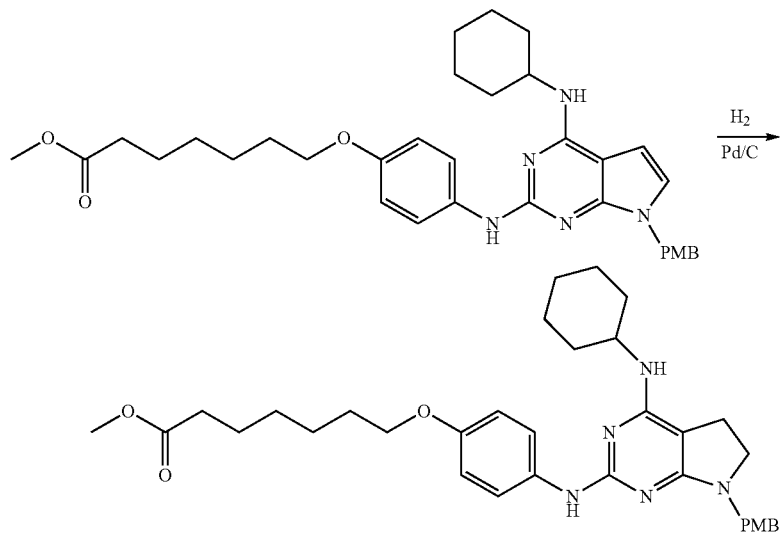

A mixture of methyl 7-(4-((4-(cyclohexylamino)-7-(4-methoxybenzyl)-7H-pyrrolo[2,3-d]pyrimidin-2-yl)amino)phenoxy)heptanoate (0.4 g, 0.68 mmol) and Pd/C (100 mg) in MeOH (10 mL) was stirred under an atmospheres of hydrogen at 40° C. overnight. The mixture was filtered and concentrated to give methyl 7-(4-((4-(cyclohexylamino)-7-(4-methoxybenzyl)-6,7-dihydro-5H-pyrrolo[2,3-d]pyrimidin-2-yl)amino)phenoxy)heptanoate (0.30 g) which was used without further purification.

Step 5: Preparation of methyl 7-(4-((4-(cyclohexylamino)-6,7-dihydro-5H-pyrrolo[2,3-d]pyrimidin-2-yl)amino)phenoxy)heptanoate

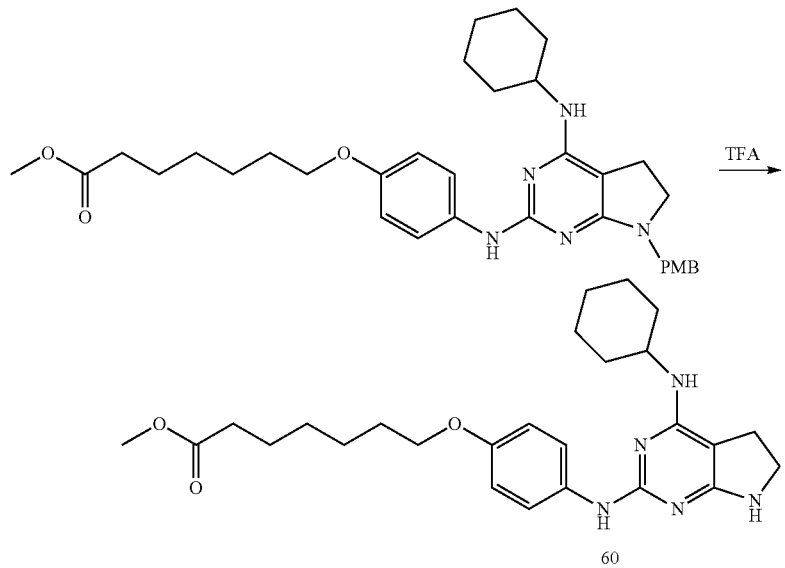

A solution of methyl 7-(4-((4-(cyclohexylamino)-7-(4-methoxybenzyl)-6,7-dihydro-5H-pyrrolo[2,3-d]pyrimidin-2-yl)amino)phenoxy)heptanoate (0.50 g) in TFA (10 mL) was heated to 60° C. for 4 hrs. cooled, and concentrated to give 7-(4-((4-(cyclohexylamino)-6,7-dihydro-5H-pyrrolo[2,3-d]pyrimidin-2-yl)amino)phenoxy)heptanoate which was used without further purification.

Step 6: Preparation of 7-(4-((4-(cyclohexylamino)-6,7-dihydro-5H-pyrrolo[2,3-d]pyrimidin-2-yl)amino)phenoxy)heptanoic acid

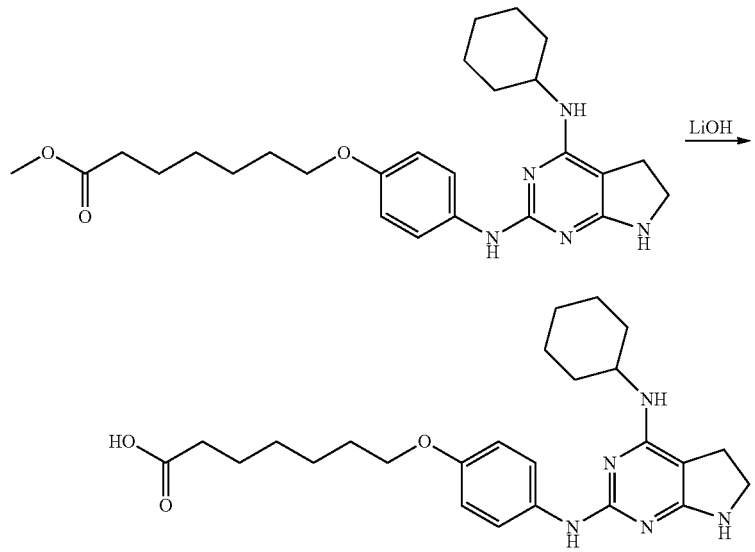

Synthesized according to the procedure described above in Example 17, step 3 and used without further purification.

Step 7: Preparation of 7-(4-((4-(cyclohexylamino)-6,7-dihydro-5H-pyrrolo[2,3-d]pyrimidin-2-yl)amino)phenoxy)-N-((tetrahydro-2H-pyran-2-yl)oxy)heptanamide

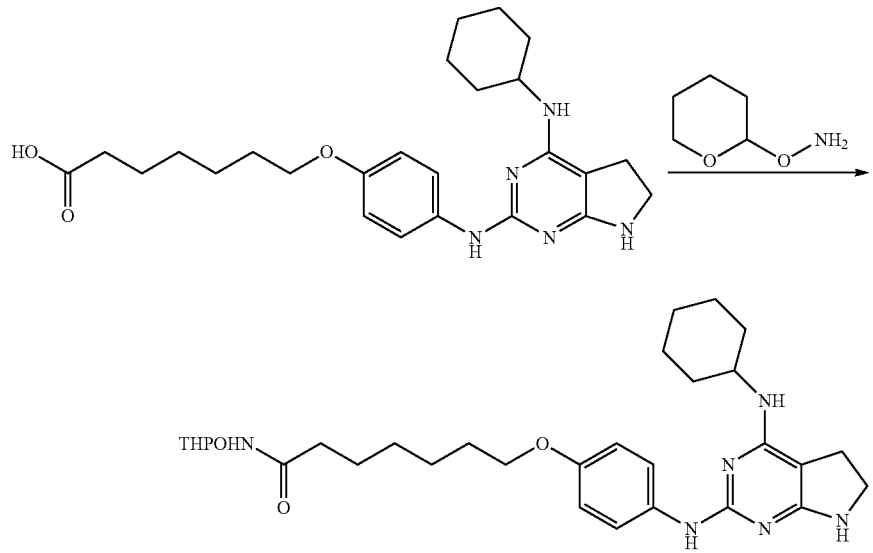

Synthesized according to the procedure described above in Example 17, step 4, and purified by column chromatography to give 7-(4-((4-(cyclohexylamino)-6,7-dihydro-5H-pyrrolo[2,3-d]pyrimidin-2-yl)amino)phenoxy)-N-((tetrahydro-2H-pyran-2-yl)oxy)heptanamide (0.28 g)

Step 8: Preparation of 7-(4-((4-(cyclohexylamino)-6,7-dihydro-5H-pyrrolo[2,3-d]pyrimidin-2-yl)amino)phenoxy)-N-hydroxyheptanamide

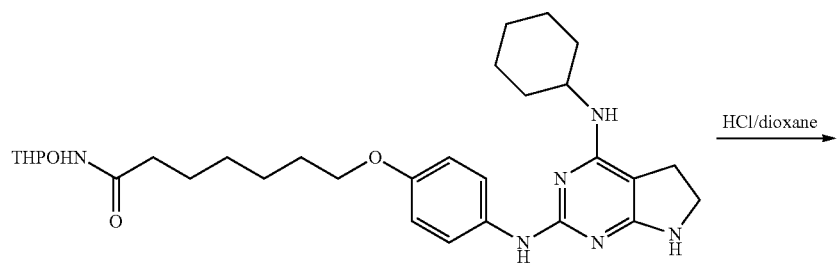

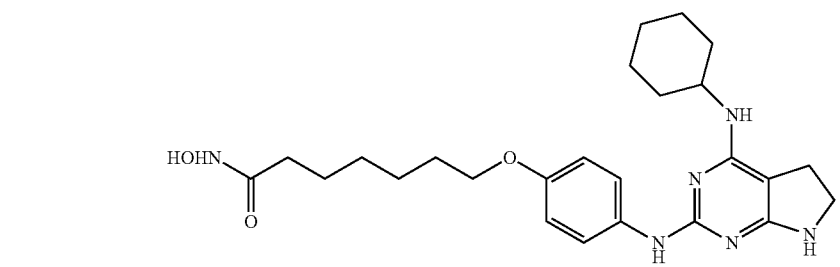

Synthesized according to the procedure described above in Example 17, step 5, and purified by preparative HPLC to give 7-(4-((4-(cyclohexylamino)-6,7-dihydro-5H-pyrrolo[2,3-d]pyrimidin-2-yl)amino)phenoxy)-N-hydroxyheptanamide (21 mg). Mass Spec(m/z): 469.2 (M+1)

Example 37: Preparation of 7-(4-((4-(cyclohexylamino)-7H-pyrrolo[2,3-d]pyrimidin-2-yl)amino)phenoxy)-N-hydroxyheptanamide

Step 1: Preparation of 2-chloro-N-cyclohexyl-7-tosyl-7H-pyrrolo[2,3-d]pyrimidin-4-amine

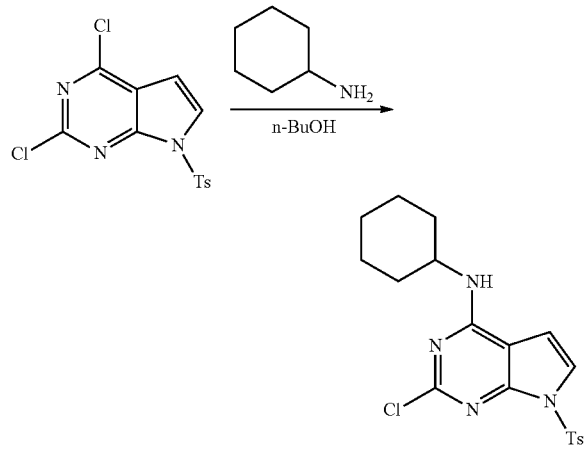

Synthesized according to the procedure described above in Example 17, Step 1 and purified by column chromatography to give 2-chloro-N-cyclohexyl-7-tosyl-7H-pyrrolo[2,3-d]pyrimidin-4-amine (0.51 g)

Step 2: Preparation of methyl 7-(4-((4-(cyclohexylamino)-7-tosyl-7H-pyrrolo[2,3-d]pyrimidin-2-yl)amino)phenoxy)heptanoate

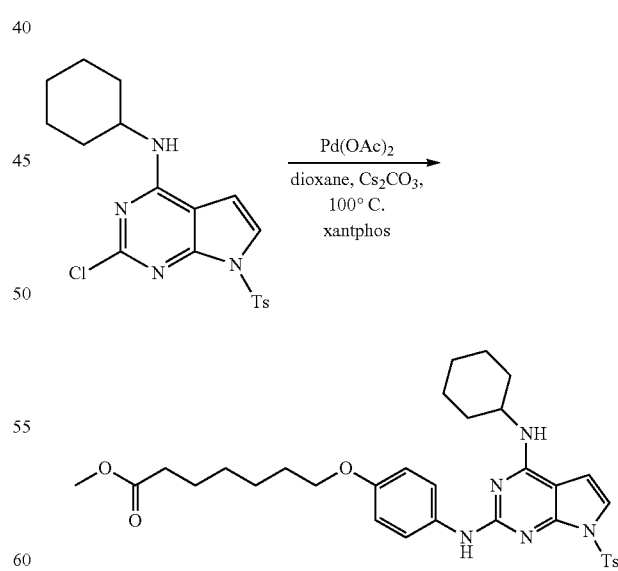

Synthesized according to the procedure described above in Example 17, step 2 and purified by column chromatography to give 7-(4-((4-(cyclohexylamino)-7-tosyl-7H-pyrrolo[2,3-d]pyrimidin-2-yl)amino)phenoxy)heptanoate as a brown solid (0.58 g, 70%)

Step 3: Preparation of 7-(4-((4-(cyclohexylamino)-7-tosyl-7H-pyrrolo[2,3-d]pyrimidin-2-yl)amino)phenoxy)heptanoic acid

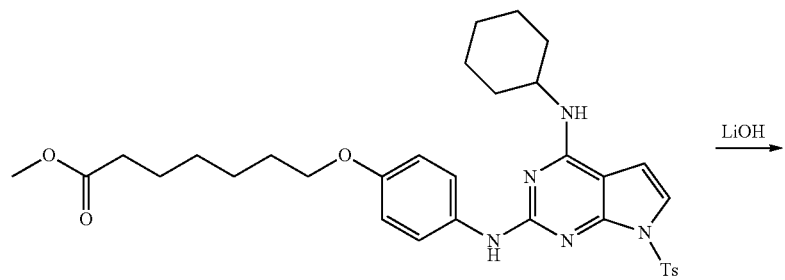

Synthesized according to the procedure described above in Example 17, Step 3 and used without further purification.

Step 4: Preparation of 7-(4-((4-(cyclohexylamino)-7H-pyrrolo[2,3-d]pyrimidin-2-yl)amino)phenoxy)heptanoic acid

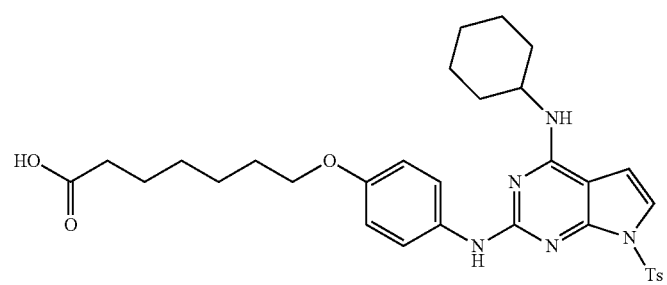

A mixture of 7-(4-((4-(cyclohexylamino)-7-tosyl-7H-pyrrolo[2,3-d]pyrimidin-2-yl)amino)phenoxy)heptanoic acid (0.70 g,) and NaOH (80 mg) in MeOH (20 mL) was heated to reflux with stirring stirred for 2 hrs. Then the mixture was cooled, concentrated, dissolved with DCM/MeOH (10/1, 20 mL) and washed with dilute HCl sol. The organic layer was dried and concentrated to give 7-(4-((4-(cyclohexylamino)-7H-pyrrolo[2,3-d]pyrimidin-2-yl)amino)phenoxy)heptanoic acid which was used without further purification

Step 5: Preparation of 7-(4-((4-(cyclohexylamino)-7H-pyrrolo[2,3-d]pyrimidin-2-yl)amino)phenoxy)-N-((tetrahydro-2H-pyran-2-yl)oxy)heptanamide

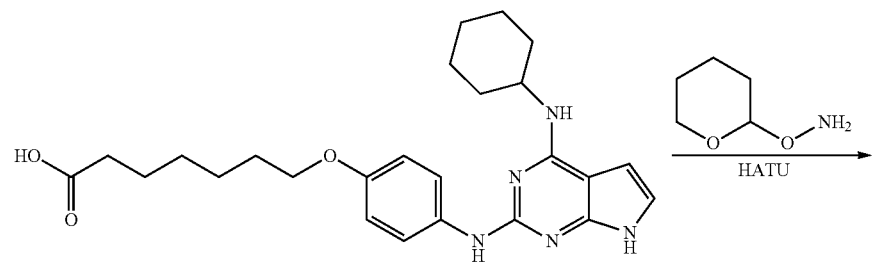

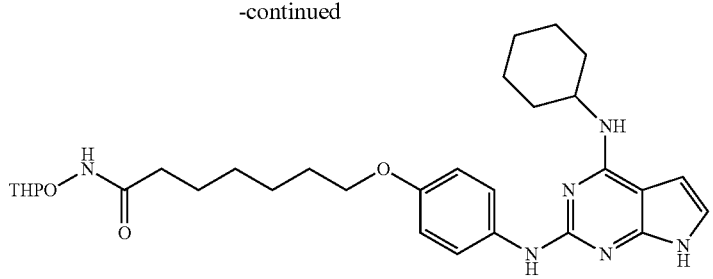

Synthesized according to the procedure described above in Example 17, step 4 and purified by column chromatography to give 7-(4-((4-(cyclohexylamino)-7H-pyrrolo[2,3-d]pyrimidin-2-yl)amino)phenoxy)-N-((tetrahydro-2H-pyran-2-yl)oxy)heptanamide

Step 6: Preparation of 7-(4-((4-(cyclohexylamino)-7H-pyrrolo[2,3-d]pyrimidin-2-yl)amino)phenoxy)-N-hydroxyheptanamide

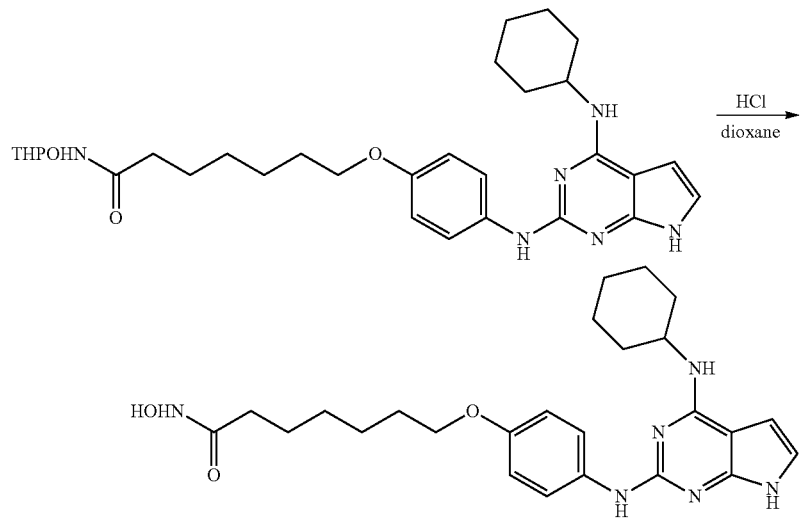

Synthesized according to the procedure described above in Example 17, step 5 and purified by preparative HPLC to give 7-(4-((4-(cyclohexylamino)-7H-pyrrolo[2,3-d]pyrimidin-2-yl)amino)phenoxy)-N-hydroxyheptanamide. Mass Spec(m/z): 467.2 (M+1)

Example 38: Preparation of 7-(4-((4-(cyclohexylamino)-1H-pyrazolo[3,4-d]pyrimidin-6-yl)amino)phenoxy)-N-hydroxyheptanamide

Step 1: Preparation of 4,6-dichloro-1-(tetrahydro-2H-pyran-2-yl)-1H-pyrazolo[3,4-d]pyrimidine A mixture of 4,6-dichloro-1H-pyrazolo[3,4-d]pyrimidine (1.0 g, 5.29 mmol), TsOH (91 mg, 0.53 mmol) and dihydropyran (1.33 g, 15.87 mol) in THF (20 mL) was heated to reflux and stirred overnight. After cooling, the mixture was concentrated to give 4,6-dichloro-1-(tetrahydro-2H-pyran-2-yl)-1H-pyrazolo[3,4-d]pyrimidine (1.2 g) which was used without further purification.

Step 2: Preparation of 6-chloro-N-cyclohexyl-1-(tetrahydro-2H-pyran-2-yl)-1H-pyrazolo[3,4-d]pyrimidin-4-amine

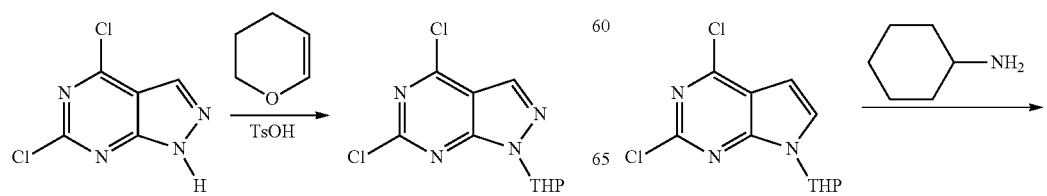

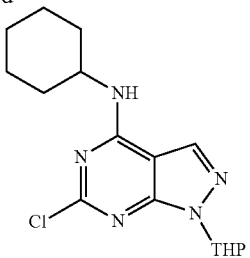

Synthesized according to the procedure described above in Example 17, Step 1 and purified by column chromatography to provide 1.1 g of 6-chloro-N-cyclohexyl-1-(tetrahydro-2H-pyran-2-yl)-1H-pyrazolo[3,4-d]pyrimidin-4-amine Step 3: Preparation of methyl 7-(4-((4-(cyclohexylamino)-1-(tetrahydro-2H-pyran-2-yl)-1H-pyrazolo[3,4-d]pyrimidin-6-yl)amino)phenoxy)heptanoate

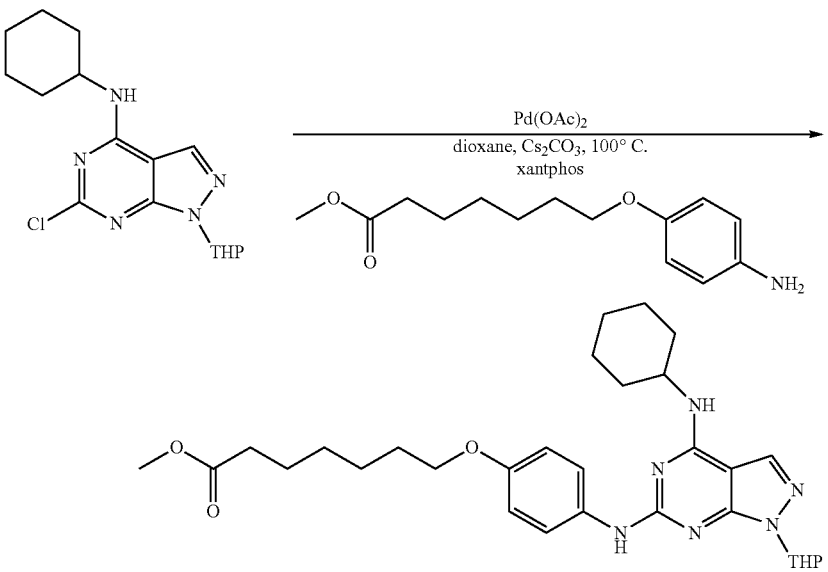

Synthesized according to the procedure described above in Example 17, Step 2 and purified by column chromatography to provide methyl 7-(4-((4-(cyclohexylamino)-1-(tetrahydro-2H-pyran-2-yl)-1H-pyrazolo[3,4-d]pyrimidin-6-yl)amino)phenoxy)heptanoate as a brown solid (0.80 g, 48%).

Step 4: Preparation of 7-(4-((4-(cyclohexylamino)-1-(tetrahydro-2H-pyran-2-yl)-1H-pyrazolo[3,4-d]pyrimidin-6-yl)amino)phenoxy)heptanoic acid

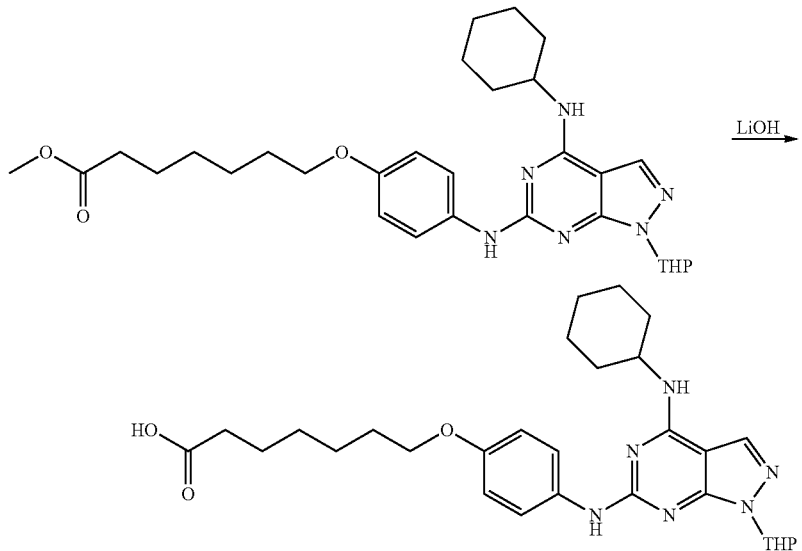

Synthesized according to the procedure described above in Example 17, Step 3 to provide 7-(4-((4-(cyclohexylamino)-1-(tetrahydro-2H-pyran-2-yl)-1H-pyrazolo[3,4-d]pyrimidin-6-yl)amino)phenoxy)heptanoic acid and used without further purification.

Step 5: Preparation of: 7-(4-((4-(cyclohexylamino)-1-(tetrahydro-2H-pyran-2-yl)-1H-pyrazolo[3,4-d]pyrimidin-6-yl)amino)phenoxy)-N-((tetrahydro-2H-pyran-2-yl)oxy)heptanamide

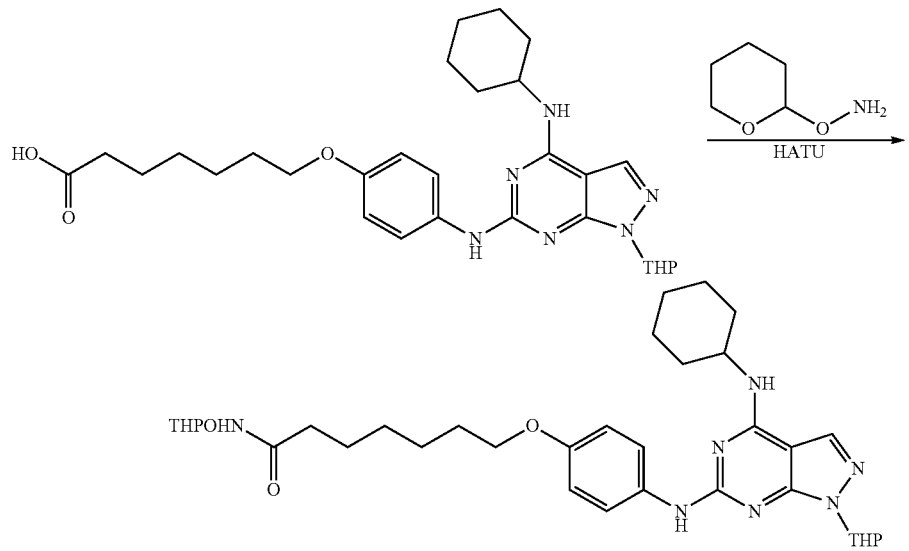

Synthesized according to the procedure described above in Example 17, Step 4 and purified by column chromatography to provide 7-(4-((4-(cyclohexylamino)-1-(tetrahydro-2H-pyran-2-yl)-1H-pyrazolo[3,4-d]pyrimidin-6-yl)amino)phenoxy)-N-((tetrahydro-2H-pyran-2-yl)oxy)heptanamide (0.28 g).

Step 6: Preparation of 7-(4-((4-(cyclohexylamino)-1H-pyrazolo[3,4-d]pyrimidin-6-yl)amino)phenoxy)-N-hydroxyheptanamide

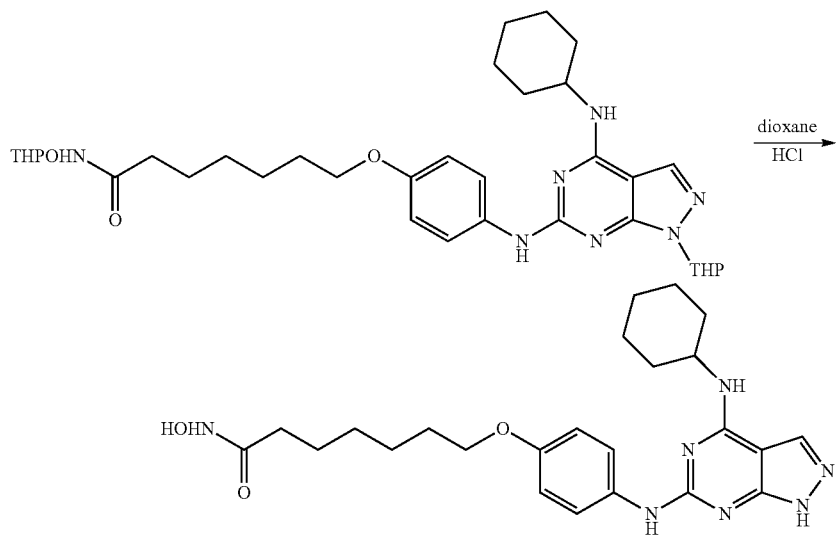

Synthesized according to the procedure described above in Example 17, Step 5 and purified by preparative HPLC to provide 7-(4-((4-(cyclohexylamino)-1H-pyrazolo[3,4-d]pyrimidin-6-yl)amino)phenoxy)-N-hydroxyheptanamide (45 mg). Mass Spec(m/z): 468.2 (M+1)

Example 39: Preparation of 7-(4-((6-(cyclohexylamino)-7-methyl-7H-purin-2-yl)amino)phenoxy)-N-hydroxyheptanamide

Step 1: Preparation of 2,6-dichloro-7-methyl-7H-purine

A mixture of 2,6-dichloro-7H-purine (5.0 g, 26.7 mmol), K$_2$CO$_3$ (5.52 g, 40 mmol) and MeI (7.58 g, 53.4 mmol) in acetonitrile (50 mL) was heated to 40° C. for 6 hrs. The reaction was cooled to r.t., filtered, and concentrated to provide a crude mixture of regioisomeric products which were separated by column chromatography. The desired isomer, 2,6-dichloro-7-methyl-7H-purine, was isolated as a white solid white solid (1.2 g, 22%).

Step 2: Preparation of 2-chloro-N-cyclohexyl-7-methyl-7H-purin-6-amine

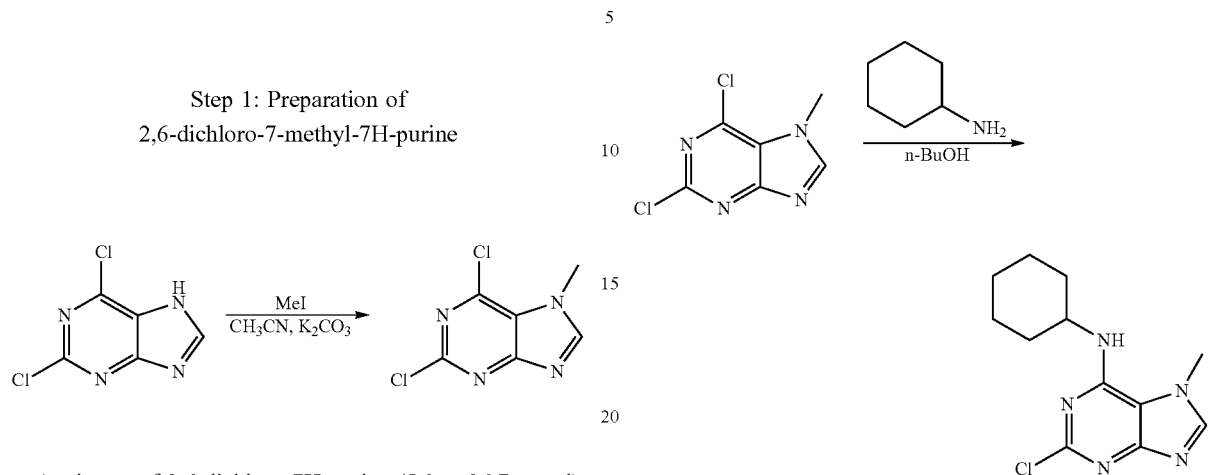

Synthesized according to the procedure described above in Example 17, Step 1 and purified by column chromatography to provide 2-chloro-N-cyclohexyl-7-methyl-7H-purin-6-amine (0.70 g, 50%)

Step 3: Preparation of methyl 7-(4-((6-(cyclohexylamino)-7-methyl-7H-purin-2-yl)amino)phenoxy)heptanoate Synthesized according to the procedure described above in Example 17, Step 2 and purified by column chromatography to provide to provide methyl 7-(4-((6-(cyclohexylamino)-7-methyl-7H-purin-2-yl)amino)phenoxy)heptanoate as a brown solid (0.58 g, 66%).

Step 4: Preparation of 7-(4-((6-(cyclohexylamino)-7-methyl-7H-purin-2-yl)amino)phenoxy)heptanoic acid

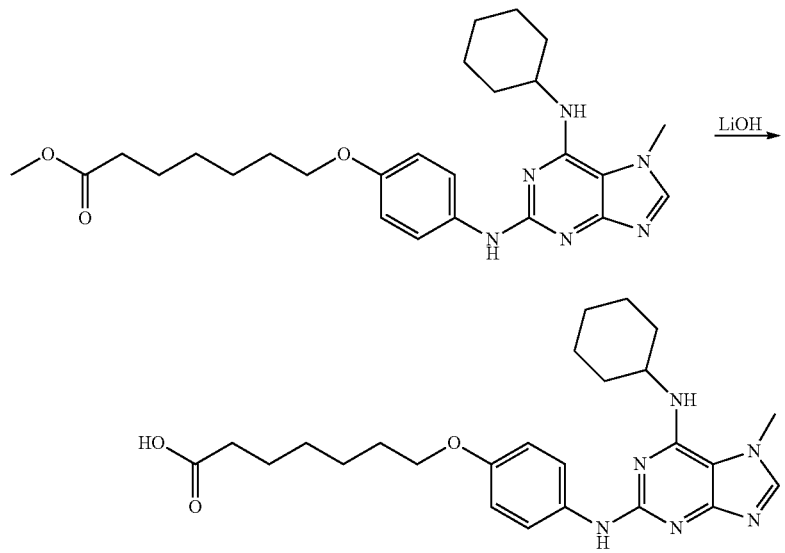

Synthesized according to the procedure described above in Example 17, Step 3 to provide 7-(4-((6-(cyclohexylamino)-7-methyl-7H-purin-2-yl)amino)phenoxy)heptanoic acid which was used without further purification.

Step 5: Preparation of 7-(4-((6-(cyclohexylamino)-7-methyl-7H-purin-2-yl)amino)phenoxy)-N-((tetrahydro-2H-pyran-2-yl)oxy)heptanamide

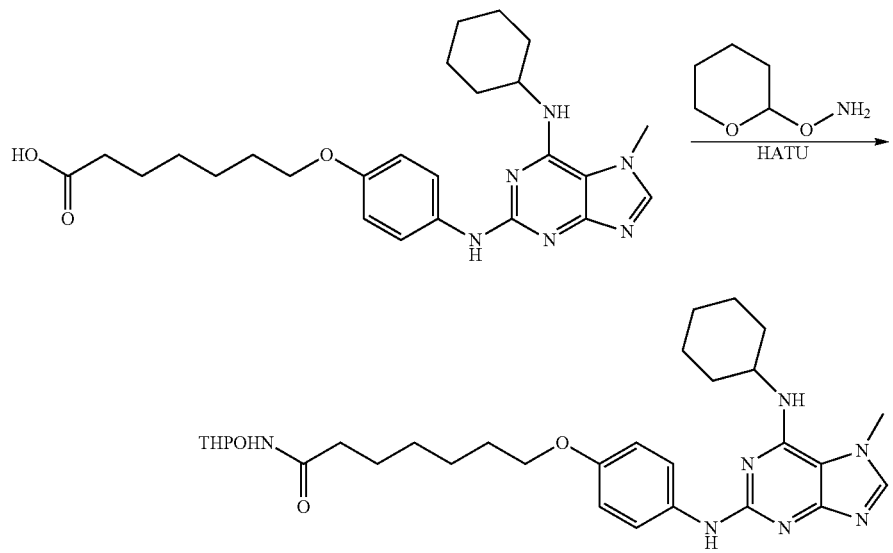

Synthesized according to the procedure described above in Example 17, Step 4 and purified by column chromatography to provide to provide 7-(4-((6-(cyclohexylamino)-7-methyl-7H-purin-2-yl)amino)phenoxy)-N-((tetrahydro-2H-pyran-2-yl)oxy)heptanamide (0.32 g, 72%).

Step 6: Preparation of 7-(4-(((6-(cyclohexylamino)-7-methyl-7H-purin-2-yl)amino)phenoxy)-N-hydroxyheptanamide

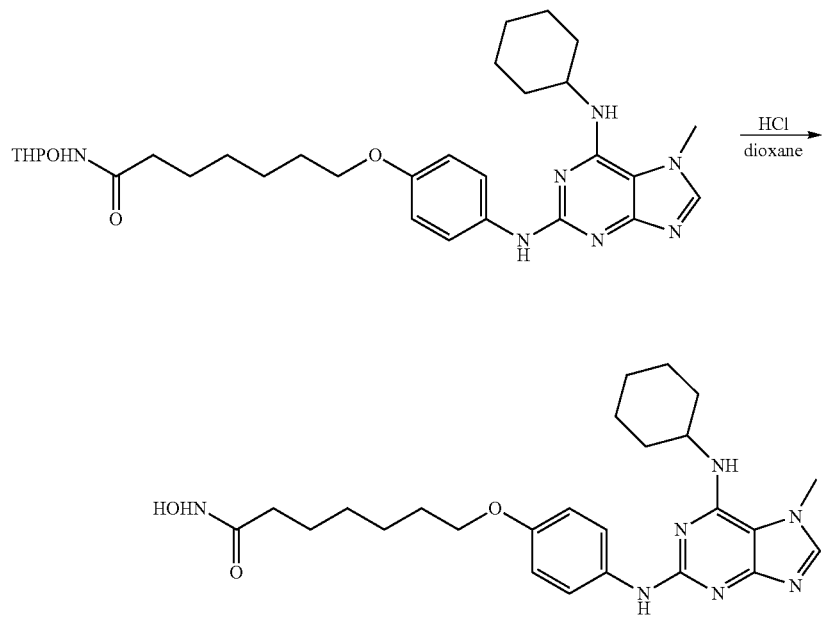

Synthesized according to the procedure described above in Example 17, Step 4 and purified by preparative HPLC to provide 7-(4-(((6-(cyclohexylamino)-7-methyl-7H-purin-2-yl)amino)phenoxy)-N-hydroxyheptanamide as a white solid (107 mg). Mass Spec(m/z): 482.4 (M+1)

Example 40: Preparation of N-hydroxy-7-(4-((6-(piperidin-1-yl)-9H-purin-2-yl)amino)phenoxy)heptanamide Step 1: Preparation of 2-chloro-6-(piperidin-1-yl)-9-(tetrahydro-2H-pyran-2-yl)-9H-purine

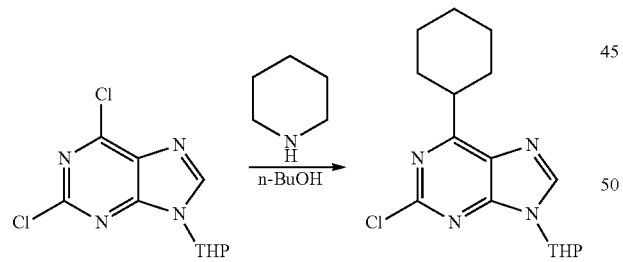

2,6-Dichloro-9-(tetrahydro-2H-pyran-2-yl)-9H-purine (2.0 g, 7.3 mol), piperidine (1.0 g, 12.2 mmol), butanol (4 mL) and TEA (0.8 g, 8 mmol) were combined and heated to 60° C. with stirring for 3 hrs. The mixture was then cooled, poured ito water and extracted with EA. The combined extracts were dried and concentrated, and the residue was purified by column chromatography to give 2-chloro-6-(piperidin-1-yl)-9-(tetrahydro-2H-pyran-2-yl)-9H-purine as a gray solid (1.6 g, 65%).

Step 2: Preparation of methyl 7-(4-(((6-(piperidin-1-yl)-9-(tetrahydro-2H-pyran-2-yl)-9H-purin-2-yl)amino)phenoxy)heptanoate

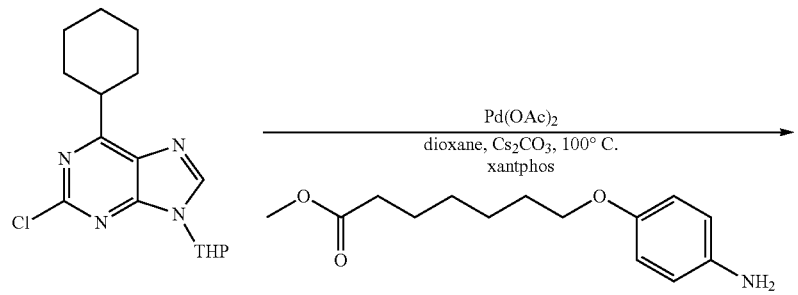

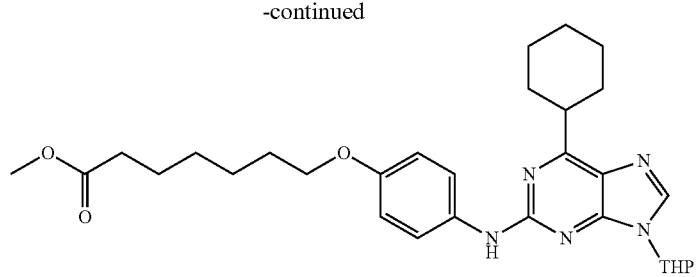

Synthesized according to the procedure described above in Example 17, Step 1 and purified by column chromatography to provide methyl 7-(4-((6-(piperidin-1-yl)-9-(tetrahydro-2H-pyran-2-yl)-9H-purin-2-yl)amino)phenoxy)heptanoate as a brown solid (1.1 g, 55.3%).

Step 3: Preparation of 7-(4-((6-(piperidin-1-yl)-9-(tetrahydro-2H-pyran-2-yl)-9H-purin-2-yl)amino)phenoxy)heptanoic acid

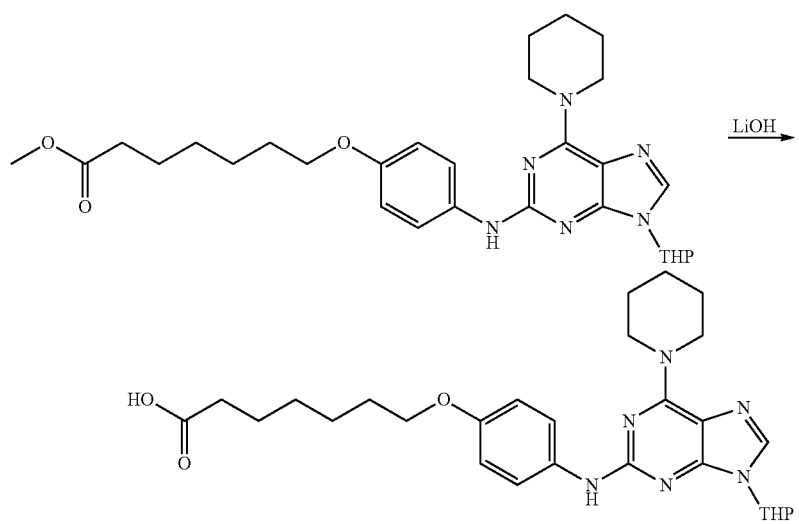

Synthesized according to the procedure described above in Example 17, Step 3 to provide 7-(4-((6-(piperidin-1-yl)-9-(tetrahydro-2H-pyran-2-yl)-9H-purin-2-yl)amino)phenoxy)heptanoic acid which was used without further purification.

Step 4: Preparation of 7-(4-((6-(piperidin-1-yl)-9-(tetrahydro-2H-pyran-2-yl)-9H-purin-2-yl)amino)phenoxy)-N-((tetrahydro-2H-pyran-2-yl)oxy)heptanamide

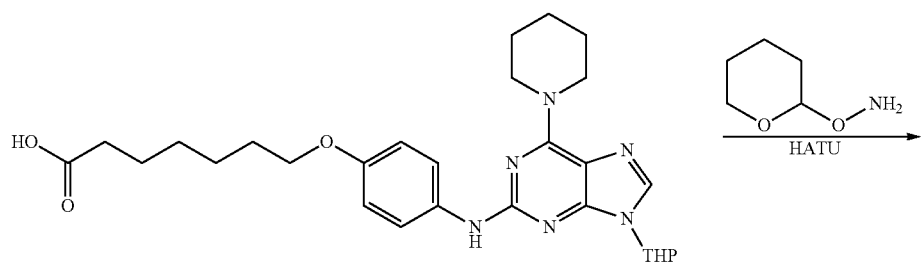

-continued

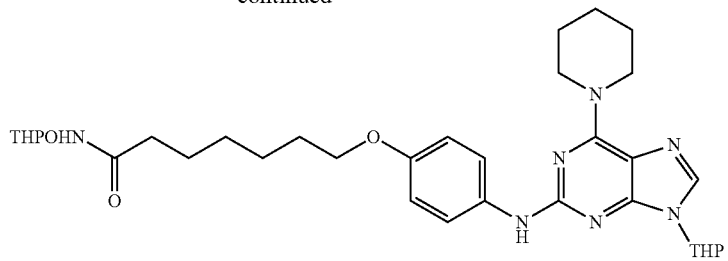

Synthesized according to the procedure described above in Example 17, Step 4 and purified with column chromatography to provide 7-(4-((6-(piperidin-1-yl)-9-(tetrahydro-2H-pyran-2-yl)-9H-purin-2-yl)amino)phenoxy)-N-((tetrahydro-2H-pyran-2-yl)oxy)heptanamide.

Step 5: N-hydroxy-7-(4-((6-(piperidin-1-yl)-9H-purin-2-yl)amino)phenoxy)heptanamide

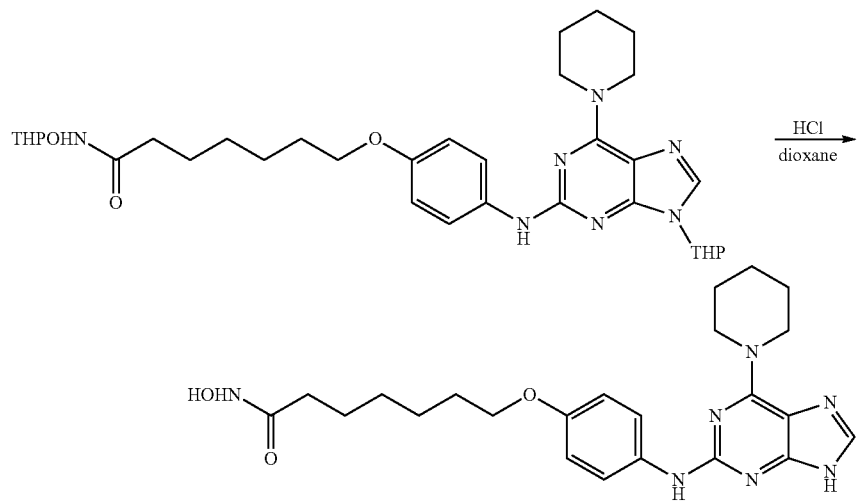

Synthesized according to the procedure described above in Example 17, Step 5 and purified bu preparative HPLC to provide N-hydroxy-7-(4-((6-(piperidin-1-yl)-9H-purin-2-yl)amino)phenoxy)heptanamide (27 mg). Mass Spec(m/z): 454.1 (M+1)

Example 41: HDAC Enzyme Assays

The inhibitory activity of HDAC compounds were tested using an HDAC Fluorescent Activity Assay based on the unique Fluor de Lys™ Substrate and Developer combination. The Fluor de Lys™ system (Fluorogenic Histone deAcetylase Lysyl Substrate/Developer) is a highly sensitive and convenient alternative to radiolabeled, acetylated histones or peptide/HPLC methods for the assay of histone deacetylases. The human HDAC enzymes (1-11) were expressed as recombinant proteins using baculoviral expression system. Recombinant HDAC enzymes were purified as either as 6×His or GST fusion proteins. For class I HDAC enzymes, fluorogenic, acetylated peptide substrate based on residues 379-382 of p53 (Arg-His-Lys-Lys(Ac)) were used as the substrate. The enzymes were diluted in HDAC reaction buffer (50 mM Tris-HCl, pH8.0, 137 mM NaCl, 2.7 mM KCl, 1 mM MgCl2. Before use, 1 mg/ml BSA (1% DMSO) was added. For Class IIb HDAC enzymes, fluorogenic, Acetyl-Lys(trifluoroacetyl) were used. The Fluor de Lys™ substrate, which comprises an acetylated lysine side chain, is incubated with test compounds at 30° C. for 2 hr. The reaction was terminated by adding Fluor de Lys™ Developer to produce a fluorophore which can be recorded with PerkinElmer Envision reader (Excite 360 nm/Emission 460 nm) at 15 min over a period of 1.5 hr. The data was collected and the $IC_{50}$ was determined using GraphPad Prism software by quadratic regression analysis. An example of the potency and selectivity of this class of compounds (as exemplified by Examples 8 and 9) compared with literature standard Trichostatin A is shown in Table 1.

TABLE 1

| Enzymes | HDAC | Example 8 | Example 9 | Trichostatin A |
|---------|-------|-----------|-----------|----------------|
| Class I | HDAC-1 | 23 nM | 422 nM | 4.6 nM |
|  | HDAC-2 | 124 nM | 1640 nM | 22 nM |
|  | HDAC-3 | 140 nM | 1180 nM | 15 nM |
|  | HDAC-8 | 268 nM | 225 nM | 490 nM |

TABLE 1-continued

| Enzymes | HDAC | Example 8 | Example 9 | Trichostatin A |
|---|---|---|---|---|
| Class IIa | HDAC-4 | >100 μM | >100 μM | 17 μM |
|  | HDAC-5 | >100 μM | >100 μM | 7 μM |
|  | HDAC-7 | >100 μM | >100 μM | 5 μM |
|  | HDAC-9 | >100 μM | >100 μM | 7 μM |
| Class IIb | HDAC-6 | 6.8 nM | 9.8 nM | 1.3 nM |
|  | HDAC-10 | 19 nM | 284 nM | 11 nM |
| Class IV | HDAC-11 | 12 nM | 159 nM | 23 nM |

Example 42: Western Blotting

For western blot analysis, total protein extracts were prepared by lysing cells in lysis buffer (50 mM Tris-Cl [pH 8.0], 5 mM EDTA, 150 mM NaCl, 1% NP-40, 0.1% SDS, and 1 mM phenylmethylsulfonyl fluoride). 50 μg of total soluble proteins were separated by SDS-PAGE. Proteins were transferred to nitrocellulose membrane and the membrane was blocked for 1 hour with 4% nonfat milk, followed by overnight incubation at 4° C. with primary antibodies against acetylated tubulin (1:1000, Abcam ab246109), Glyceraldehyde 3-phosphate dehydrogenase (GAPDH; 1:20000, Santa Cruz, sc-47724). Membranes were then incubated with peroxidase conjugated secondary antibodies for one hour at room temperature. Detection was performed using Super Signal WestDura. The expression of GAPDH was used as loading control.

Figure 2:
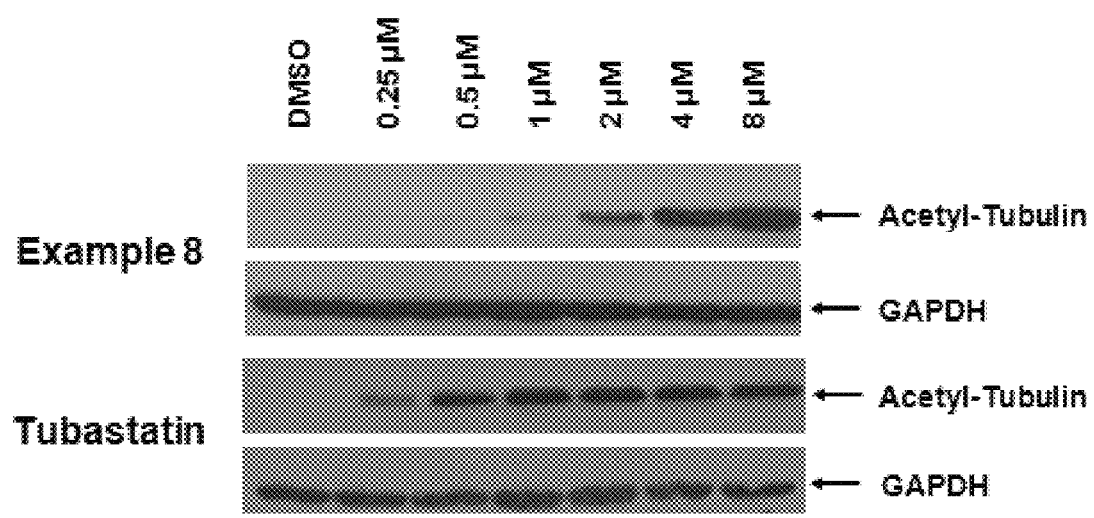
FIG. 2 illustrates the results of Tubulin acylation when treated with the compounds of Example 8.

FIGS. 1 and 2 show the results of Tubulin acylation when treated with exemplary compounds of the invention.

Example 43: NCI 60 Cell Line Data for Example 3

NCI60 tumour cell lines were screened for the activity of the test compounds and the resulting data is displayed in Table 2 below. The response parameters GI50 (50% growth inhibition) are extracted from concentration-response curves by linear interpolation. Table 2

TABLE 2

| Cell Lines | GI50 (M) |
|---|---|
| Renal Cancer | |
| 786-0 | 4.61E−06 |
| A498 | 1.95E−07 |
| ACHN | 3.57E−06 |
| CAKI-1 | 4.68E−06 |
| RXF393 | 1.90E−06 |
| SN12C | 3.23E−06 |
| TK-10 | 2.68E−06 |
| UO-31 | 3.52E−06 |
| Non-Small Cell Lung Cancer | |
| A549/ATCC | 2.30E−06 |
| HOP-62 | 2.96E−06 |
| NCI-H226 | 2.88E−06 |
| NCI-H23 | 4.73E−06 |
| NCI-H322M | 3.00E−06 |
| NCI-H460 | 2.04E−06 |
| NCI-H522 | 2.72E−06 |
| Leukemia | |
| CCRF-CEM | 6.67E−07 |
| HL-60(TB) | 2.95E−06 |
| K-562 | 2.03E−06 |
| MOLT-4 | 1.78E−06 |
| RPMI-8226 | 2.81E−06 |
| SR | 6.69E−07 |

TABLE 2-continued

| Cell Lines | GI50 (M) |
|---|---|
| Melanoma | |
| LOXIMVI | 1.18E−06 |
| MALME-3M | 2.49E−06 |
| M14 | 1.96E−06 |
| MDA-MB-435 | 2.46E−06 |
| SK-MEL-2 | 2.93E−06 |
| SK-MEL-28 | 3.64E−06 |
| SK-MEL-5 | 2.82E−06 |
| UACC-257 | 2.94E−06 |
| UACC-62 | 2.22E−06 |
| Ovarian Cancer | |
| IGROV1 | 2.24E−06 |
| OVCAR-3 | 2.17E−06 |
| OVCAR-4 | 3.82E−06 |
| OVCAR-5 | 2.26E−06 |
| OVCAR-8 | 2.80E−06 |
| NCI/ADR-RES | 1.35E−05 |
| SK-OV-3 | 2.52E−06 |
| CNS Cancer | |
| SF-268 | 3.83E−06 |
| SF-295 | 2.35E−06 |
| SF-539 | 1.57E−06 |
| SNB-19 | 5.96E−06 |
| SNB-75 | 1.69E−06 |
| U251 | 1.96E−06 |
| Breast Cancer | |
| MCF7 | 1.46E−06 |
| MDA-MB-231/ATCC | 1.93E−06 |
| HS578T | 1.61E−06 |
| BT-549 | 5.51E−06 |
| T-47D | 2.33E−06 |
| MDA-MB-468 | 2.40E−06 |
| Colon Cancer | |
| COLO205 | 1.26E−06 |
| HCC-2998 | 3.58E−06 |
| HCT-116 | 1.45E−06 |
| HCT-15 | 4.30E−06 |
| HT29 | 2.54E−06 |
| KM12 | 1.74E−06 |
| SW-620 | 8.95E−07 |
| Prostate Cancer | |
| PC-3 | 2.98E−06 |
| DU-145 | 2.51E−06 |

Example 44: Tumor Growth Inhibition on Mouse Xenograft Model

Figure 3:
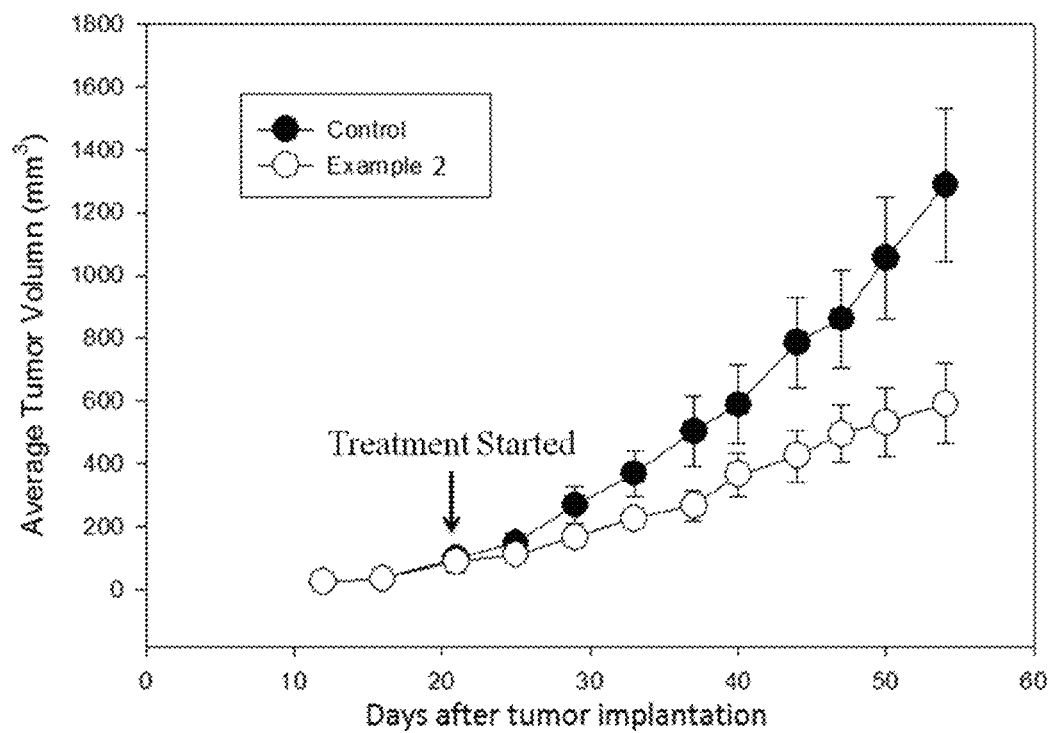
FIG. 3 illustrates the results of tumour growth inhibition on a mouse Xenograft model when treated with the compound of Example 2.

The lung non-small cell epithelial cancer cell lines A549 cultured at 37° C. with 5% CO2 and grown in media. NCI (nru) athymic nude mice 6 weeks of age were obtained from the NCI (Bethesda, Md.) and maintained in pathogen-limited conditions. s.c. injections of $2\times10^6$ A549 NSCLC tumor cells in an equal volume of Matrigel (Collaborative Biomedical Products, Bedford, Mass.) were implanted into the mouse posterior flanks before the administration of drugs. Tumor-bearing mice were randomly divided into five per group. The control group was treated with vehicle (saline solution), and the other groups were treated with 30 mg/kg/3x/wk ip of example 2. Bidimensional tumor measurements were made with calipers three times weekly until the tumors reached a volume of 3 cm3, at which time the mice were sacrificed. Tumor volume was calculated according to the formula: $V=\pi(\text{short diameter})2$ (long diameter)/6. The results are shown in FIG. 3. All animal studies were conducted with a protocol approved by the University of Colorado Health Sciences Center Institutional Animal Care and Use Committee.

The description of the present invention has been presented for purposes of illustration and description, but is not intended to be exhaustive or limiting of the invention to the form disclosed. Modifications and variations of the embodiments described herein will be apparent to those of ordinary skill in the art.

What is claimed is:

1. A compound of formula (I):

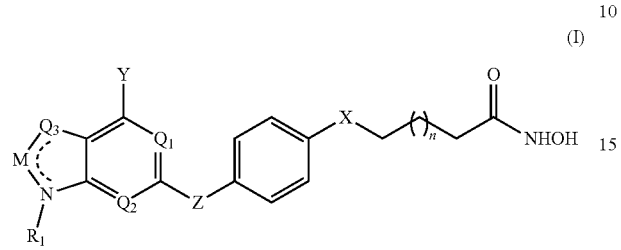

or a pharmaceutically acceptable salt thereof,
wherein:
Z is NH or $CH_2$;
X is O, S, SO, $SO_2$, CO, $CR_2R_3$, $NR_4$, $SO_2NR_4$, $NR_4SO_2$, $CONR_4$, $NR_4CO$, $NR_4CO_2$, $NR_4(CO)NR_5$ or a bond;
M is $CR_6$ or N;
$Q_1$ and $Q_2$ are independently N or CH;
$Q_3$ is $CR_7$ or $Q_3$ is $NR_8$ when $R_1$ is not present;
n is 0-6;
Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_9$, $NR_{10}COR_9$, $NR_{10}CO_2R_9$, $CONR_{10}R_{11}$, $CO_2NR_{10}R_{11}$, $NR_{10}(CO)NR_{11}$, each of which may be optionally substituted and where $R_{10}$ and $R_{11}$ taken together may form a heterocyclic ring which may be optionally substituted;
$R_1$ is H, $C_1$-$C_6$ alkyl, haloalkyl, aryl, aryl-alkyl, heteroaryl, heteroaryl-alkyl, heterocyclic, carbocyclic or absent, each of which may be optionally substituted;
$R_2$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted;
$R_3$ is H, $C_1$-$C_6$ alkyl, alkoxy, aryl, $(CH_2)_n$-aryl, heteroaryl, $(CH_2)_n$-heteroaryl, cycloalkyl or heterocyclic, any of which is substituted or unsubstituted;
$R_4$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_5$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_6$ is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_9$, $NR_{10}COR_9$, $NR_{10}CO_2R_9$, $CONR_{10}R_{11}$, $CO_2NR_{10}R_{11}$ or absent, where $R_{10}$ and $R_{11}$ taken together may form a 4-7 membered ring which may be optionally substituted;
$R_7$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_8$ is H, $C_1$-$C_6$ alkyl, haloalkyl, aryl, aryl-alkyl, heteroaryl, heteroaryl-alkyl, heterocyclic, carbocyclic or absent, each of which may be optionally substituted;

$R_9$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;
$R_{10}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and
$R_{11}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted.

2. The compound according to claim 1,
wherein:
Y is $NR_{10}R_{11}$;
$R_{10}$ is alkyl, aryl, heteroaryl, aryl-alkyl or heteroaryl-alkyl; and
$R_{11}$ is alkyl or H, and
where $R_3$ and $R_4$ taken together may form a 4-7 membered ring which is optionally substituted.

3. The compound according to claim 1, wherein X is O, S, $SO_2$, $SO_2NR_4$ or $CONR_4$.

4. The compound according to claim 1,
wherein:
$R_1$ is H or $C_1$-$C_6$ alkyl;
$Q_3$ is $NR_8$ where $R_8$ is absent; and
M is $CR_6$ where $R_6$ is H.

5. The compound according to claim 1,
wherein:
$R_1$ is H or $C_1$-$C_6$ alkyl;
$Q_3$ is $CR_7$ where $R_7$ is H; and
M is N.

6. The compound according to claim 1, wherein Y is aryl, heteroaryl or $NR_{10}R_{11}$.

7. The compound according to claim 1, having the formula (II):

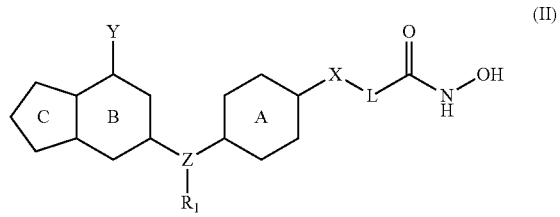

or a pharmaceutically acceptable salt, ester or prodrug thereof,
wherein:
Ring A is an optionally substituted aryl or optionally substituted heteroaryl;
Ring B is an optionally substituted aryl or optionally substituted heteroaryl;
Ring C is an optionally substituted heteroaryl, optionally substituted cycloalkyl or optionally substituted heterocycloalkyl;
Z is N, $CR_2$, O, S, C=O, SO or $SO_2$;
$R_1$ is H, absent, $C_1$-$C_6$ alkyl, haloalkyl, hydroxyalkyl, carboxyalkyl, aryl, aryl-alkyl, heteroaryl, heterocyclic or carbocyclic, each of which may be optionally substituted, and wherein when Z is $CR_2$, $R_1$ and $R_2$ taken together may form a 3-7 membered ring which may be optionally substituted;
X is O, S, SO, $SO_2$, CO, $CR_2R_3$, $NR_4$, $SO_2NR_4$, $NR_4SO_2$, $CONR_4$, $NR_4CO$, $NR_4CO_2$, $NR_4(CO)NR_5$ or a bond;
Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_3$, $SR_3$, $COR_3$, $COOR_3$, $SOR_3$, SO$_2$R$_3$, SO$_2$NR$_4$R$_5$, NR$_4$R$_5$, NR$_4$SO$_2$R$_3$, NR$_4$COR$_3$, NR$_4$CO$_2$R$_3$, CONR$_4$R$_5$, CO$_2$NR$_4$R$_5$, NR$_4$(CO)NR$_5$ or absent, each of which may be optionally substituted and where R$_4$ and R$_5$ taken together may form a 4-7 membered ring which may be optionally substituted;

L is C$_1$-C$_9$ alkylene, C$_2$-C$_9$ alkenylene or C$_2$-C$_9$ alkynylene, any of which is substituted or unsubstituted, wherein one or more of the carbon atoms of the alkylene, alkenylene or alkynylene is optionally replaced with O, S, SO, SO$_2$, SO$_2$NR$_4$, NR$_4$SO$_2$, NR$_4$, CO, CONR$_4$, NR$_4$CO, CO$_2$NR$_4$, NR$_4$CO$_2$, NR$_4$(CO)NR$_5$, a cycloalkyl or a heterocycle, with the proviso that heteroatoms are not bonded directly to alkenyl or alkynyl carbons, and that the carbon atom adjacent to X shall not be optionally replaced such that a heteroatom-heteroatom bond results;

R$_2$ is H, C$_1$-C$_6$ alkyl, hydroxy, alkoxy, aryl, (CH$_2$)$_n$-aryl, heteroaryl, (CH$_2$)$_n$-heteroaryl, cycloalkyl or heterocyclic, any of which is substituted or unsubstituted;

R$_3$ is H, C$_1$-C$_6$ alkyl, aryl, (CH$_2$)$_n$-aryl, heteroaryl, (CH$_2$)$_n$-heteroaryl, cycloalkyl or heterocyclic, any of which is substituted or unsubstituted;

R$_4$ is H, C$_1$-C$_6$ alkyl, aryl, (CH$_2$)$_n$-aryl, heteroaryl, (CH$_2$)$_n$-heteroaryl, cycloalkyl or heterocycle, any of which is substituted or unsubstituted;

R$_5$ is H, C$_1$-C$_6$ alkyl, aryl, (CH$_2$)$_n$-aryl, heteroaryl, (CH$_2$)$_n$-heteroaryl, cycloalkyl or heterocycle, any of which is substituted or unsubstituted; and n is 1-4.

8. The compound according to claim 7 or a pharmaceutically acceptable salt thereof, wherein ring A is phenyl, pyridinyl, pyrimidinyl or pyrazinyl.

9. The compound according to claim 7 or a pharmaceutically acceptable salt thereof, wherein ring B is phenyl, pyridinyl, pyrimidinyl or pyrazinyl.

10. The compound according to claim 7 or a pharmaceutically acceptable salt thereof, wherein ring C is independently selected from a 5-membered heteroaryl or a 5-membered heterocycloalkyl.

11. The compound according to claim 7 or a pharmaceutically acceptable salt thereof, wherein Y is aryl, heteroaryl, (CH$_2$)$_n$-aryl, (CH$_2$)$_n$-heteroaryl, NH$_2$, NH(alkyl), N(alkyl)(alkyl), N(aryl)(alkyl), NH(cycloalkyl), N(alkyl)(cycloalkyl), NH(heteroaryl), NH(heterocycle), N(alkyl)(heteroaryl), N(alkyl)(heterocycle), NH(alkylheteroaryl), NH(alkylheterocycle), N(alkyl)(alkyl heteroaryl) or N(alkyl)(alkylheterocycle).

12. The compound according to claim 1, having the formula (III):

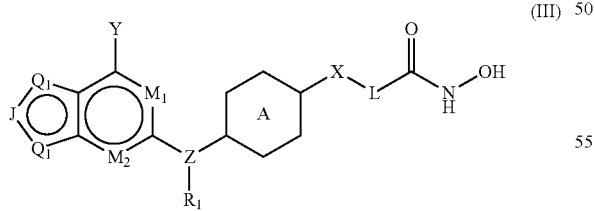

(III)

or a pharmaceutically acceptable salt thereof, wherein:

Z, is N or CR$_2$;

R$_1$ is H, C$_1$-C$_6$ alkyl, haloalkyl, hydroxyalkyl, carboxyalkyl, aryl, aryl-alkyl, heteroaryl, heterocyclic or carbocyclic, each of which may be optionally substituted, wherein, when Z is CR$_2$, R$_1$ and R$_2$ taken together may form a 3-7 membered ring which may be optionally substituted;

Ring A is an optionally substituted phenyl, pyridinyl, pyrimidinyl, or pyrazinyl;

M$_1$ and M$_2$ are independently N or CR$_3$;

Q$_1$ is CR$_4$, NR$_5$, O or S;

Q$_2$ is CR$_4$, NR$_5$, O or S;

J is N or CR$_6$;

X is O, S, SO, SO$_2$, CO, CR$_7$R$_8$, NR$_9$, SO$_2$NR$_9$, NR$_9$SO$_2$, CONR$_9$, NR$_9$CO, NR$_9$CO$_2$, NR$_9$(CO)NR$_{10}$ or a bond;

Y is H, CN, Cl, Br, I, F, C$_1$-C$_6$ alkyl, haloalkyl, cycloalkyl, heterocycloalkyl, aryl, heteroaryl, (CH$_2$)$_n$-aryl, (CH$_2$)$_n$-heteroaryl, OR$_8$, SR$_8$, COR$_8$, COOR$_8$, SOR$_8$, SO$_2$R$_8$, SO$_2$NR$_9$R$_{10}$, NR$_9$R$_{10}$, NR$_9$SO$_2$R$_8$, NR$_9$COR$_8$, NR$_9$CO$_2$R$_8$, CONR$_9$R$_{10}$, CO$_2$NR$_9$R$_{10}$, or NR$_9$(CO)NR$_{10}$, each of which may be optionally substituted and where R$_9$ and R$_{10}$ taken together may form a heterocyclic ring which may be optionally substituted;

L is C$_1$-C$_9$ alkylene, C$_2$-C$_9$ alkenylene or C$_2$-C$_9$ alkynylene, any of which is substituted or unsubstituted, wherein one or more of the carbon atoms of the alkylene, alkenylene or alkynylene is optionally replaced with O, S, SO, SO$_2$, SR$_8$, SO$_2$NR$_9$, NR$_9$SO$_2$, NR$_9$, CO, CONR$_9$, NR$_9$CO, CO$_2$NR$_9$, NR$_9$CO$_2$, a cycloalkyl or a heterocycle, with the proviso that heteroatoms are not bonded directly to alkenyl or alkynyl carbons, and that the carbon adjacent to X shall not be optionally replaced such that a heteroatom-heteroatom bond results;

R$_2$ is H, C$_1$-C$_6$ alkyl, hydroxy, alkoxy, aryl, (CH$_2$)$_n$-aryl, heteroaryl, (CH$_2$)$_n$-heteroaryl, cycloalkyl or heterocyclic, any of which is substituted or unsubstituted;

R$_3$ is H, CN, Cl, Br, I, F, C$_1$-C$_6$ alkyl, haloalkyl, cycloalkyl, heterocycloalkyl, aryl, heteroaryl, OR$_8$, SR$_8$, COR$_8$, COOR$_8$, SOR$_8$, SO$_2$R$_8$, SO$_2$NR$_9$R$_{10}$, NR$_9$R$_{10}$, NR$_9$SO$_2$R$_8$, NR$_9$COR$_8$, NR$_9$CO$_2$R$_8$, CONR$_9$R$_{10}$, CO$_2$NR$_9$R$_{10}$ or NR$_9$(CO)NR$_{10}$, each of which may be optionally substituted and where R$_9$ and R$_{10}$ taken together may form a heterocyclic ring which may be optionally substituted;

R$_4$ is H, C$_1$-C$_6$ alkyl, haloalkyl, hydroxyalkyl, carboxyalkyl, aryl, aryl-alkyl, heteroaryl, heterocyclic or carbocyclic, each of which may be optionally substituted;

R$_5$ is H, C$_1$-C$_6$ alkyl, haloalkyl, hydroxyalkyl, carboxyalkyl, aryl, aryl-alkyl, heteroaryl, heterocyclic or carbocyclic, each of which may be optionally substituted;

R$_6$ is H, CN, Cl, Br, I, F, C$_1$-C$_6$ alkyl, haloalkyl, cycloalkyl, heterocycloalkyl, aryl, heteroaryl, OR$_8$, SR$_8$, COR$_8$, COOR$_8$, SOR$_8$, SO$_2$R$_8$, SO$_2$NR$_9$R$_{10}$, NR$_9$R$_{10}$, NR$_9$SO$_2$R$_8$, NR$_9$COR$_8$, NR$_9$CO$_2$R$_8$, CONR$_9$R$_{10}$, CO$_2$NR$_9$R$_{10}$ or NR$_9$(CO)NR$_{10}$, each of which may be optionally substituted and where R$_9$ and R$_{10}$ taken together may form a heterocyclic ring which may be optionally substituted;

R$_7$ is H, C$_1$-C$_6$ alkyl, alkoxy, aryl, (CH$_2$)$_n$-aryl, heteroaryl, (CH$_2$)$_n$-heteroaryl, cycloalkyl or heterocyclic, any of which is substituted or unsubstituted;

R$_8$ is H, C$_1$-C$_6$ alkyl, aryl, (CH$_2$)$_n$-aryl, heteroaryl, (CH$_2$)$_n$-heteroaryl, cycloalkyl or heterocyclic, any of which is substituted or unsubstituted;

R$_9$ is H, C$_1$-C$_6$ alkyl, aryl, (CH$_2$)$_n$-aryl, heteroaryl, (CH$_2$)$_n$-heteroaryl, cycloalkyl or heterocyclic, any of which is substituted or unsubstituted;

R$_{10}$ is H, C$_1$-C$_6$ alkyl, aryl, (CH$_2$)$_n$-aryl, heteroaryl, (CH$_2$)$_n$-heteroaryl, cycloalkyl or heterocyclic, any of which is substituted or unsubstituted; and n is 1-4.

13. The compound according to claim 12, or a pharmaceutically acceptable salt thereof, wherein Z is nitrogen and $R_1$ is H.

14. The compound according to claim 12, or a pharmaceutically acceptable salt thereof, wherein X and Z are oriented para to each other.

15. The compound according to claim 12, or a pharmaceutically acceptable salt thereof, wherein Y is aryl, heteroaryl, alkyl-aryl, alkyl-heteroaryl, $NH_2$, NH(alkyl), N(alkyl)(alkyl), N(aryl)(alkyl), NH(cycloalkyl), N(alkyl)(cycloalkyl), NH(heteroaryl), NH(heterocycle), N(alkyl)(heteroaryl), N(alkyl)(heterocycle), NH(alkylheteroaryl), NH(alkylheterocycle), N(alkyl)(alkyl heteroaryl) or N(alkyl)(alkylheterocycle).

16. The compound according to claim 12, or a pharmaceutically acceptable salt thereof, wherein $M_1$, and $M_2$ are independently N or $CR_3$, where $R_3$ is H.

17. The compound according to claim 12, or a pharmaceutically acceptable salt thereof, wherein $Q_1$ is $NR_5$; $Q_2$ is $NR_7$; and J is $CR_6$, where $R_5$ is absent and $R_7$ is H or alkyl.

18. The compound according to claim 12, or a pharmaceutically acceptable salt thereof, wherein $Q_1$ is $NR_5$; $Q_2$ is $NR_7$; and J is $CR_6$, where $R_5$ is alkyl and $R_7$ is absent.

19. A compound according to claim 1, having the formula (IV):

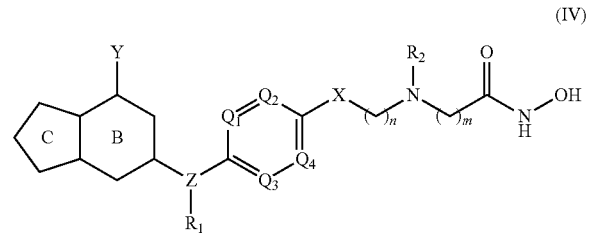

(IV)

or a pharmaceutically acceptable salt thereof,
wherein:
Z is N or $CR_3$;
$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted, wherein, when Z is $CR_3$, $R_1$ and $R_3$ taken together may form a 3-7 membered ring which may be optionally substituted;
$R_2$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted;
$R_3$ is H, $C_1$-$C_6$ alkyl, hydroxy, alkoxy, aryl, $(CH_2)_q$-aryl, heteroaryl, $(CH_2)_q$-heteroaryl, cycloalkyl or heterocyclic, any of which is substituted or unsubstituted, where $R_1$ and $R_3$ taken together may form a 3-7 membered ring which may be optionally substituted;
each of $Q_1$, $Q_2$, $Q_3$ and $Q_4$ is independently N or $CR_4$;
Ring B is an optionally substituted phenyl, pyridinyl, pyrimidinyl or pyrazinyl;
Ring C is an optionally substituted heteroaryl, optionally substituted cycloalkyl or optionally substituted heterocycloalkyl;
X is O, S, SO, $SO_2$, CO, $CR_5R_6$, $NR_7$, $SO_2NR_7$, $NR_7SO_2$, $CONR_7$, $NR_7CO$, $NR_7CO_2$, $NR_7(CO)NR_8$ or a bond, wherein, $R_5$ and $R_6$ taken together may form a 3-7 membered ring which may be optionally substituted;
Y is H, CN, Cl, Br, I, F, $C_1$-$C_6$ alkyl, haloalkyl, cycloalkyl, heterocycloalkyl, aryl, heteroaryl, $(CH_2)_q$-aryl, $(CH_2)_q$-heteroaryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_7$, $CONR_7R_8$, $CO_2NR_7R_8$, $NR_7(CO)NR_8$, or absent, each of which may be optionally substituted and where $R_7$ and $R_8$ taken together may form a heterocyclic ring which may be optionally substituted;
n is 1-5 and m is 1-5 when X is $CR_5R_6$;
n is 2-4 and m is 1-4 when X is other than $CR_5R_6$;
q is 2-4;
$R_4$ is H, CN, Cl, Br, I, F, alkyl, haloalkyl, cycloalkyl, heterocycloalkyl, aryl, heteroaryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_6$, $CONR_7R_8$, $CO_2NR_7R_8$ or $NR_7(CO)NR_8$, each of which may be optionally substituted and where $R_7$ and $R_8$ taken together may form a heterocyclic ring which may be optionally substituted;
$R_5$ is H, $C_1$-$C_6$ alkyl, alkoxy, aryl, $(CH_2)_q$-aryl, heteroaryl, $(CH_2)_q$-heteroaryl, cycloalkyl or heterocyclic, any of which is substituted or unsubstituted;
$R_6$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted;
$R_7$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted;
$R_8$ is H, $C_1$-$C_6$ alkyl, aryl, $(CH_2)_q$-aryl, heteroaryl, $(CH_2)_q$-heteroaryl, cycloalkyl or heterocyclic, any of which is substituted or unsubstituted.

20. The compound according to claim 19, or a pharmaceutically acceptable salt thereof, wherein rings B and C taken together form a purine, pyrazolopyrimidine, pyrazolopyridine, pyrrolopyrimidine, thiazolopyrimidine, purinone, indole, pyrrolopyrimidinone or dihydropyrrolopyrimidine.

21. The compound according to claim 19, or a pharmaceutically acceptable salt thereof, wherein $Q_1$ and $Q_3$ are N; and $Q_2$ and $Q_4$ are $CR_4$ where $R_4$ is H.

22. The compound according to claim 19, or a pharmaceutically acceptable salt thereof, wherein $Q_1$ and $Q_3$ are $CR_4$ where $R_4$ is H; and $Q_2$ and $Q_4$ are N.

23. The compound according to claim 19, or a pharmaceutically acceptable salt thereof, wherein $Q_1$, $Q_2$, $Q_3$ and $Q_4$ are $CR_4$ where $R_4$ is H.

24. The compound according to claim 19, or a pharmaceutically acceptable salt thereof, wherein Z is N; and $R_1$ is H.

25. The compound according to claim 19, or a pharmaceutically acceptable salt thereof, wherein X is O, $(CO)NR_8$ or $S(O)_2NR_8$; and $R_8$ is H, alkyl, aryl, heteroaryl, cycloalkyl or heterocyclic, any of which is substituted or unsubstituted.

26. The compound according to claim 19, or a pharmaceutically acceptable salt thereof, wherein n is 3; m is 1; and $R_2$ is H or alkyl.

27. A compound according to claim 1, having the formula (V):

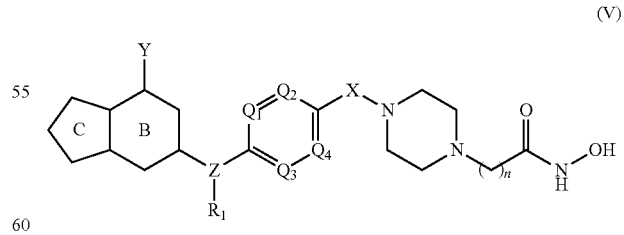

(V)

or a pharmaceutically acceptable salt thereof,
wherein:
Z is N or $CR_2$;
$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted;

each of $Q_1$, $Q_2$, $Q_3$, and $Q_4$ is independently N or $CR_3$;

Ring B is an optionally substituted phenyl, pyridinyl, pyrimidinyl or pyrazinyl;

Ring C is an optionally substituted heteroaryl, optionally substituted cycloalkyl or optionally substituted heterocycloalkyl;

$R_2$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted, where $R_1$ and $R_3$ taken together may form a 3-7 membered ring which may be optionally substituted;

X is $(CR_4R_5)_n$, $SO_2$, CO, $NR_6CO$ or absent;

Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, aryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_6$, $CONR_7R_8$, $CO_2NR_7R_8$ or absent, and where $R_7$ and $R_8$ taken together may form a 4-7 membered ring which may be optionally substituted;

n=1-4;

$R_3$ is H, CN, Cl, Br, I, F, $C_1$-$C_6$ alkyl, haloalkyl, cycloalkyl, heterocycloalkyl, aryl, heteroaryl, $OR_6$, $SR_6$, $COR_6$, $COOR_6$, $SOR_6$, $SO_2R_6$, $SO_2NR_7R_8$, $NR_7R_8$, $NR_7SO_2R_6$, $NR_7COR_6$, $NR_7CO_2R_6$, $CONR_7R_8$, $CO_2NR_7R_8$ or $NR_7(CO)NR_8$, each of which may be optionally substituted and where $R_7$ and $R_8$ taken together may form a heterocyclic ring which may be optionally substituted;

$R_4$ is H, $C_1$-$C_6$ alkyl, aryl, heteroaryl, cycloalkyl or heterocyclic, any of which is substituted or unsubstituted;

$R_5$ is H, $C_1$-$C_6$ alkyl, aryl, heteroaryl, cycloalkyl or heterocyclic, any of which is substituted or unsubstituted;

$R_6$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_7$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and $R_8$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted.

28. The compound according to claim 27, or a pharmaceutically acceptable salt thereof, wherein rings B and C taken together form a purine, pyrazolopyrimidine, pyrazolopyridine, pyrrolopyrimidine, thiazolopyrimidine, purinone, indole, pyrrolopyrimidinone or dihydropyrrolopyrimidine.

29. The compound according to claim 27, or a pharmaceutically acceptable salt thereof, wherein Z is N, and $R_1$ is H.

30. The compound according to claim 27, or a pharmaceutically acceptable salt thereof, wherein $Q_1$, $Q_2$, $Q_3$ and $Q_4$ are $CR_3$ where $R_3$ is H.

31. The compound according to claim 27, or a pharmaceutically acceptable salt thereof, wherein X is $CR_4R_5$, $SO_2$, CO, $NR_4CO$ or absent.

32. The compound according to claim 27, or a pharmaceutically acceptable salt thereof, wherein Y is aryl, heteroaryl, $(CH_2)_n$-aryl, $(CH_2)_n$-heteroaryl or $NR_7R_8$.

33. A compound according to claim 1, having the formula (VI):

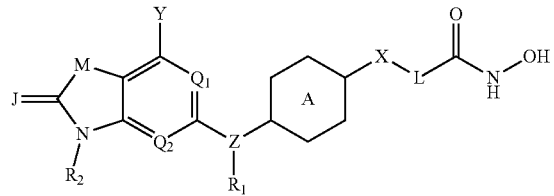

or a pharmaceutically acceptable salt, ester or prodrug thereof, wherein:

Ring A is an optionally substituted aryl or optionally substituted heteroaryl;

Z is N or $CR_3$;

$R_1$ is H, $C_1$-$C_6$ alkyl, haloalkyl, hydroxyalkyl, carboxyalkyl, aryl, aryl-alkyl, heteroaryl, heterocyclic or carbocyclic, each of which may be optionally substituted;

$R_2$ is an optionally substituted $C_1$-$C_6$ alkyl, acyl, aryl or heteroaryl;

$Q_1$ and $Q_2$ are independently N or $CR_4$;

M is $NR_5$, $CR_6R_7$, O or S;

J is O, S or absent;

X is O, S, SO, $SO_2$, CO, $CR_8R_9$, $NR_{10}$, $SO_2NR_{10}$, $NR_{10}SO_2$, $CONR_{10}$, $NR_9CO$, $NR_{10}CO_2$, $NR_{10}(CO)NR_{11}$ or absent;

Y is H, CN, Cl, Br, I, F, $C_1$-$C_6$ alkyl, haloalkyl, cycloalkyl, heterocycloalkyl, aryl, heteroaryl, $(CH_2)_n$-aryl, $(CH_2)_n$-heteroaryl, $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_9$, $NR_{10}COR_9$, $NR_{10}CO_2R_9$, $CONR_{10}R_{11}$, $CO_2NR_{10}R_{11}$ or absent, where $R_{10}$ and $R_{11}$ taken together may form a 4-7 membered ring which may be optionally substituted;

L is $C_1$-$C_9$ alkylene, $C_2$-$C_9$ alkenylene or $C_2$-$C_9$ alkynylene, any of which is substituted or unsubstituted, wherein one or more of the carbon atoms of the alkylene, alkenylene or alkynylene is optionally replaced with O, S, SO, $SO_2$, $SO_2NR_{10}$, $NR_{10}SO_2$, $NR_{10}$, CO, $CONR_{10}$, $NR_{10}CO$, $CO_2NR_{10}$, $NR_{10}CO_2$, cycloalkyl or heterocyclic, with the proviso that heteroatoms are not bonded directly to alkenyl or alkynyl carbons, and that the carbon adjacent to X shall not be optionally replaced such that a heteroatom-heteroatom bond results;

$R_3$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted, where $R_1$ and $R_3$ taken together may form a 3-7 membered ring which may be optionally substituted;

$R_4$ is H, CN, Cl, Br, I, F, $C_1$-$C_6$ alkyl, haloalkyl, cycloalkyl, heterocycloalkyl, aryl, heteroaryl $OR_9$, $SR_9$, $COR_9$, $COOR_9$, $SOR_9$, $SO_2R_9$, $SO_2NR_{10}R_{11}$, $NR_{10}R_{11}$, $NR_{10}SO_2R_{11}$, $NR_{10}COR_9$, $NR_{10}CO_2R_9$, $CONR_{10}R_{11}$ or $CO_2NR_{10}R_{11}$, where $R_{10}$ and $R_{11}$ taken together may form a 4-7 membered ring which may be optionally substituted;

$R_5$ is an optionally substituted $C_1$-$C_6$ alkyl, acyl, aryl or heteroaryl;

$R_6$ is H, $C_1$-$C_6$ alkyl, hydroxy, alkoxy, aryl, $(CH_2)_n$-aryl, heteroaryl, $(CH_2)_n$-heteroaryl, cycloalkyl or heterocycle;

$R_7$ is H, $C_1$-$C_6$ alkyl, hydroxy, alkoxy, aryl, $(CH_2)_n$-aryl, heteroaryl, $(CH_2)_n$-heteroaryl, cycloalkyl or heterocyclic, any of which is substituted or unsubstituted, where $R_6$ and $R_7$ taken together may form a 3-7 membered ring which may be optionally substituted;

$R_8$ is H, $C_1$-$C_6$ alkyl, alkoxy, aryl, $(CH_2)_n$-aryl, heteroaryl, $(CH_2)_n$-heteroaryl, cycloalkyl or heterocycle, any of which is substituted or unsubstituted;

$R_9$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_{10}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted;

$R_{11}$ is H, $C_1$-$C_6$ alkyl, aryl, $(CH_2)_n$-aryl, heteroaryl, $(CH_2)_n$-heteroaryl, cycloalkyl or heterocyclic, any of which is substituted or unsubstituted; and n is 1-4.

34. The compound according to claim 33, or a pharmaceutically acceptable salt thereof, wherein Z is N; and $R_1$ is H.

35. The compound according to claim 33, or a pharmaceutically acceptable salt thereof, wherein $Q_1$ and $Q_2$ are independently N or $CR_4$ where $R_4$ is H.

36. The compound according to claim 33, or a pharmaceutically acceptable salt thereof, wherein M is $CR_6R_7$ where $R_6$ and $R_7$ are alkyl, or taken together form a 3, 4, or 5 membered ring.

37. The compound according to claim 33, or a pharmaceutically acceptable salt thereof, wherein Ring A is phenyl.

38. The compound according to claim 33, or a pharmaceutically acceptable salt thereof, wherein X and Z are oriented para to each other.

39. The compound according to claim 33, or a pharmaceutically acceptable salt thereof, wherein X is O, $CR_8R_9$ or $CONR_{10}$.

40. The compound according to claim 33, or a pharmaceutically acceptable salt thereof, wherein J is O or absent.

41. The compound according to claim 33, or a pharmaceutically acceptable salt thereof, wherein Y is aryl, heteroaryl, $(CH_2)_n$-aryl, $(CH_2)_n$-heteroaryl or $NR_7R_8$.

42. The compound according to claim 33, or a pharmaceutically acceptable salt thereof, wherein L is $C_3$-$C_8$alkylene.

43. A pharmaceutical composition comprising a compound of any one of formulae (I) through (VI) or a pharmaceutically acceptable salt thereof in combination with a diluent or excipient.

* * * * *